(12) United States Patent
Hu et al.

(10) Patent No.: US 7,777,476 B2
(45) Date of Patent: Aug. 17, 2010

(54) DYNAMIC MODULATION FOR MULTIPLEXATION OF MICROFLUIDIC AND NANOFLUIDIC BASED BIOSENSORS

(75) Inventors: Jun Hu, Fairlawn, OH (US); Jiang Zhe, Copley, OH (US)

(73) Assignee: The University of Akron, Akron, OH (US)

( * ) Notice: Subject to any disclaimer, the term of this patent is extended or adjusted under 35 U.S.C. 154(b) by 229 days.

(21) Appl. No.: 12/139,551

(22) Filed: Jun. 16, 2008

(65) Prior Publication Data
US 2009/0066315 A1 Mar. 12, 2009

Related U.S. Application Data

(63) Continuation of application No. 11/584,945, filed on Oct. 23, 2006, now Pat. No. 7,397,232.

(60) Provisional application No. 60/729,262, filed on Oct. 21, 2005.

(51) Int. Cl.
*G01N 27/00* (2006.01)
*G01N 15/00* (2006.01)

(52) U.S. Cl. .................. 324/71.4; 324/71.1; 73/865.5

(58) Field of Classification Search .............. 324/71.4, 324/71.3, 71.1, 691–693, 713, 439, 450; 73/61.71, 61.73, 865.5, 861.41; 702/26, 702/29
See application file for complete search history.

(56) References Cited

U.S. PATENT DOCUMENTS

| 2,656,508 | A | 10/1953 | Coulter |
| 3,793,587 | A | 2/1974 | Thom et al. |
| 4,157,498 | A | 6/1979 | Johnson |
| 4,237,416 | A | 12/1980 | Zold |
| 4,760,328 | A | 7/1988 | Groves |
| 5,376,878 | A | 12/1994 | Fisher |
| 6,175,227 | B1 | 1/2001 | Graham et al. |
| 6,300,626 | B1 | 10/2001 | Brook et al. |
| 6,426,615 | B1 | 7/2002 | Mehta |
| 6,703,819 | B2 | 3/2004 | Gascoyne et al. |
| 6,959,618 | B1 | 11/2005 | Larsen |
| 7,060,992 | B1 | 6/2006 | Barney |

OTHER PUBLICATIONS

Zhang, Zheng, et al., "An electronic pollen detection method using Coulter counting principle", Atomospheric Environment 39 (2005) 5446-5453.

Jagtiani, Ashish, et al., "Detection and counting of micro-scale particles and pollen using a multi-aperture Coulter counter", Measurement Scient and Technology, 17 (2006), 1706-1714; Institute of Physics Publishing, UK.

Jagtiani, Ashish, et al., "A label-free high throughput resistive-pulse sensor for simultaneous differentiation and measurement of multiple particle-laden analytes", Journal of Micromechanics and Microengineering, 16 (2006) 1530-1539; Institute of Physics Publishing, UK.

Paper No. IMECE2006-15540; Zhe, Jiang, et al., "A Microfluidic Based High Throughput Resistive Pulse Sensor", ASME International Mechanical Engineering Congress and Exposition, Nov. 5-10, 2006, Chicago, IL.

*Primary Examiner*—Hoai-An D Nguyen
(74) *Attorney, Agent, or Firm*—Joseph J. Crimaldi; Roetzel & Andress

(57) ABSTRACT

The present invention generally relates to a method for rapidly counting micron and/or submicron particles by passing such particles through any of a plurality of microfluidic channels simultaneously with an ion current and measuring the signal generated thereby. The present invention also generally relates to a device for practicing the method of the present invention. Some embodiments can include methods and/or devices for distinguishing between and counting particles in mixtures. Still other embodiments can include methods and/or or devices for identifying and/or counting bioparticles and/or bioactive particles such as pollen.

23 Claims, 47 Drawing Sheets

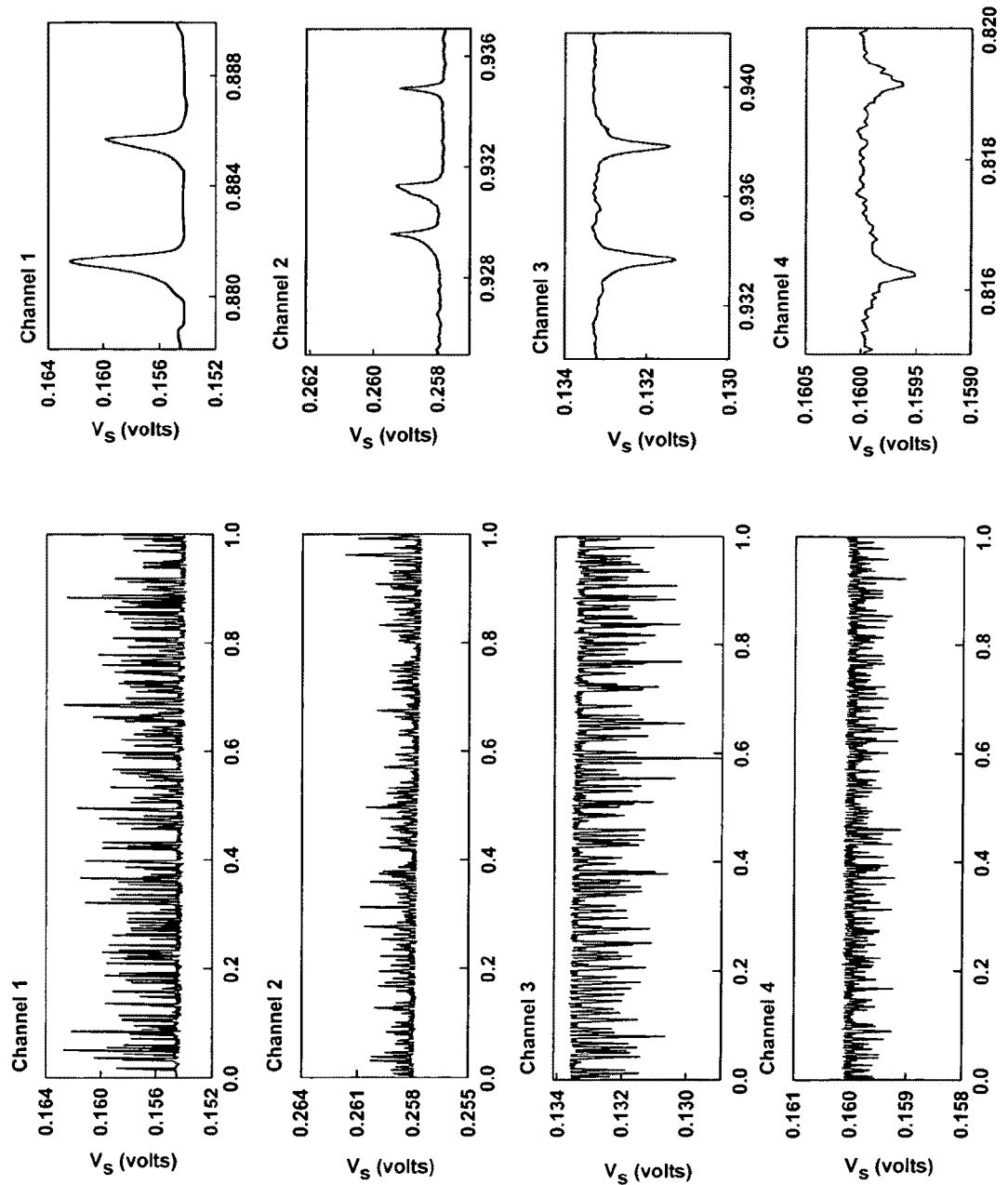

Schematic sketch of a device for Anthrax detection

Fig. 36

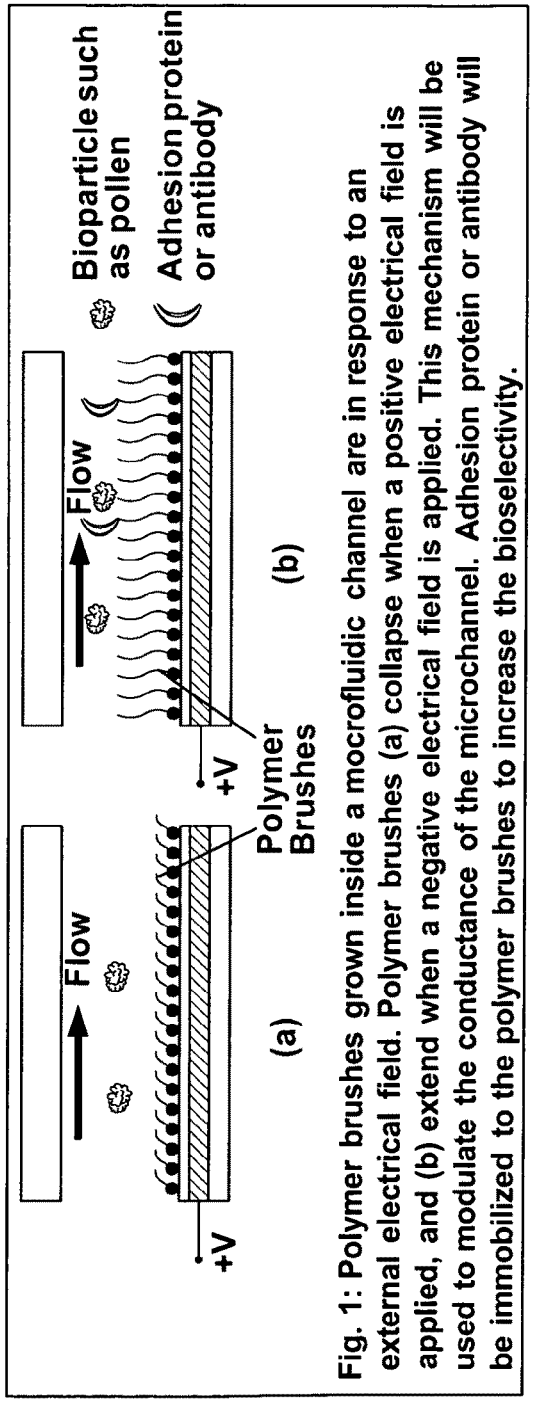

Fig. 1: Polymer brushes grown inside a mocrofluidic channel are in response to an external electrical field. Polymer brushes (a) collapse when a positive electrical field is applied, and (b) extend when a negative electrical field is applied. This mechanism will be used to modulate the conductance of the microchannel. Adhesion protein or antibody will be immobilized to the polymer brushes to increase the bioselectivity.

Fig. 41

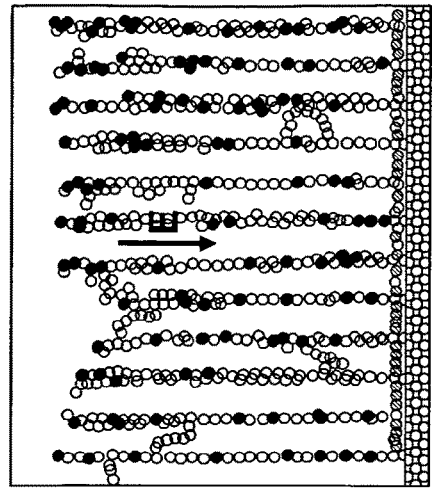

Fig. 42c

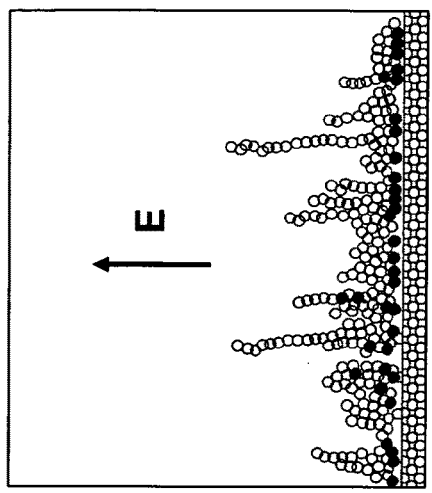

Fig. 42b

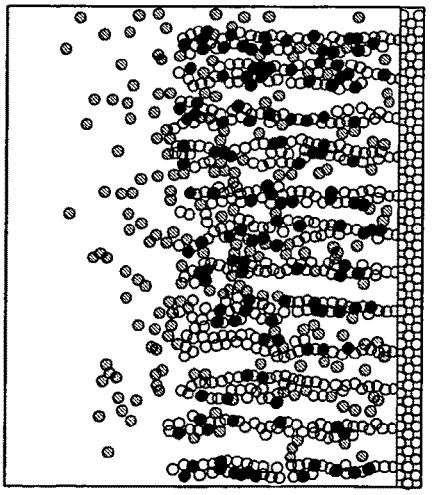

Fig. 42a

DYNAMIC MODULATION FOR MULTIPLEXATION OF MICROFLUIDIC AND NANOFLUIDIC BASED BIOSENSORS

BACKGROUND OF THE INVENTION

The present invention is generally related to a multichannel particle counting method and a device for practicing the method. Such counters can be used to count micro-scale and/or nano-scale particles and the like. Counters within the scope of the present invention generally operate by sensing changes in resistance, conductivity, conductance or the like. More particularly, as a particle passes through a channel, it disrupts the ion current therein, thus increasing the channel's resistance.

Quantitative measurements of the size and concentration of micro and nano scale particles has been accomplished using Coulter counters. A typical Coulter counter device comprising a single micropore that separates two chambers containing electrolyte solutions. When a particle flows through the microchannel, it results in the electrical resistance change of the liquid filled microchannel. The resistance change can be recorded in terms of current or voltage pulses, which can be correlated to size, mobility, surface charge and concentration of the particles. Due to the simple construction of these devices and the reliable sensing method, Coulter devices have found application in a broad range of particle analyses from blood cells to polymeric beads, DNA, virus particles and even metal ions.

One substantial disadvantage of existing Coulter counters is their low throughput efficiency, which substantially extends measurement times. Coulter counting measurement relies on particles passing through a tiny orifice (microchannel) one by one from one chamber to the other. Thus, in order to complete sampling of a small number of particle solutions, thousands of micro or nanoparticles have to pass through the orifice one by one, which could be prohibitively time consuming. For instance, one estimate shows that a sample having a particle concentration of $10^8$ particles/mL (v/v ratio 0.026%) requires 27.7 hours to complete a measurement, assuming each particle takes about 0.05 seconds to pass through the orifice, only one particle is resident in the orifice at any given time, and assuming a 0.01 mL sample volume. The measurement time is further extended as the orifice size decreases.

A variety of approaches to alleviating the time-measurement issue have been tried in the art. For instance, electroosmosis and electrophoresis have been applied to drive particles and electrolyte fluids. However, both methods have fallen short. Particularly, in order to obtain a sufficient fluid velocity, a strong external electric field must be applied leading to high power consumption, which is not practical for most biological applications. Furthermore, electroosmosis and electrophoresis only drive charged particles. Thus, if the particles are only slightly charged or neutral, electric forces are too weak to substantially shorten measurement time. Accordingly, there is a deficiency in the art in that it lacks a high throughput particle counting method and device, which is compatible with biological particles.

The present invention overcomes the challenges and deficiencies of the prior art by providing a particle counting method and device having a plurality of orifices, which are capable of counting particles in parallel with one another. Furthermore, such systems are compatible with biological particles inasmuch as it circumvents the need for electrophoretic or electroosmotic fields. Thus, the present invention fills a substantial gap in the art.

SUMMARY OF THE INVENTION

The present invention is generally directed to a multichannel particle counting device comprising a plurality of microfluidic channels dividing a first reservoir and a second reservoir and maintaining fluid communication therethrough; each microfluidic channel including a control electrode, wherein each control electrode is substantially electrically isolated from every other control electrode; and each control electrode encoded to respond to a specific frequency; the first and second reservoirs including one set of detection electronics including a first electrode in electrical communication with a power supply and a second electrode in electrical communication with a measuring circuit; the one set of detection electronics being the collector for each signal from each control electrode and having a means to deconvolute the collected signals; the reservoirs containing an electrolyte solution containing particles to be counted; and a means for creating a net fluid flow of electrolyte from one reservoir to the other reservoir through the microfluidic channels.

A method for rapidly counting particles comprising the steps of charging one reservoir of the foregoing device with an electrolyte solution containing at least one particle to be measured; applying a voltage across the one set of detection electronics; allowing the particles to migrate from one reservoir to the other through the plurality of microfluidic channels; dynamically modulating the microfluidic channels; the one set of detection electronics detecting the signals generated as particles pass through the plurality of microfluidic channels; deconvoluting the signals detected; correlating the signals to the number of particles passing through each microfluidic channel; and counting the deconvoluted signals.

BRIEF DESCRIPTION OF THE DRAWINGS

FIG. 21 is a set of plots showing (a) data from four sampling resistors, and (b) magnified voltage pulses;

FIG. 36 is a mail sorting embodiment for detecting Anthrax spores on mail items;

FIGS. 39(*b*) and 39(*c*) are schematic views of the actuator embodiment of FIG. 39(*a*), wherein the actuator is shown to modulate flow through the fluid microchannel;

FIG. 41(*a*)-(*b*) is a diagram of polymer brushes;

FIG. 42(*a*)-(*c*) provides a side view of grafted polymer brushes in the (a) equilibrium state, (b) collapsed state and (c) erect state;

DETAILED DESCRIPTION OF THE INVENTION

The present invention generally relates to a method for rapidly counting particles using a plurality of orifices for simultaneously sensing particles. The present invention also generally relates to a device for practicing the method of the present invention.

The method of the present invention includes providing a plurality of orifices that are capable of passing particles to be counted, wherein the diameter of the orifices is such that they can pass the particles one at a time, i.e., in single file. In general the orifices separate two electrolyte solutions, wherein one solution is in electrical communication with a cathode and the other is in electrical communication with an anode. When a voltage is applied across the cathode/anode pair, an ion current flows through the orifices. Thus, a signal is generated when at least one particle enters at least one orifice, thereby obstructing the flow of ion current and raising resistance. The signal can be read conveniently in terms of current or voltage. Furthermore, the present invention simultaneously detects particles in a plurality of orifices. Since these orifices are in a parallel electrical relationship, the signals generated thereby are multiplexed, and thus must be deconvoluted. The "Hardmard/Fourier Transformation" makes it possible to deconvolute the signal of the multiplexed particle counting device of the present invention.

Membranes within the scope of the present invention can be fabricated from a wide variety of materials including without limitation organic polymers such as polymethyl methacrylates, polycarbonates, polyimides, polyphenols, chlorinated polyolefins, and the like. Additionally, membranes within the scope of the present invention can be fabricated from silicon, n-type silicon, p-type silicon, and the like. Membrane materials within the scope of the present invention should be stable under ordinary usage conditions, and should be capable of forming the pores and other micro and/or nano structures comprising the present invention.

Electrodes within the scope of the present invention can be fabricated from any of a variety of materials including without limitation, Ag|AgCl, platinum, and graphite electrodes.

Any of a variety of electrolytes can be used as the electrolyte of the present invention. In general, acceptable electrolytes are compatible with the selected electrode(s), and comprise cations and anions having similar mobilities. For instance, when the selected electrode is Ag|AgCl acceptable electrolytes include, without limitation, KCl and NaCl.

Figure 1:
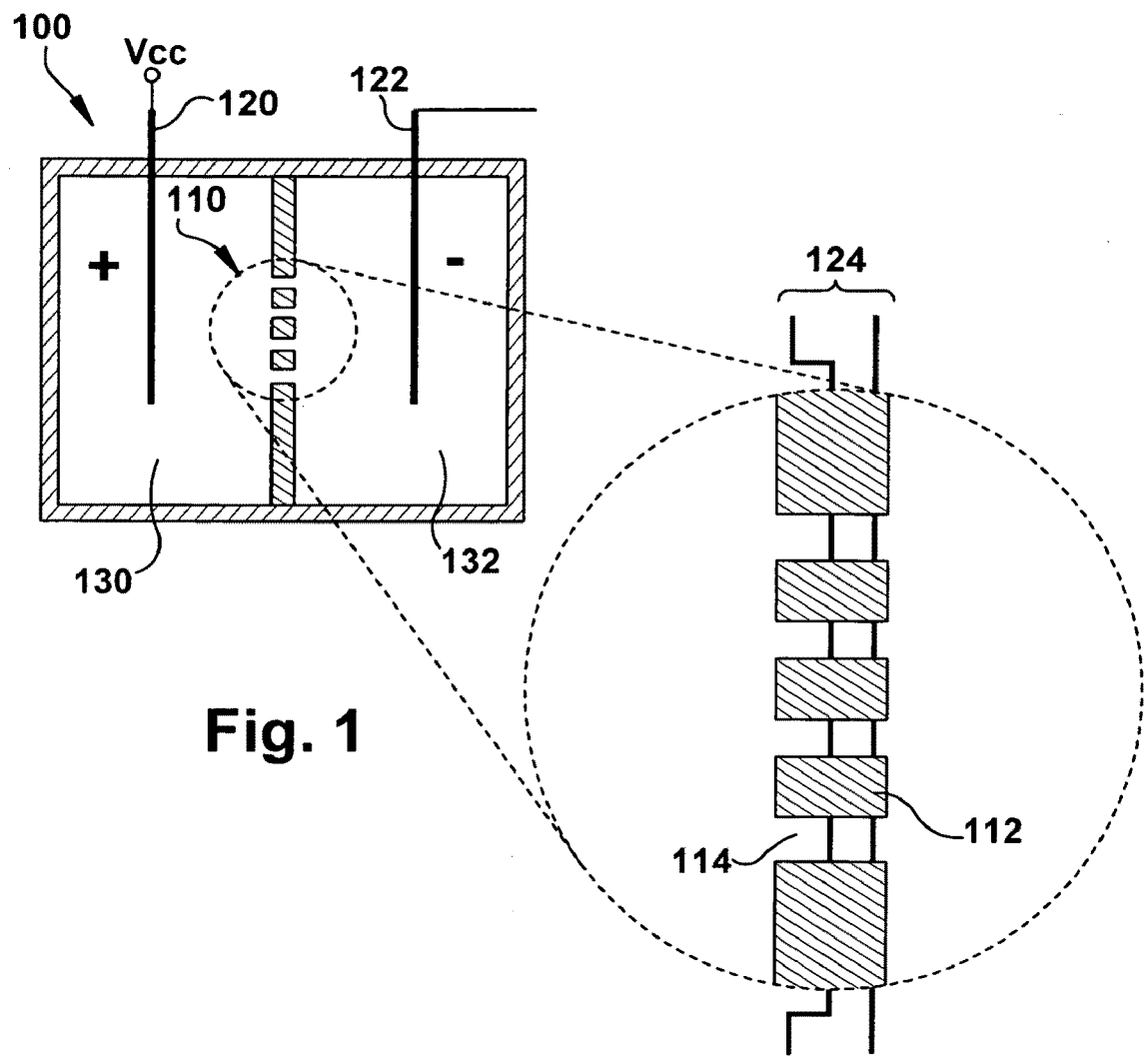
FIG. 1 is a schematic showing the a multichannel particle counting device.

An example of the present invention is shown in FIG. 1. Four microchannels 110 are formed using insulating blocks 112 (i.e., isolation blocks). Each individual microchannel 114 (i.e., orifice) includes a control electrode 124, which carries out control and measurement functions the nature of which will become apparent in the following paragraphs. Furthermore, each control electrode 124 is insulated from every other control electrode 124 so that sensing events occurring in one microchannel 114 do not affect sensing events in other microchannels 114. The plurality of microchannels 110 separate two electrolyte solutions contained in separate reservoirs 130, 132. One reservoir 130 is in electrical contact with a cathode 120 and the other is in electrical contact with an anode 122. When a suitable voltage (e.g., 2.7 V) is applied across the electrodes an ion current is generated, which runs through the plurality of microchannels 110. In this embodiment, either the cathode 120 or anode 122 is in electrical communication with a power supply, while the other electrode is in electrical communication with a measurement circuit. Signals are generated when one or more particles enter one or more microchannels 114 thereby raising the resistance to ion current therein and causing a consequent increase in voltage. Each microchannel causes its own voltage and/or current signal, which superpositions with the signals of each other microchannel.

Figure 2:
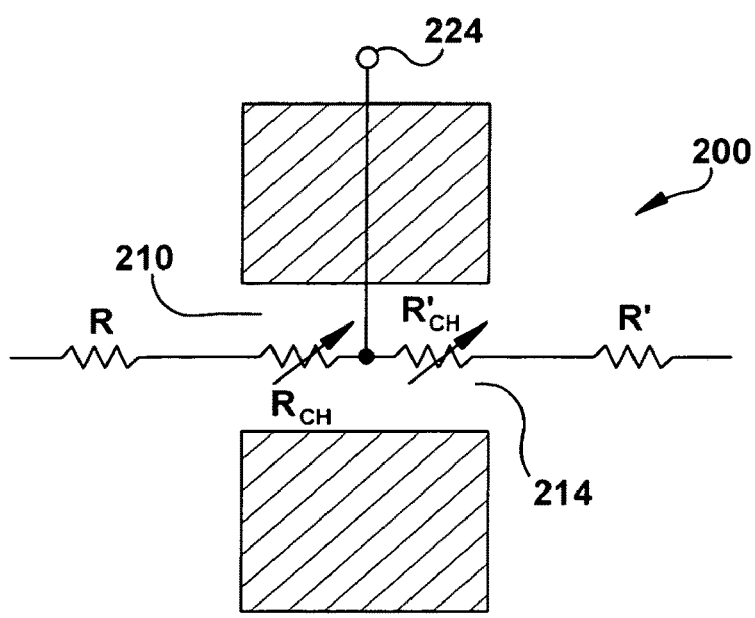
FIG. 2 is a diagram pictorially showing the resistance of each sensing element. Note that R and R' (i.e., the resistances of the electrolytes outside the channel) can be neglected when compared to the channel resistances $R_{ch}$ and $R'_{ch}$.

FIG. 2 shows the equivalent resistance model of an individual channel. The resistances R and R' are that of the fluids in the reservoirs between the cathode (or anode) and the channel. $R_{ch}$ is the channel resistance and its value is a function of channel diameter, length and ion solution in the channel. When a particle enters the channel 214 it displaces some ions and from the channel 214, which results in an increase in the channel resistance. The control electrode 224 is positioned in the middle so that the channel resistance is split into two resistances $R_{ch}$, $R'_{ch}$. Thus, the control electrode 224 forms a node with the two resistances.

Figure 3:
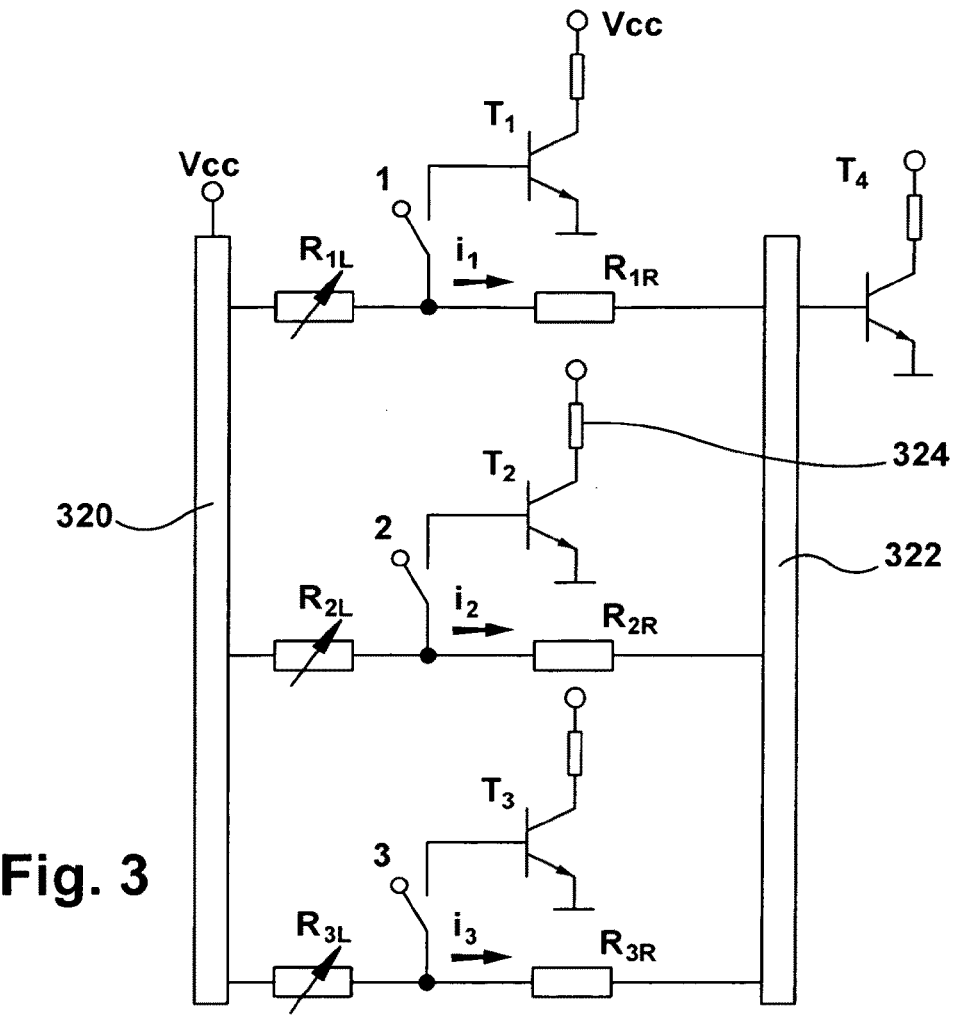
FIG. 3 is an electrical schematic showing an example embodiment of the present invention comprising a 3-channel multiplexing particle counting device.

In order to detect a particle passing through a particular channel the response of each individual channel needs to be obtained in the form of a current or voltage pulse. However, since all of the channels are in electrical communication with the electrolyte solutions the signal sensed by the measurement circuit is the sum of the signals from all channels at any given time. The present invention is able to deconvolute the raw superposition of signals, and records the signals of each individual channel. FIG. 3 is a schematic of a measurement circuit for a 3-channel device. $V_{cc}$ is kept at a high voltage level, such as from about 1 V to about 4 V (e.g., 2.7 V). Each control electrode 324 is connected to a transistor (T1, T2, or T3). The measurement circuit has a transistor (T4) in common emitter configuration. T4 is always kept on, so that the voltage at node 4 is kept at approximately 0.7 V. If T1 is on, the voltage at node 1 is 0.7 V, so that there is no current input to transistor 4 from channel 1. Because of the measurement configuration, the output of the transistor T1 is representative of the resistance of channel 1 ($R_{1L}$). Similarly, if T2 and T3 are open, we could measure the output of T2 and T3, which are representative of the resistances of channel 2 and 3 ($R_{2L}$, $R_{3L}$) respectively. On the other hand, if T1 is off then current $i_1$, which is representative of resistance ($R_{1L}$), will be one input to T4 or the sum of any channels selected. Similarly, if T2 and T3 are off then currents $i_2$ and $i_3$ will be the input to transistor T4. Therefore, by controlling the on/off state of control electrodes it is possible to turn the current on and off from each channel and measure the sum of the responses of any selected channels.

The raw signal obtained from the measurement circuit is deconvoluted according to the following process. The on/off states of the four control electrodes (S1, S2, S3) are controlled with a pseudorandom sequence. The current i4, measured from transistor 4, is the sum of the current through selected channels. A channel is selected when its transistor is off. Thus, if a control electrode is off the current through the channel will be input Transistor 4.

TABLE 1

| S1  | S2  | S3  | I4           |
|-----|-----|-----|--------------|
| OFF | OFF | OFF | i1 + i2 + i3 |
| OFF | OFF | ON  | i1 + i2      |
| ON  | OFF | OFF | i2 + i3      |

Desired current combinations can be measured (Matrix Y) by setting the desired switching sequence (matrix S) of control electrodes. For the sequence code in Table 1, the sequence matrix S can be written as:

$$S = \begin{pmatrix} 1 & 1 & 1 \\ 1 & 1 & 0 \\ 0 & 1 & 1 \end{pmatrix}$$

The Hardmard transformation can be used to find the current response of individual channels since the switching sequence is known. Therefore the current response of individual channel X, can be calculated as the dot product of matrix Y and the inverse of matrix S:

$$X = S^{-1} \cdot Y$$

Furthermore, four combinations are needed in order to solve this equation because it entails four unknown currents.

In a Hardmard Transformation, the mean square error is reduced by a factor of $(n+1)^2/4n$ indicating that the signal-to-noise ratio is increased by a factor of $(n+1)/4n^{1/2}$. Thus, as the number of channels increases, the signal-to-noise channel improves.

One embodiment of the present invention comprises a device 400 for quantitatively detecting the concentration and particle size of pollen in air. For instance, the multiplexed particle counting device 400 of the present invention can be outfitted with an air sampling device 410 according to FIG. 4. As shown, a sampling bottle 412 has an air sampling port 414, which is vented to the atmosphere. Furthermore, it is fitted with an electrolyte intake port 420, and fed there through by an electrolyte reservoir 422. Additionally, the sample bottle has two output ports 430, 440. One is a vapor line 440, which is in fluid communication with a vacuum pump 442, so that when the vacuum pump 442 operates gas is drawn from the sample bottle 412. The other output port is a liquid output 430, which carries electrolyte solution to the particle counting portion 432 of the device 400. Optionally, the airborne pollen sampling device can additionally include a component 434 for adding antibodies to the electrolyte solution before it reaches the particle counting portion 432 of the device 400.

Figure 4:
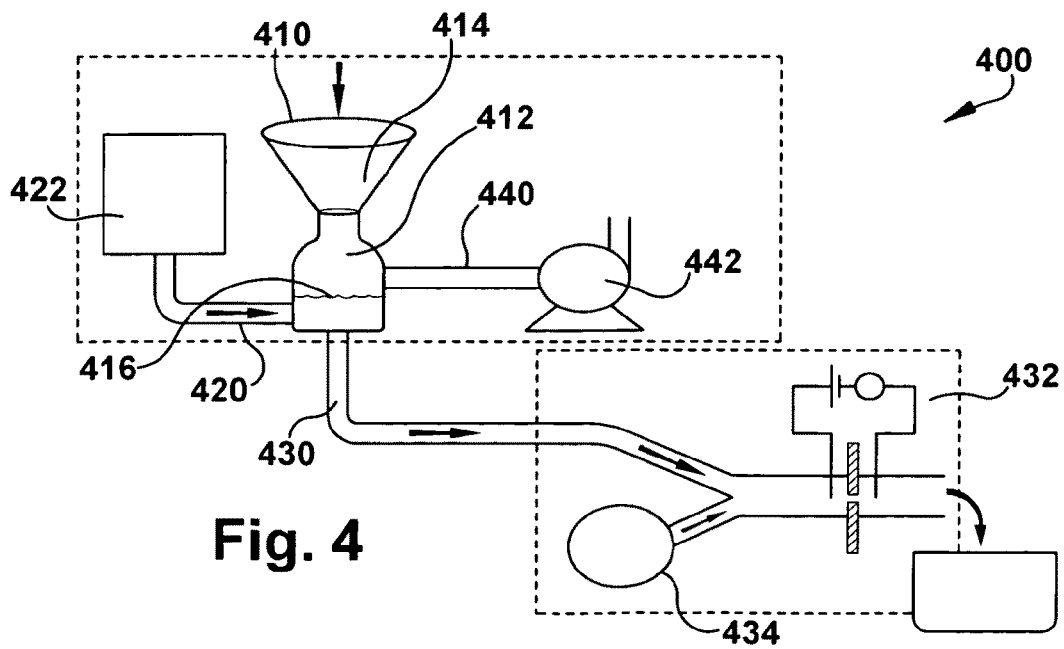
FIG. 4 is a diagram of a airborne pollen sampling device fitted with the multichannel particle counting device of the present invention.

This system 400 operates as follows. The vacuum pump 432 draws air into the sample bottle 412 through air intake port 414. Any particles that may be present impact the liquid electrolyte surface 416 and are deposited therein while the gas is drawn out of the sample bottle 412 through the vacuum pump 442. The particle-laden electrolyte solution then travels through the electrolyte output port 430 and down the liquid line leading to the particle counting portion 432 of the device 400, where the particles are then counted. Furthermore, the liquid can be induced to flow through the counting portion 432 by maintaining a positive pressure on the sampling side of the counting portion 432. For instance, as shown in FIG. 4, an electrolyte reservoir 422 is included, which can be elevated so that a gravity-induced pressure gradient is created, which drives liquid flow.

Another embodiment of the present invention comprises a device for detecting the concentration and particle size of chemical and/or biological warfare agents such as weaponized (i.e., aerosolized) anthrax. In still another embodiment, the present invention comprises a device for detecting toxins, impurities, or microbial or viral contaminants in waters, such as drinking water. Still another embodiment of the present invention comprises a device for rapidly counting blood cells, and/or comparing the number of red blood cells to white blood cells.

Figure 5:
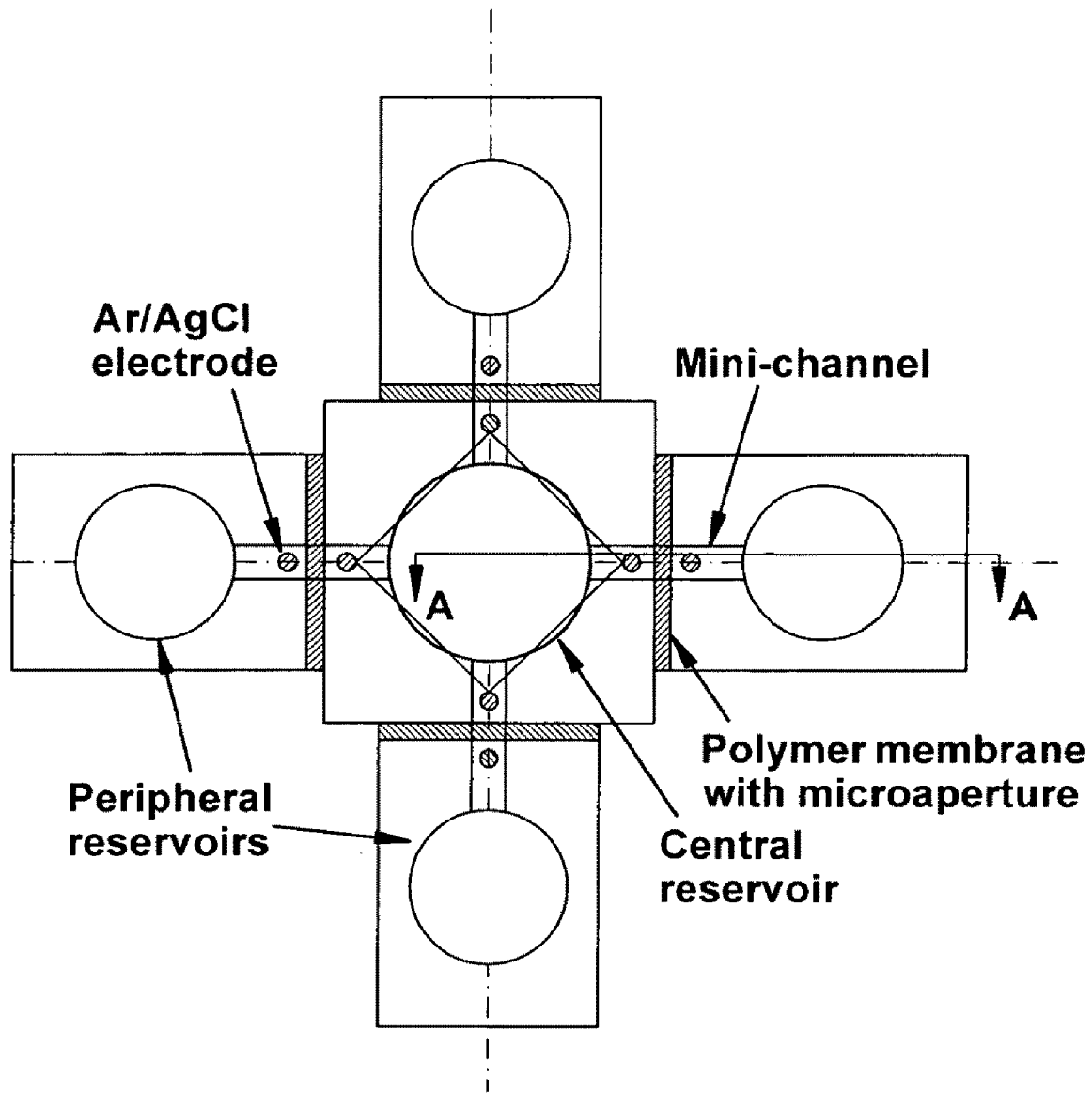
FIG. 5 is a drawing of a multi-aperture embodiment for microparticle detection.

I. Pollen Detection Embodiments:

One non-limiting embodiment of the present invention comprises a multi-aperture Coulter counter, as shown in FIG. 5. This embodiment comprises four peripheral reservoirs and a central reservoir. Each peripheral reservoir is connected to the central reservoir through a miniature channel. According to this embodiment, a micro-scale aperture in the middle of each mini-channel is used for sensing.

In this embodiment, the central reservoir and one half of each of the four mini-channels can be formed by drilling holes in a polymethyl methacrylate (PM) block. Furthermore, each of four additional PM blocks can be drilled to form the other half of a mini-channel and a peripheral reservoir. After the holes are drilled, the PM blocks can be cleaned, for example, with ethyl alcohol and/or sonicated in an ultrasound bath. The microapertures are fabricated by piercing four polymer membranes with a heated micro needle. The membranes can be examined under a high-precision microscope, and the microapertures are found to have diameters between 90 μm and 110 μm, as shown in Table 2.

TABLE 2

|  | Aperture 1 | Aperture 2 | Aperture 3 | Aperture 4 |
|---|---|---|---|---|
| Diameter D | 110 μm | 110 μm | 90 μm | 100 μm |

The nominal thickness of the membrane is about 100 μm. However, due to the hot-piercing microaperture fabrication process, the length of each microaperture might change considerably from the nominal thickness of the membrane, which is determined later.

According to this non-limiting embodiment, the first channel can be formed by applying epoxy to one mini-channel side of the PM block with the central reservoir, and to the mini-channel side of one of the PM blocks with a peripheral reservoir. A membrane can be placed between the two blocks, carefully aligned so that its microaperture is centered between the two halves of the mini-channel. The blocks are then clamped together for two to five hours, or until the two blocks and the membrane are firmly attached. A pair of 1 mm holes, located 5 mm away from the membrane on both sides, can be drilled in the PM blocks. The Ag/AgCl electrodes are placed on both sides of the membrane through the 1 mm holes. Then epoxy can be applied to fix the electrodes and seal the mini-channel. The same procedure is repeated for the other three peripheral blocks to form a four-aperture sensor. One of ordinary skill in the art will readily appreciate that a variety of alternative materials, fabrication techniques, and electrodes can be used to form a device within the scope of the present invention.

Figure 6A:
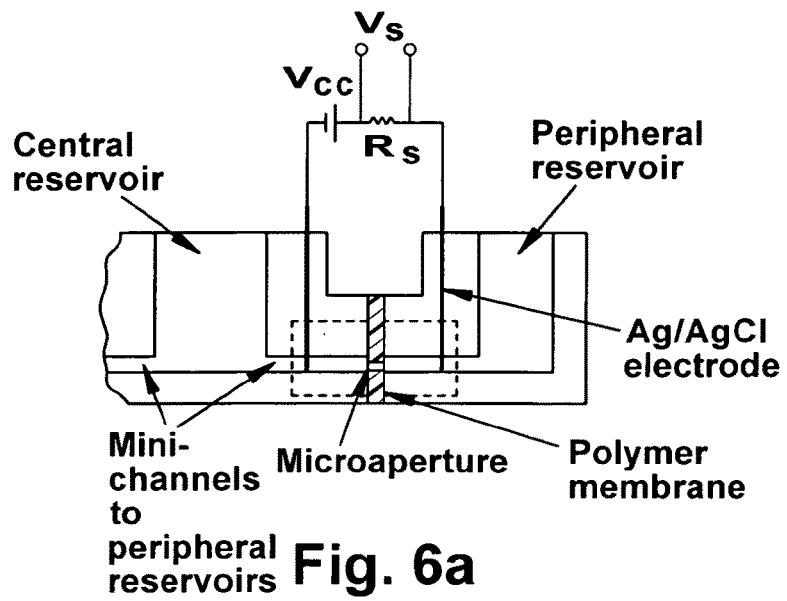
FIG. 6 (a) is a schematic front view of a single channel of a multi-aperture embodiment, (b) is a magnified view of a single channel; and (c) is a drawing of an circuit equivalent of a single channel.
Figure 6B:
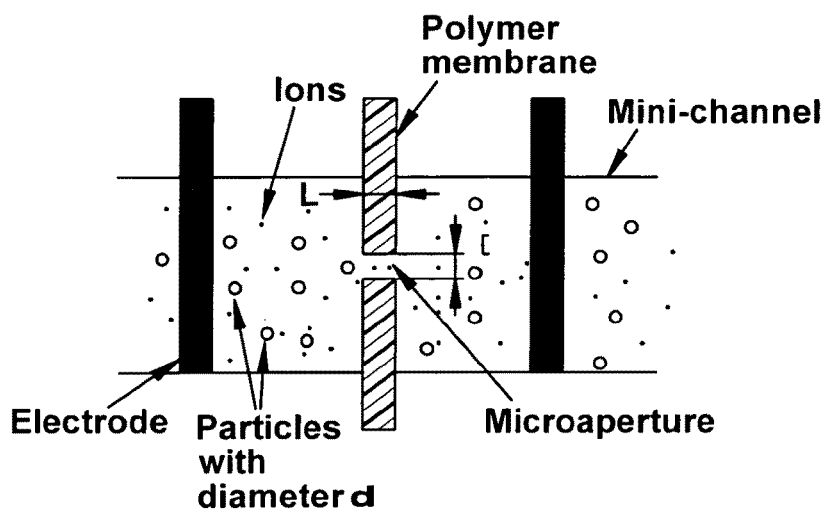
Figure 6C:
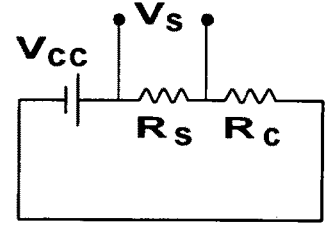

FIG. 6(*a*) shows the sectioned front view of a single sensing channel (across the A-A line in FIG. 5), along with the measurement setup. $R_s$ is a known external sampling resistor. The Ag/AgCl electrodes placed on both sides of the membrane are used to apply a constant DC voltage VCC across the channel. FIG. 6(*b*) shows a magnified drawing of the mini-channel, microaperture and electrodes. The measurement architecture of one sensing channel is electrically equivalent to the circuit in FIG. 6(*c*), where $R_c$ is the resistance of the electrolyte-filled microaperture.

As a particle passes through the microaperture there is a change in the electrical resistance of the aperture. This leads to a change in the voltage VS across the measurement resistance $R_s$. From the circuit model in FIG. 6(*c*), the relative change in the resistance of the microaperture is given by:

$$\frac{\delta R_c}{R_c} = \frac{(V_s - V_s')V_{cc}}{(V_{cc} - V_s)V_s'} \quad (1)$$

where $\delta R_c$ is the change in aperture resistance, $R_c$ is the resistance of the aperture when no particles are present, $V_{CC}$ is the applied DC voltage, $V_s$ is the voltage measured across the sampling resistor when the aperture is filled only with electrolyte solution and $V_s'$ is the peak voltage measured across the sampling resistor as a particle passes through the microaperture.

For a microaperture with length L and diameter D (see FIG. 6(*b*)), the change in resistance as a particle passes through it is given by:

$$\frac{\delta R_c}{R_c} = \frac{d^3}{L'D^2}\left[\frac{D^2}{2L^2} + \frac{1}{\sqrt{1+\left(\frac{D}{L}\right)^2}}\right] \quad (2)$$

where d is the diameter of the particle, L' is the corrected aperture length to account for fabrication artifacts, which equals L+0.8 D. Equation 2 holds when $(d/D)^3 < 0.1$, as is the case in this and other embodiments. Thus, the particle diam eter can be calculated from the relative change in resistance according to:

$$d = \sqrt[3]{\frac{\frac{\delta R_c}{R_c}L'D^2}{\frac{D^2}{2L^2} + \frac{1}{\sqrt{1+\left(\frac{D}{L}\right)^2}}}} \quad (3)$$

Figure 7:
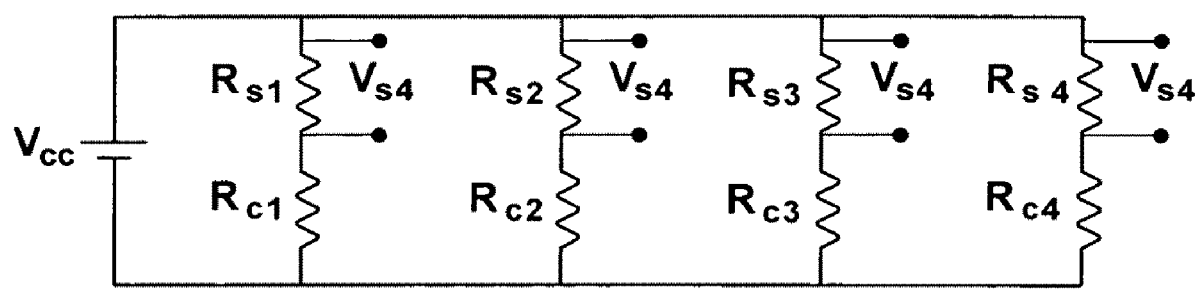
FIG. 7 is a equivalent electric circuit of a four-aperture embodiment.
Figure 8A:
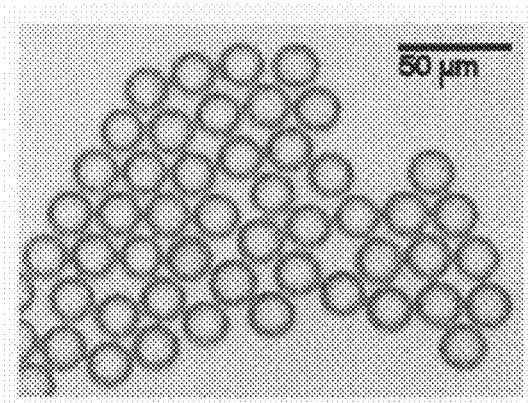
FIG. 8 is a set of photomicrographs of (a) 20 µm polymethacrylate particles, (b) 40 µm polymethacrylate particles, (c) Juniper *Scopulorum* pollen, and (d) Cottonwood pollen.
Figure 8B:
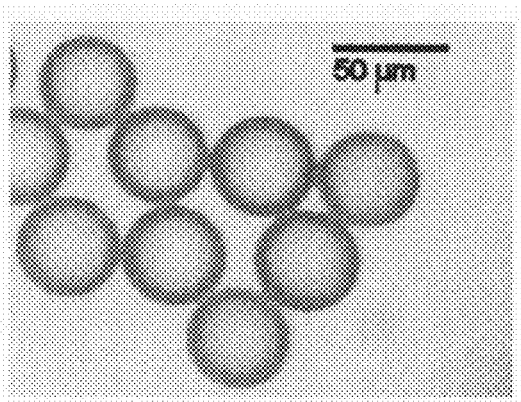
Figure 8C:
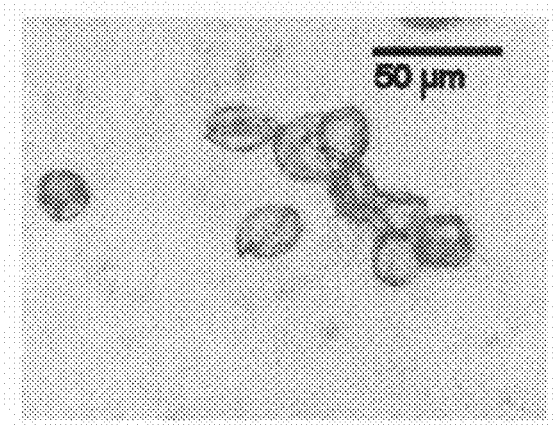
Figure 8D:
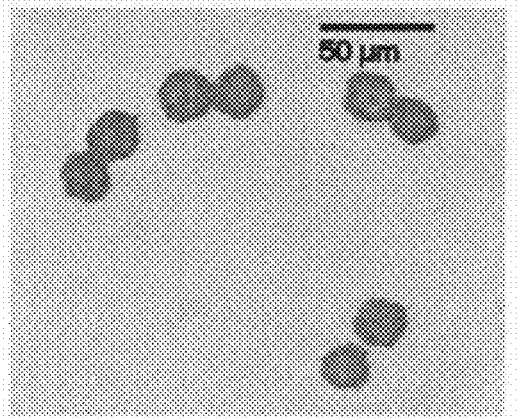

In one embodiment, a four-aperture sensor has four sampling resistors $R_{s1}$, $R_{s2}$, $R_{s3}$ and $R_{s4}$ across which four voltage measurements $V_{s1}$, $V_{s2}$, $V_{s3}$ and $V_{s4}$ are made. The overall measurement setup for the four-aperture sensor is electrically equivalent to the circuit shown in FIG. 7, where $R_{c1}$, $R_{c2}$, $R_{c3}$ and $R_{c4}$ are the resistances of the four microapertures. According to some embodiments, the four negative electrodes are electrically shorted in the central reservoir to ensure that each channel sees the same constant DC voltage $V_{CC}$. In this way, a variation in resistance in one microaperture does not cause voltage variation (i.e., crosstalk) in any other channel.

Example of Pollen Detection Embodiment:

One working example of the present invention is set forth as follows. Four types of micro-scale particles are chosen for a test of a multi-aperture sensor embodiment. They are polymethacrylate (PM) particles with diameters of 40 μm and 20 μm, Rocky Mountain Juniper (Juniper *Scopulorum*) pollen, and Cottonwood pollen. All particles are obtained from Sigma Aldrich, Inc. PM particles are chosen because they are commercially available and have well-characterized properties. The diameters of the pollen particles are determined using high-resolution optical microscopy, and range from 17.5 μm to 22.5 μm for the Juniper pollen and 20 μm for Cottonwood pollen. FIG. 8 shows photomicrographs of the four types of particles.

For experiments involving the polymethacrylate (PM) particles, 40 μm and 20 μm particle solutions can be prepared by diluting 0.1 mL of the original solution, which has 10% solid content, in 2 mL and 10 mL of deionized water, respectively. The estimated particle concentrations of the 40 μm and 20 μm particle solutions are approximately $1.2 \times 10^5$ mL$^{-1}$ and $2 \times 10^5$ mL$^{-1}$, respectively. For experiments involving Rocky Mountain Juniper pollen particles, a solution can be prepared by diluting 0.1 mL of the original pollen particles in 7 mL of deionized water.

In each example, 1 mL of the prepared particle solution is added to the central reservoir using a microsyringe. The liquid in the central reservoir is agitated to make sure that the particles are well dispersed. A gravity-induced pressure difference is created by placing the central reservoir at a higher level than the peripheral reservoirs. Pressure-driven flow forces the particle solution to move towards the peripheral reservoirs through the four sensing apertures.

The sampling resistor for each channel is $R_s = 100$ kΩ, and the applied voltage across the electrodes of each channel is $V_{CC} = 3$ V. The entire measurement architecture is placed in a Faraday cage to reduce and/or control noise. As the particles pass through the microapertures, voltage pulses across all sampling resistors can be recorded simultaneously using, for example, a National Instruments NI-6220 data acquisition board. The voltages can be monitored in real time using, for example, LabView software with a sampling frequency of 20 kHz. The data obtained are converted to relative resistance change ($\delta R_c/R_c$) using Equation (1). This relative change is used to estimate the particle diameter (i.e., using Equation (3)). Particle concentration can be estimated by counting the number of resistive pulses during a selected time period.

Figure 9:
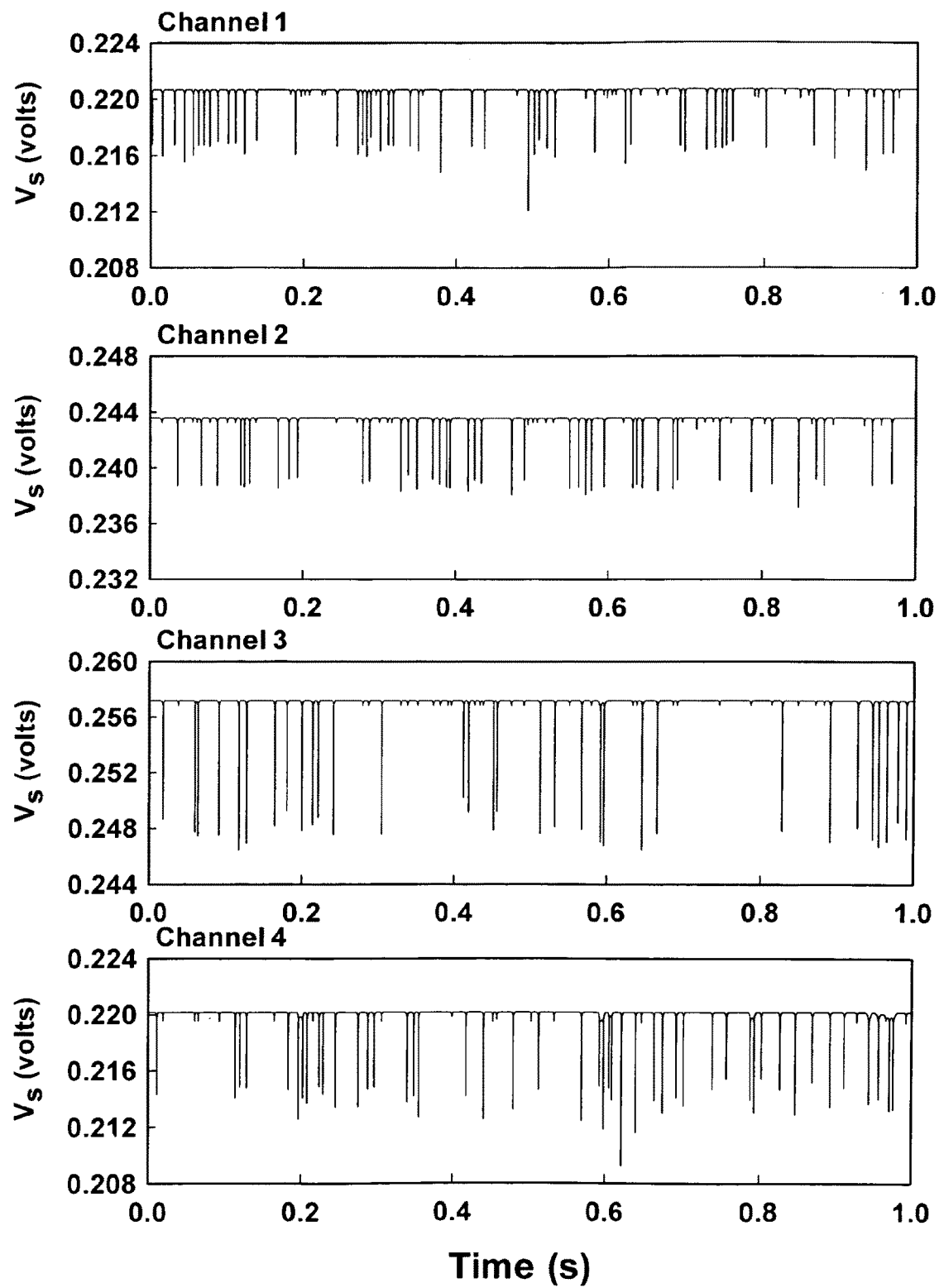
FIG. 9 is a set of four voltage traces obtained from four different sampling resistors in response to 40 µm PM particles.
Figure 10:
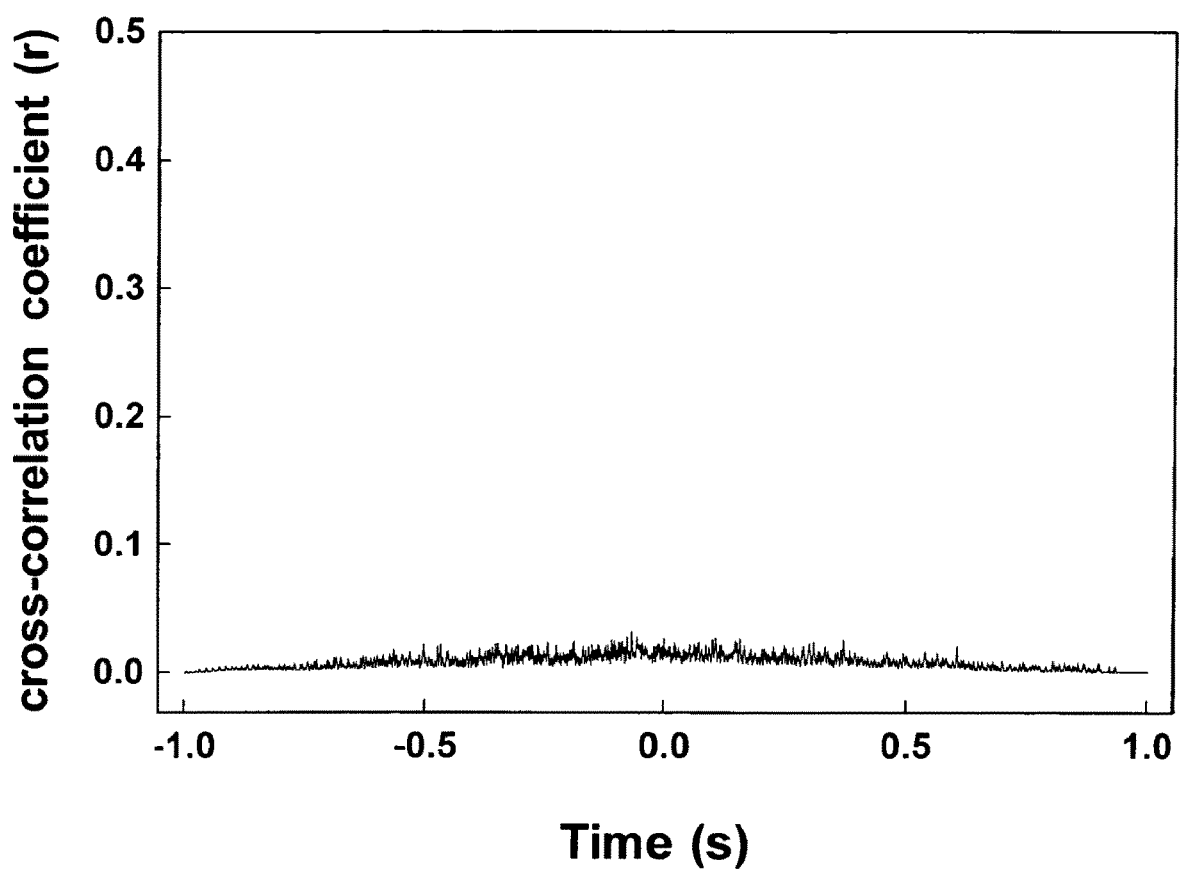
FIG. 10 is a graph showing typical results of a cross-correlation analysis performed on 40 µm PM particles.

Typical voltage traces resulting from the foregoing example are shown in FIG. 9. Pulses are recorded during a selected time period of one second. A typical result of a cross-correlation analysis performed on the signals from a pair of channels is shown in FIG. 10. The cross-correlation coefficients between channels are less than 5%, indicating negligible correlation among the pulses in different channels. This indicates that the four sensing apertures are able to simultaneously generate voltage pulses and count particles with negligible crosstalk among channels. Notably, different channels have different base voltages ($V_s$). This is primarily because the base resistances of the four microapertures ($R_{c1}$, $R_{c2}$, $R_{c3}$ and $R_{c4}$) differ due to fabrication artifacts.

Figure 11:
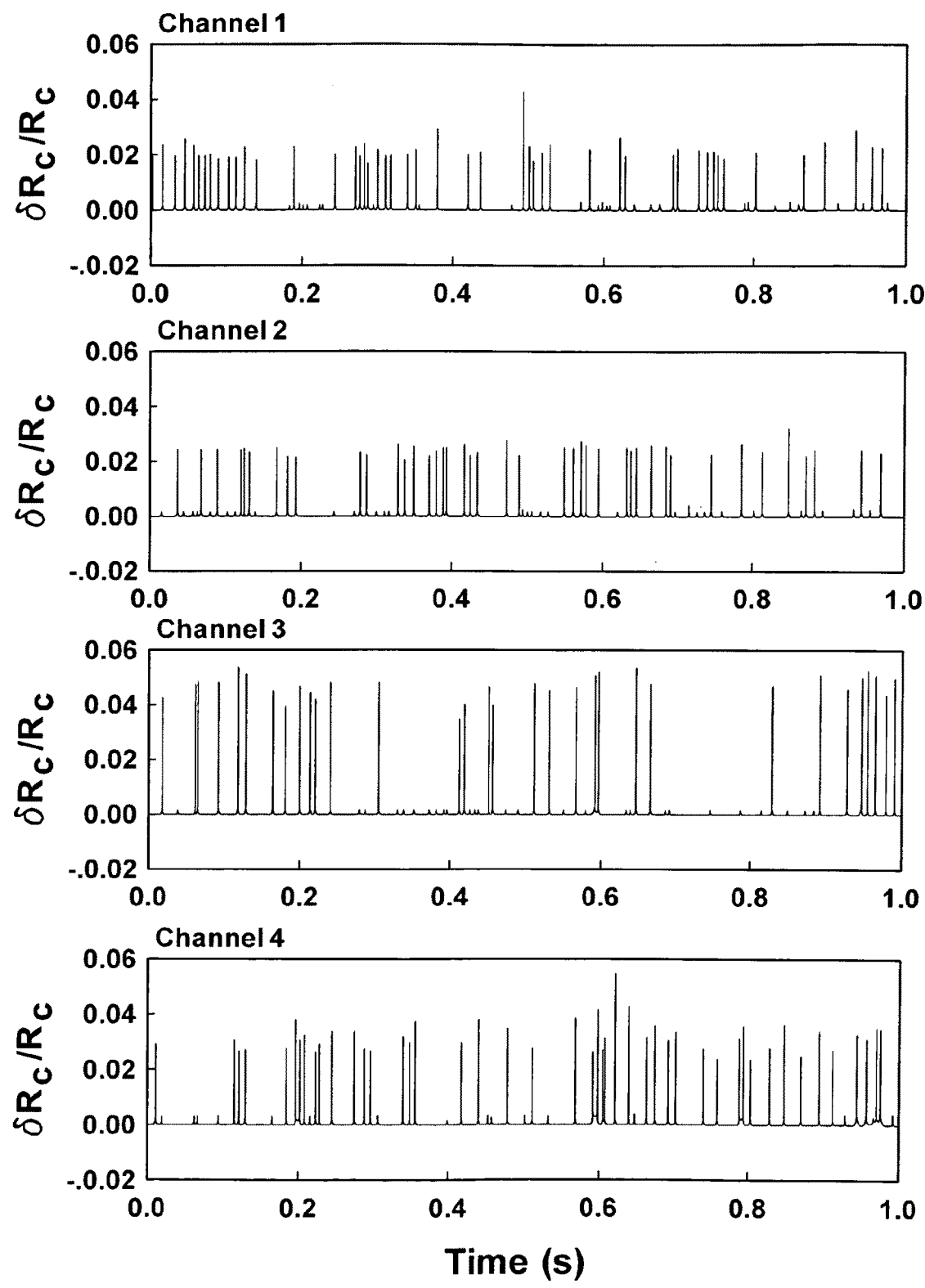
FIG. 11 is a set of four plots showing relative resistance of four sensing microapertures as a function of time, wherein each pulse corresponds to a single particle.
Figure 12:
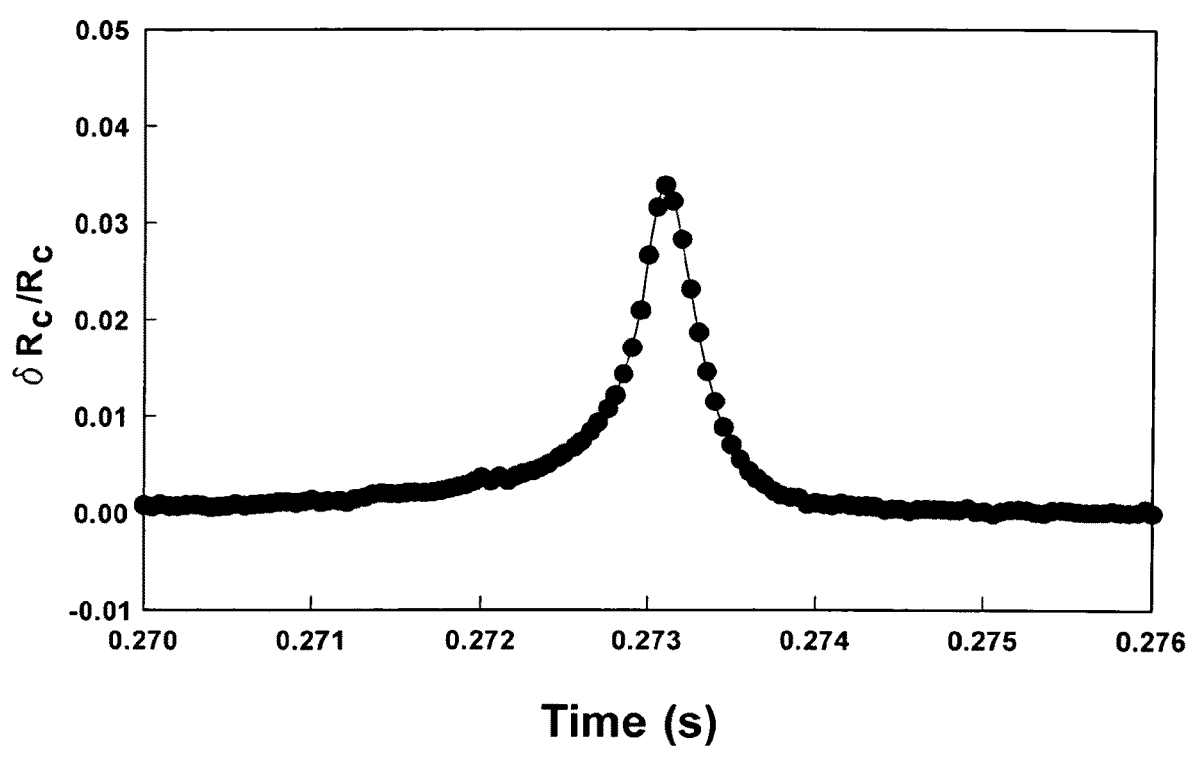
FIG. 12 is a typical resistive pulse resulting from a 40 μm PM particle passing through a microaperture.

The ratio of the resistance change ($\delta R_c/R_c$) for each microaperture, calculated using Equation (1), is plotted as a function of time in FIG. 11. FIG. 12 shows a more detailed view of a typical pulse for a 40 μm polymethacrylate particle from FIG. 11. It can be seen that the duration of the pulse due to the particle passing through the aperture is about 2 ms. Hence the average speed of a particle traveling through the channel is approximately 0.05 ms$^{-1}$. This is about the same as the velocity of the fluid flow. The average relative change in resistance is used to calibrate the length of each aperture using Equation (2). This calculation assumes that the aperture diameter measurement is accurate. The calibration results are shown in Table 3.

TABLE 3

| | Aperture 1 | Aperture 2 | Aperture 3 | Aperture 4 |
|---|---|---|---|---|
| Calibrated Length (L) | 173 μm | 153 μm | 118 μm | 127 μm |

Figure 13:
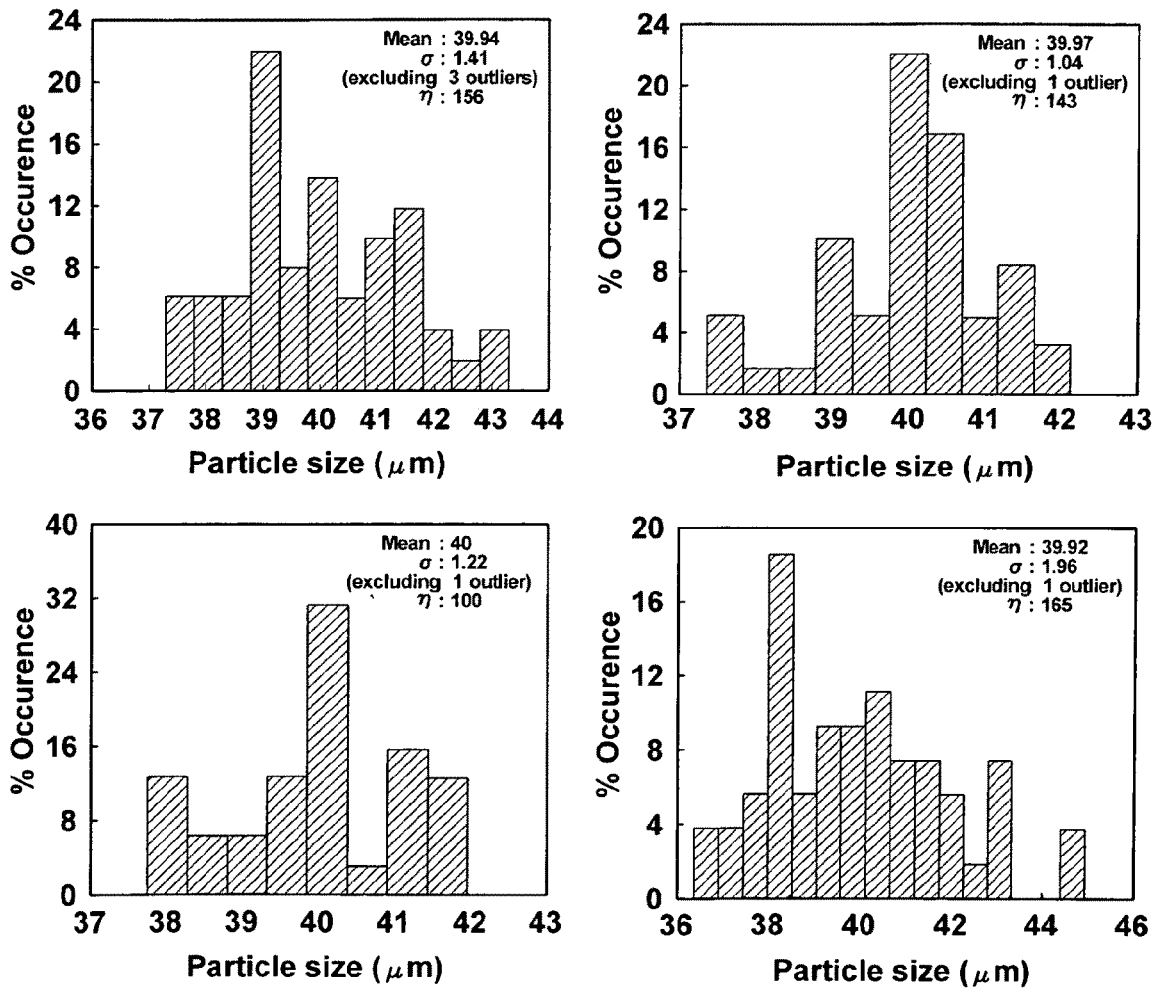
FIG. 13 is a set of four histograms showing particle size data obtained from each of four channels of the four-channel embodiment.

The calibrated aperture length can be used to calculate particle diameter using Equation (3). FIG. 13 shows a histogram of estimated particle size, along with the average size, standard deviation (σ) and number of particles (n) for each channel. The estimated particle diameters lie between about 37.28 μm and 43.25 μm (39.94±1.41 μm) for channel 1, between about 37.73 μm and 42.06 μm (39.97±1.04 μm) for channel 2, between about 37.78 μm and 41.9 μm (40±1.22 μm) for channel 3 and between about 36.44 μm and 44.92 μm (39.92±1.96 μm) for channel 4. The manufacturer specifies the actual diameter of the particles to be 40±0.8 μm. The measurement error in particle size is approximately within the overall uncertainty error range. The differences are likely due to the uncertainty of the microaperture dimension, electronic noise and the off-axis position when a particle passes through the microaperture.

The concentration of the particles in the four channels can be calculated from the number of peaks during a one second period as shown in FIG. 11. According to this example, the concentrations are found to be $1.09 \times 10^5$ mL$^{-1}$, $0.95 \times 10^5$ mL$^{-1}$, $1.04 \times 10^5$ mL$^{-1}$ and $1.12 \times 10^5$ mL$^{-1}$ for channels 1, 2, 3 and 4, respectively. The measured particle concentration in each channel is slightly lower than the estimated particle concentration, which is about $1.2 \times 10^5$ mL$^{-1}$. This is possibly because some PM particles are deposited onto the substrate during the experiments.

Figure 14:
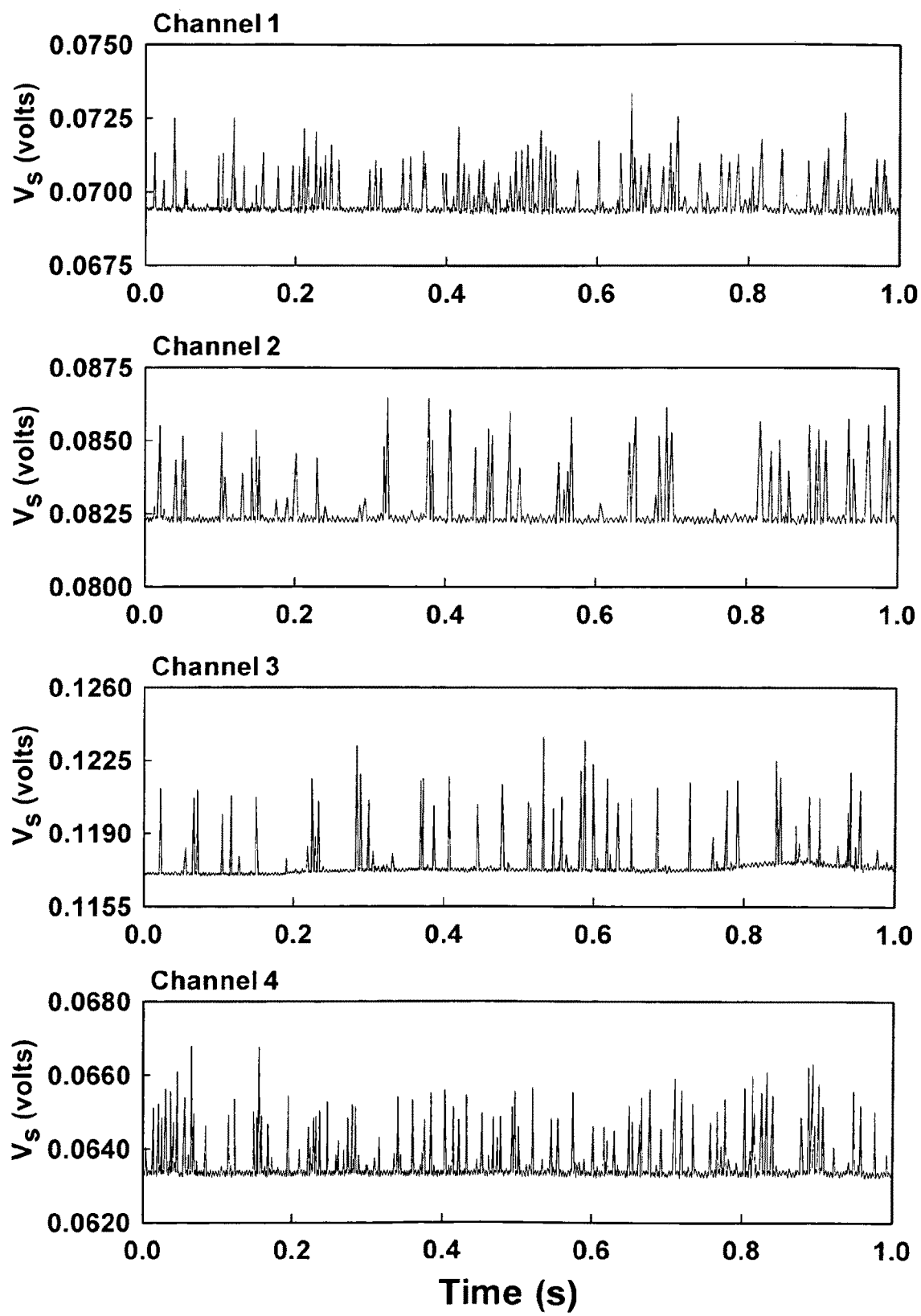
FIG. 14 is a set of four voltage traces obtained from each of the four sampling resistors and shows the voltage response due to Juniper pollen particles.
Figure 15:
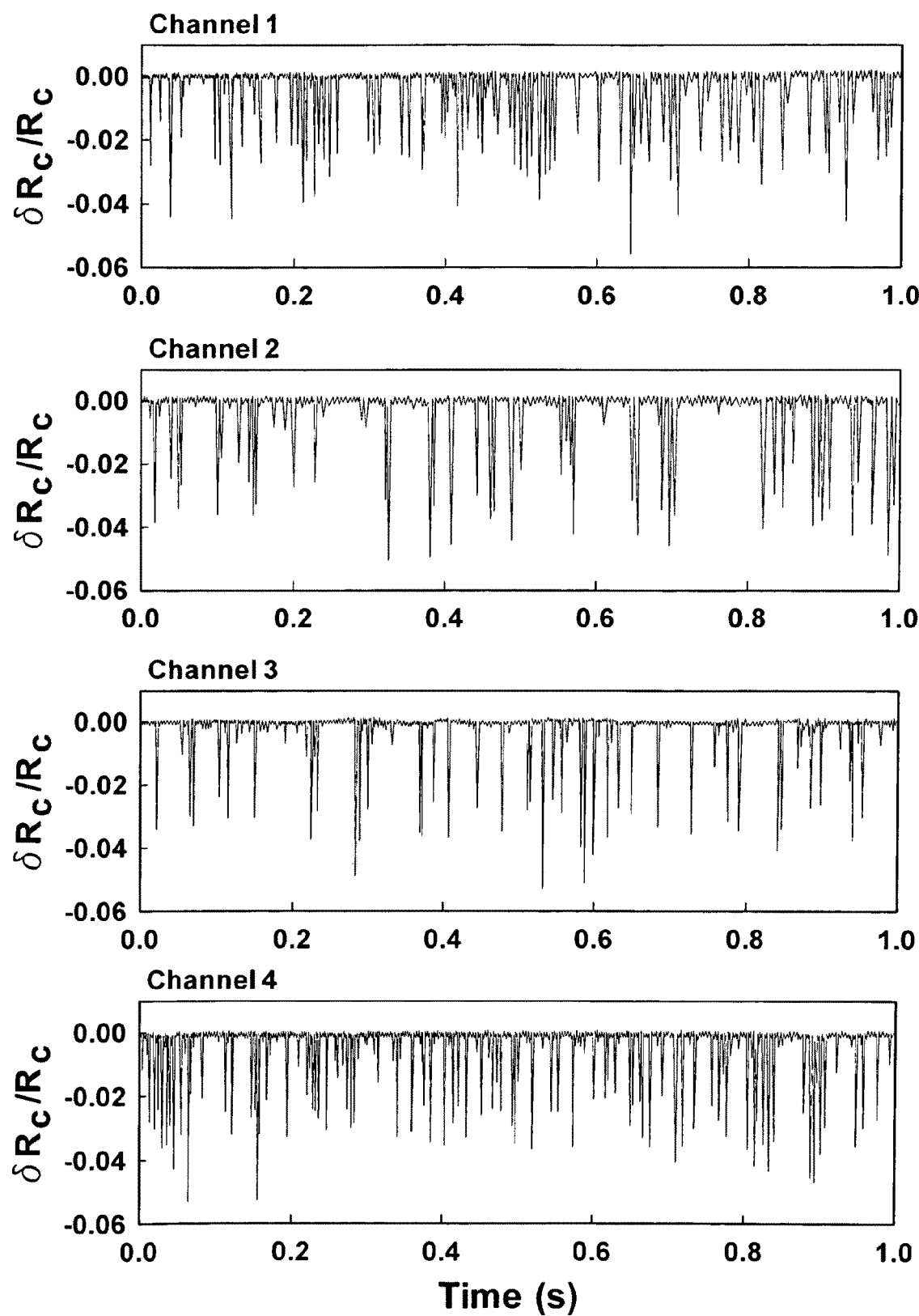
FIG. 15 is a set of four plots of the relative resistance due to Juniper pollen particles.
Figure 16:
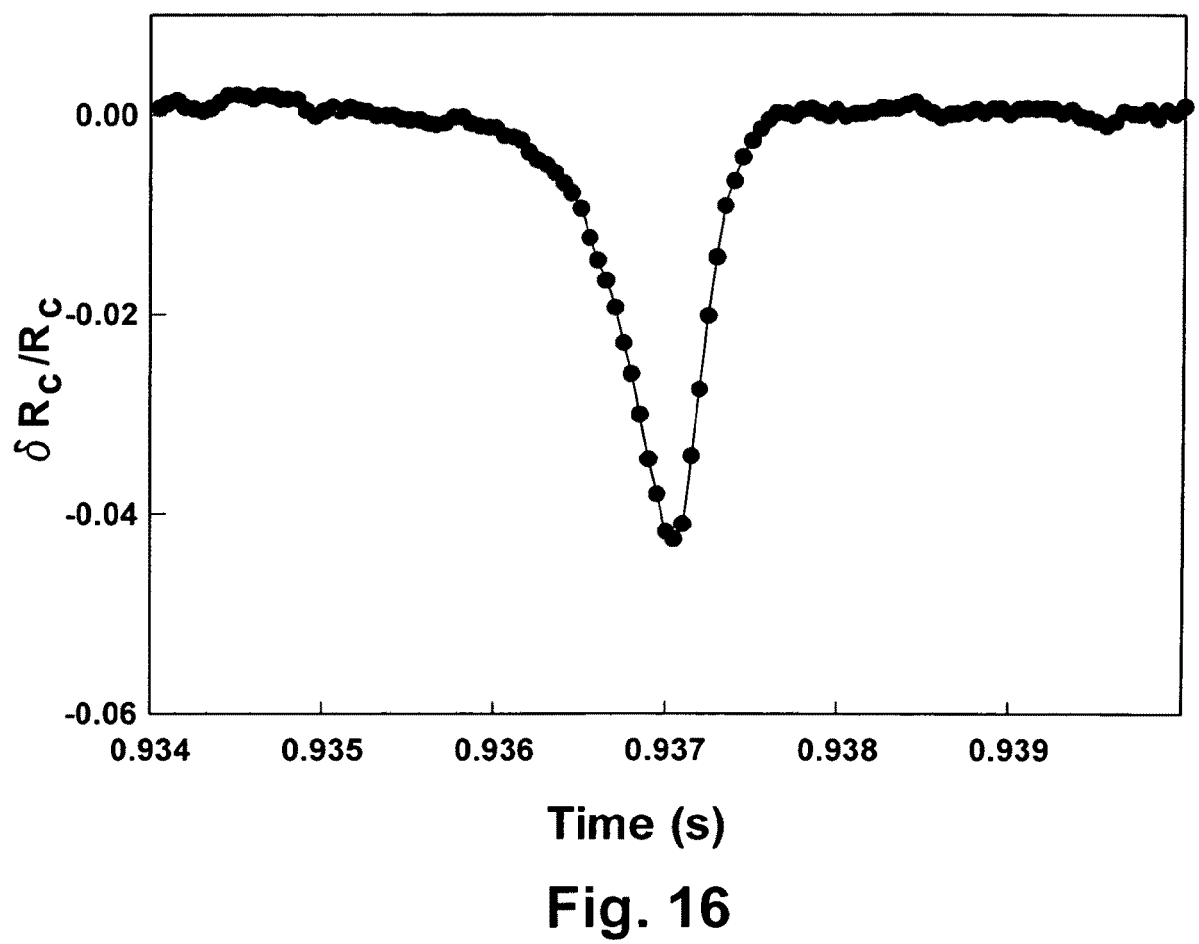
FIG. 16 is a typical resistive pulse resulting from a Juniper pollen particle.

Typical voltage traces with pulses are shown in FIG. 14, and are recorded over a time period of one second. It can be observed that the polarity of the voltage pulses when a pollen particle passes through the microaperture is opposite to that caused by a polymethacrylate particle (FIG. 9). As is the case for the PM particle experiments, the cross-correlation analysis shows negligible crosstalk among channels. The measured voltages are converted to relative changes in aperture resistance as shown in FIG. 15. The downward resistance pulse corresponds to a decrease in the resistance of the microaperture when a pollen particle passes through the aperture. A typical pulse for a Juniper pollen particle taken from FIG. 15 is shown in FIG. 16.

This phenomenon indicates that a particle affects the microaperture resistance in two competing ways. First, it displaces electrolyte solution in the microaperture, thereby reducing the number of free ions inside the microaperture, which leads to an increase in resistance. Second, if it has a surface charge, it brings additional charges into the microaperture, which leads to a decrease in resistance. According to the results from this example, the pollen particles have high surface charge, while the PM particles are only slightly charged. When the surface charge is high and the concentration of ions in the electrolyte solution is low, as is the case for pollen particles in this example, the second factor is dominant, and the overall effect of a pollen particle passing through a microaperture is a downward resistive pulse. This phenomenon can be used to differentiate pollen particles from other only slightly charged particles. It is also possible to measure pollen particle size using electrolyte solution of high concentration, so that the particle size plays the dominant role in the size of the resistive pulse.

In order to further demonstrate that this embodiment can be used to differentiate various particles, two additional particles, 20 μm polymethacrylate particles and Cottonwood pollen, are tested using a single Coulter cell (channel 1 with the 110 μm aperture). These two particles are chosen because they are similar in size to Juniper pollen but may differ in surface properties.

Figure 17A:
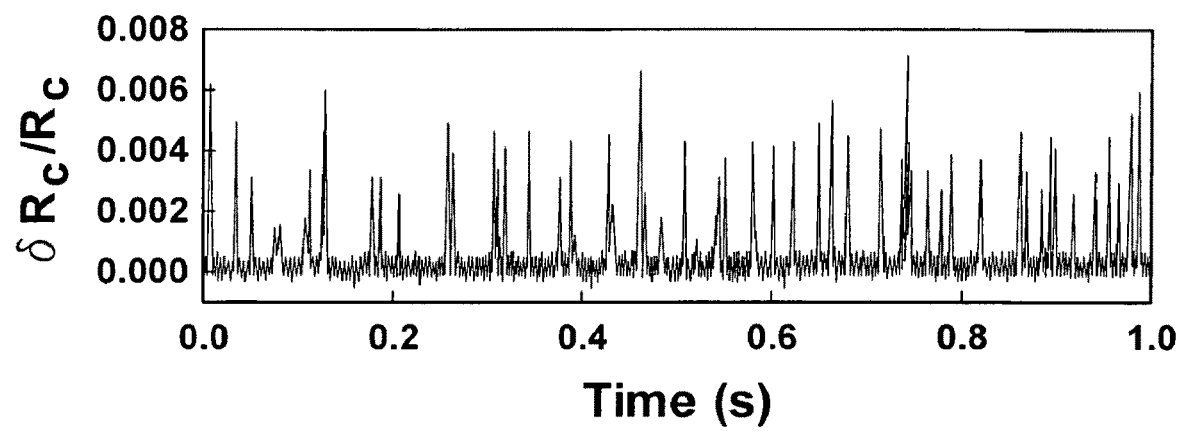
FIG. 17 is a pair of plots showing the relative resistance pulses from a single channel embodiment due to (a) 20 μm PM particles, and (b) cottonwood pollen particles.
Figure 17B:
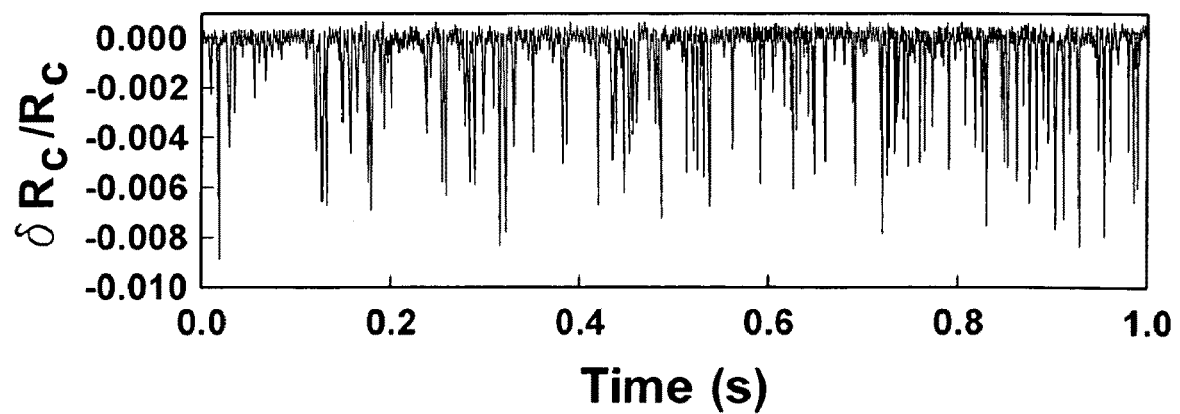

Typical traces of resistive pulses are shown in FIGS. 17(a) and (b). These traces show resistive pulses that are calculated from voltage signals recorded over a one second period. The traces correspond to the 20 μm PM particles, and the Cottonwood pollen. The particle diameters are calculated from the resistive pulse data shown in FIG. 17(a). Using the calibrated aperture length of 173 μm, the statistical analysis shows that the estimated particle diameter is 22.46±2.1 μm. The difference between the calculated and the actual particle diameter (20 μm±0.5 μm) can be minimized by calibrating both the aperture diameter and aperture length using a number of quasi-monodisperse particles of standard sizes. While the estimated particle diameters appear to have a larger divergence about the average than that specified by the manufacturer (20±0.5 μm), the measurement error is approximately within the overall uncertainty error range. The concentration of the 20 μm PM particles is calculated from the number of peaks during a period of one second. According to this example, the concentration is calculated to be $1.91 \times 10^5$ mL$^{-1}$, compared to the original concentration estimate of $2 \times 10^5$ mL$^{-1}$.

Like Juniper pollen, Cottonwood pollen particles generate downward resistive pulses (a decrease in resistance) when they pass through the microaperture (FIG. 17(d)). However, the resistive pulse height (relative to the base resistance of microaperture) generated by Cottonwood pollen (0.478%±0.226%) is considerably lower than that of the Juniper pollen (2.73%±0.99%). While not wishing to be bound to any one theory, this phenomenon may be attributed to a difference in surface charge. The influence of aperture geometry can be eliminated by normalizing the relative resistive pulses for 20 μm and 40 μm PM particles, Juniper pollen, and cottonwood pollen using the following equation:

$$\left(\frac{\delta R_c}{R_c}\right)_{normalized} = \left(\frac{\delta R_c}{R_c}\right) \cdot \left(\frac{L'D^2}{\frac{D^2}{2L^2} + \frac{1}{\sqrt{1 + \left(\frac{D}{L}\right)^2}}}\right) \quad (4)$$

Figure 18A:
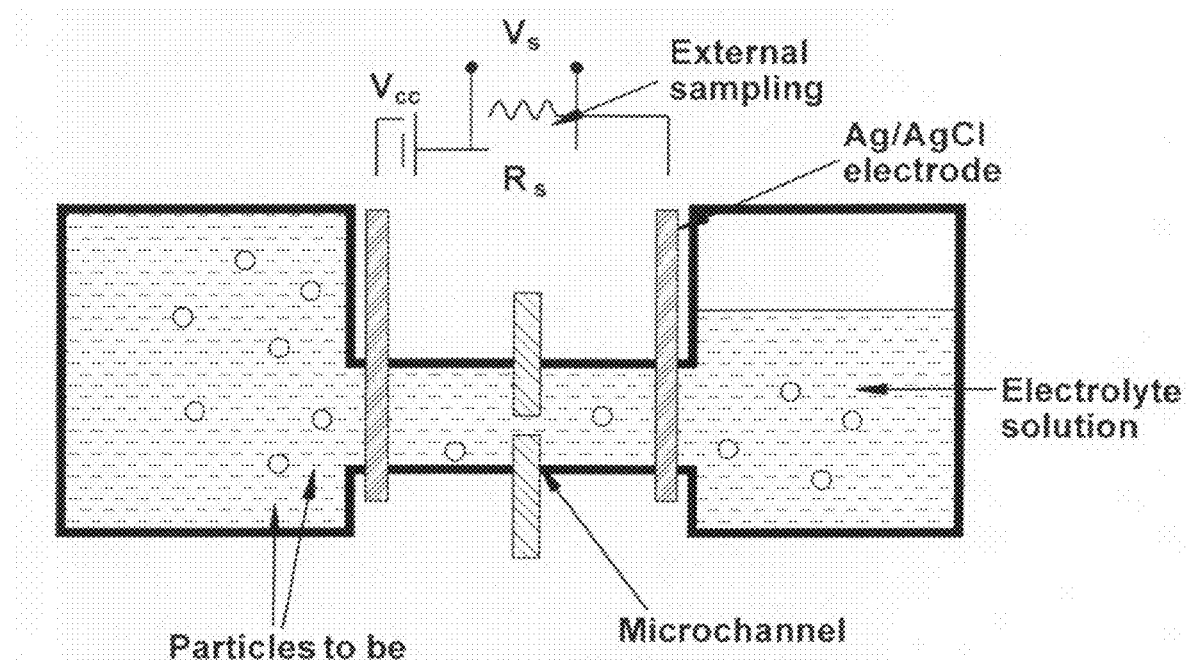
FIG. 18 is a pair of schematics showing (a) a front view of a single channel embodiment; and (b) a magnified view of a single channel embodiment.
Figure 18B:
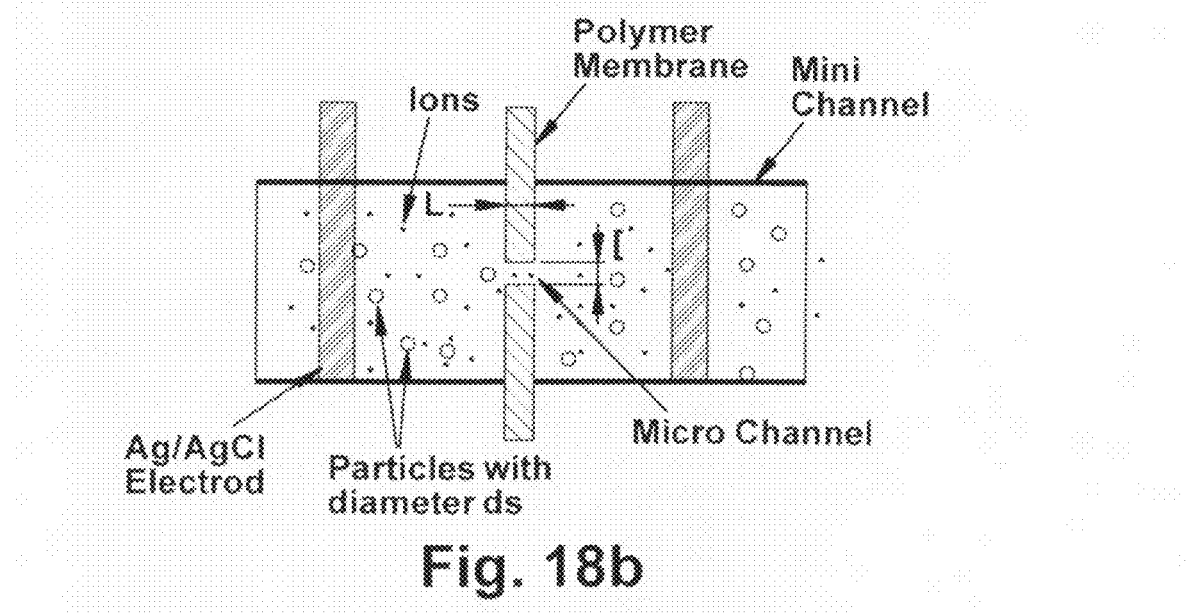

A scatter plot of normalized $\delta R_c/R_c$ for the four particles is shown in FIG. 18. It indicates that the four tested particles can be identified in a mixture by using the polarity and magnitude of the resistive pulses. While not wishing to be bound to any one theory, the large variation in resistive pulses of Juniper tree pollen may be due to a variation in particle size and shape, and in surface charge.

The results for both the PM particle and pollen experiments indicate that this instrument is capable of counting particles through the four microapertures simultaneously. In contrast to a single channel Coulter counter, the counting efficiency is improved by a factor of approximately three. This counting efficiency can be further improved by integrating more sensing apertures in a micromachined device. The noise in the sensed voltages averages to about 0.1 mV. Thus, this embodiment should be able to detect particles that produce pulses larger than this noise level. Accordingly, this embodiment is capable of detecting particles with diameters larger than approximately 8.2 μm, or 6.9% of the microaperture diameter. We expect that the sensitivity can be improved by using better shielding and electronics to reduce the noise level.

The foregoing example demonstrates that some embodiments of the present invention can be used to distinguish between kinds of particles and to count pollen and other particles with significantly improved efficiency.

According to this example, uncertainty analysis is carried out using the methods of Moffat, Kline and Coleman and Steele. There are three sources of uncertainty in the estimation of the particle size. The first source is due to uncertainty in measurement of the microaperture diameter and in the calibration procedure used to determine microaperture length. Due to the fabrication process used to make the microapertures, the microapertures vary in size. The uncertainty in measuring the diameter is ±10%. The calibration process for determining the length presumes that the measured diameter is correct. The uncertainty in diameter causes a maximum uncertainty of ±42.5% for microaperture length. Together, the uncertainties in aperture diameter and length contribute a maximum of ±12.1% uncertainty in particle size evaluation. Note that this source of uncertainty systematically alters the estimates of the particle diameters and can be reduced by calibrating the sensor using quasi-monodisperse particles in a number of standard sizes. Taking data using two different particle sizes, for example, allows the practitioner to solve for both the effective diameter and the effective length of a microaperture, thereby reducing uncertainty for both parameters.

The second source of uncertainty is due to fluctuations in the output voltage, which are about ±0.05 mV at base voltage levels of 0.22 V. These fluctuations could be due to either flow unsteadiness or the measurement electronics, and appear to have no systematic trend. According to Equation (3), this uncertainty contributes to an uncertainty of ±0.58% and ±4.5% in particle diameter estimation for 40 μm and 20 μm polymethacrylate particles, respectively.

The third source of uncertainty is due to particles passing off-axis through the aperture. Given the shape of the pulses observed, we expect a maximum increase of about 10% in the measured response. This corresponds to an uncertainty of ±3.3% in particle size. Combining the three uncertainty sources, the uncertainties of particle size estimation are ±12.5% and ±13.2% for 40 μm and 20 μm polymethacrylate particles, respectively. The foregoing results show that the measurement error of the counter is well within this uncertainty error range.

II. Label-Free Resistive Pulse Sensor Embodiments:

FIG. 5 shows general structure that is consistent with the following embodiment. Similar to the previous embodiment, this embodiment comprises four peripheral reservoirs and a central reservoir. Each peripheral reservoir is connected to the central reservoirs through a mini channel. A microchannel, fabricated on a polymer membrane, is positioned in the middle of each mini channel and used for particle sensing.

FIG. 18($a$) shows the sectioned schematic front view of a single sensing channel along with the measurement setup. $R_s$ is a known external sampling resistor. The Ag/AgCl electrodes placed on both sides of the membrane is used for applying a constant DC voltage $V_{cc}$. FIG. 18($b$) shows a blow-up drawing of the mini-channel, microchannel and electrodes.

Figure 19A:
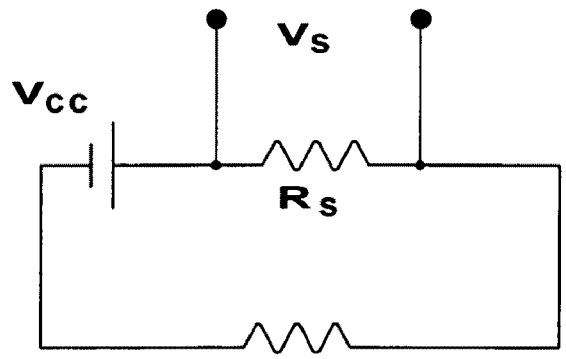
FIG. 19 is a pair of electrical equivalent circuits of (a) a single channel embodiment, and (b) a four channel embodiment.
Figure 19B:
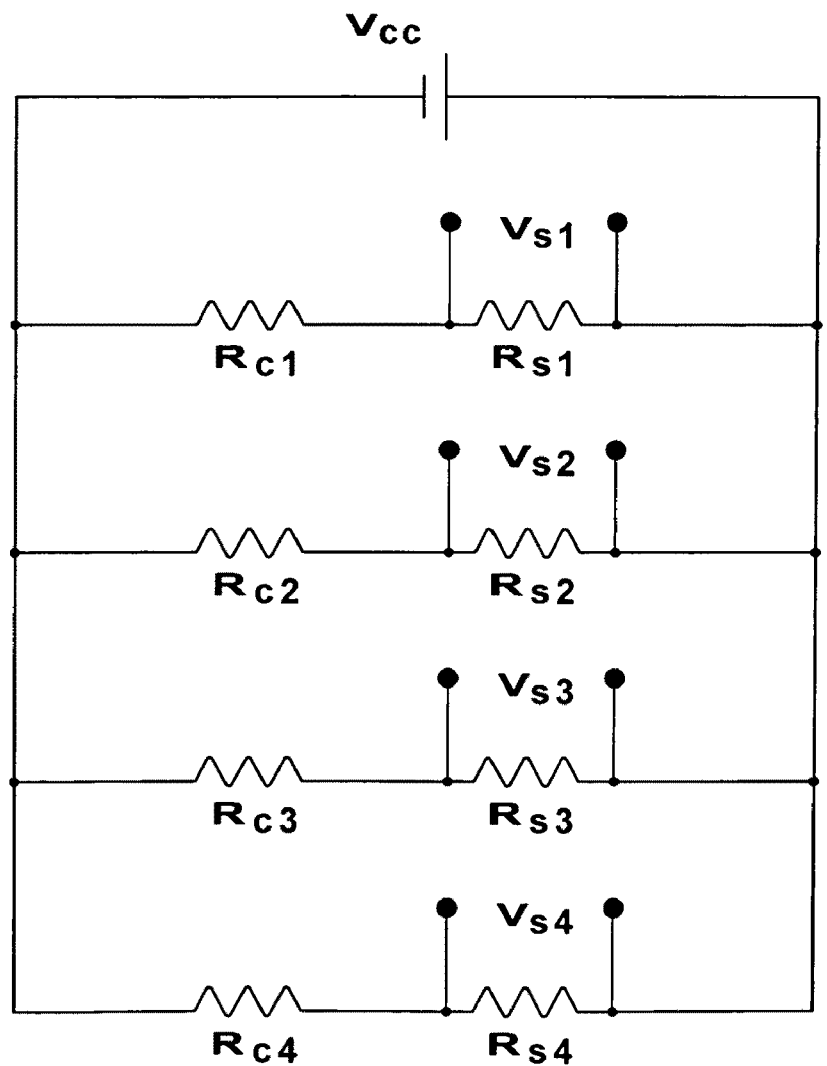

The measurement circuit for one sensing channel is equivalent to the circuit in FIG. 19($a$), where $R_c$ is the resistance of the electrolyte-filled microchannel. $R_c$ has a variation $\delta R_c$ when a particle passes through the channel, because it displaces some of the electrolyte solution in the microchannel. This causes a change in the measured voltage $V_s$ across the sampling resistor $R_s$. From the circuit model in FIG. 19($a$), the relative change in the resistance of the microchannel is given by Equation (1), where $\delta R_c$ is the change in channel resistance when a particle passes through the microchannel, $V_s$ is the voltage measured across the sampling resistor when the channel is filled only with electrolyte solution and $V_s'$ is the peak voltage measured across the sampling resistor as a particle passes through the microchannel.

For a microchannel with length L and diameter D (see FIG. 18($b$)), the change in resistance as a particle passes through it is given by Equation (2). Thus, the particle diameter can be calculated from the relative change in resistance based on Equation (3).

According to one very specific example, the central reservoir and half of each of the four mini channels can be fabricated by drilling holes in a polymethyl methacrylate (PM) block. In each of four additional PM blocks, holes are drilled to form the other half of a mini channel and a peripheral reservoir. According to this example, the central reservoir is 12 mm in diameter and 10 mm deep. Each peripheral reservoir is 10 mm in diameter and 10 mm deep. The mini channel is 4 mm in diameter. After the holes are drilled, the PM blocks are cleaned with isopropanol and sonicated in an ultrasound bath. The microchannels are fabricated by carefully piercing four polymer membranes with a heated micro needle. The membranes are inspected under a high precision microscope and the diameters of the microchannels are measured to be between 120 μm and 130 μm, as shown in Table 4. The thickness of the membrane (and therefore the length of each microchannel) is measured to be approximately 100 μm.

TABLE 4

|  | Channel 1 | Channel 2 | Channel 3 | Channel 4 |
|---|---|---|---|---|
| Length L | 100 μm | 100 μm | 100 μm | 100 μm |
| Diameter D | 120 μm | 120 μm | 130 μm | 120 μm |

To assemble the device, the PM block with the central reservoir and one of the PM blocks with a peripheral reservoir are picked, and epoxy is applied on the mini channel side of the two blocks. A membrane is placed between the two blocks and is carefully aligned so that its microchannel is centered between the two halves of the mini channel. The blocks are then clamped together and kept about two to five hours, or until the two blocks and the membrane are firmly attached together. A pair of 1 mm holes, located 5 mm away from each membrane on both sides, is drilled on the PM blocks. The 1 mm diameter Ag/AgCl electrodes are placed on both sides of the membrane through the 1 mm holes. Then epoxy is applied to fix the electrodes and seal the mini channel. The same procedure is repeated for the other three peripheral blocks to form a four-channel sensor.

Figure 20A:
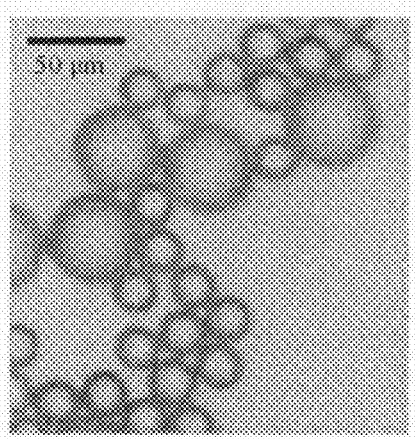
FIG. 20 is a set of three photomicrographs of (a) 20 μm PM particles and 40 μm PM particles, (b) cottonwood pollen, and (c) Juniper *Scopulorum* pollen.
Figure 20B:
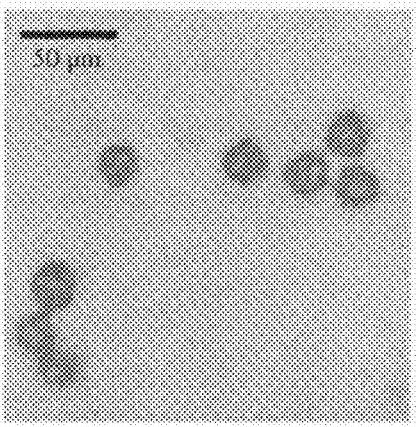
Figure 20C:
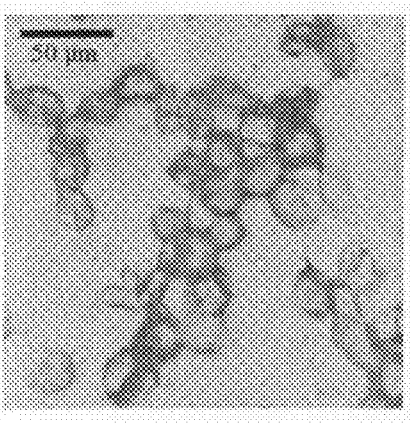

Four microparticles, polymethacrylate particles with well-characterized diameters of 20 μm (20 μm±0.5 μm) and 40 μm (40 μm±0.8 μm) (Sigma Aldrich Inc.), Rocky Mountain Juniper (Juniper *Scopulorum*) tree pollens (Sigma Aldrich Inc.) and Populus deltidoes/Eastern Cottonwood pollens (Sigma Aldrich Inc.) are chosen for testing. These particles are chosen because they are commercially available and have well-characterized properties. The diameters of pollen particles are determined using high resolution optical microscopy. The cotton pollen had a diameter of about 20 μm. The Juniper tree pollen is egg-shaped and its diameter ranged from 17 μm to 23 μm. FIG. 20($a$) shows pictures of the 20 μm and 40 μm polymethacrylate particles. FIGS. 20($b$) and ($c$) shows the pictures of Cottonwood and Juniper tree pollen respectively taken with the microscope.

Four particle solutions are prepared before the experiments. 40 μm polymethacrylate particle solutions are prepared by diluting 0.1 mL original particle solution, which has 10% solid content, in 2 mL of deionized water. The yield particle concentration of 40 μm solution is approximately $1.2 \times 10^5$ mL$^{-1}$. 20 μm polymethacrylate particle solutions are prepared by diluting 0.1 mL original particle solution (10% solid content) in 7 mL of deionized water and the yield particle concentration of 20 μm solution is approximately $2.8 \times 10^5$ mL$^{-1}$. For Cottonwood and Juniper tree pollen particles, the particle solutions are formed by diluting 0.1 mL of the original pollen particle solutions (10% solid content) in 7 mL of deionized water.

The prepared particle solution is injected into the peripheral reservoirs separately using a micro syringe. Juniper tree pollen particles, Cottonwood particles, 40 μm and 20 μm polymethacrylate particles are loaded into channels 1, 2, 3 and 4 respectively. The liquid in each peripheral reservoir is agitated to make sure that the particles are well dispersed. A pressure difference is formed by setting a level difference between the peripheral reservoirs and central reservoir. The particle solutions are driven to move from the peripheral reservoirs towards the central reservoir, which now act as a collecting/sink reservoir.

The entire measurement setup is placed in a Faraday cage to reduce noise. The applied electric potential across the pair of electrodes of each channel is $V_{cc}$=3 V. The sampling resistor for each channel is 100 kΩ. As the particles passes through the microchannels, voltage pulses across all sampling resistors are recorded simultaneously using a National Instruments NI-6220 data acquisition board. The voltages are monitored in real-time using LabView software with a sampling frequency of 20 KHz. The data obtained are converted to relative resistance change ($\delta R_c/R_c$) using Equation (1). The relative change is used to estimate the particle diameter (using Equation (3)) and particle concentration.

Figure 22B:
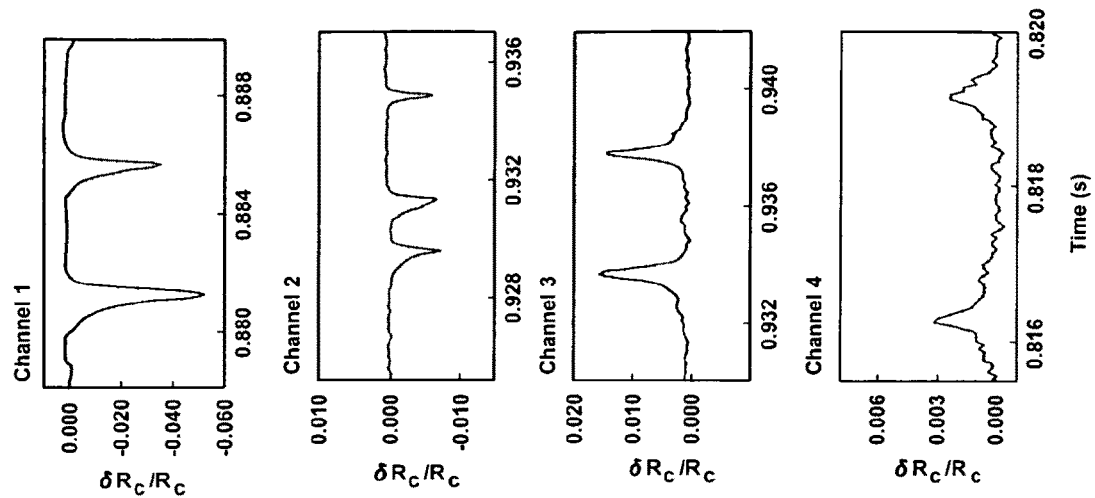
FIG. 22 is a set of plots showing (a) the relative resistance of each channel, and (b) magnified resistive pulses for each channel.

Example of Label-Free High-Throughput Resistive-Pulse Sensing:

The typical measurement results of voltage traces across the four sampling resistors during a selected period of time are shown in FIG. 21(a). A few magnified pulses showing more details of the pulse shape are shown in FIG. 21(b). It is obvious that the voltage pulses appear in random sequence. The cross correlation analysis is performed between the signals from two sensing channels at a time. We found that the cross correlation coefficients are all less than 5%, indicating there is no correlation among the pulses of different channels. This implies that the four sensing channels can simultaneously detect and count particles without crosstalk among the channels. Note that the difference in the base voltage ($V_s$) is due to the base resistance difference ($R_{c1}$, $R_{c2}$, $R_{c3}$, $R_{c4}$) among microchannels because of the fabrication variation. The particle travel velocity in the microchannel is estimated by measuring the pulse width (i.e., time one particle took to pass the microchannel) and the length of the microchannel, which is used to estimate the particle concentration later. Some resistive pulses shown in FIGS. 21(b) and 22(b) have a steeper slope when the particles exit the microchannel than they enter the microchannel. This may be a result of the particles entering the microchannel at the center and exiting the microchannel near the channel wall at an angle.

Figure 22A:
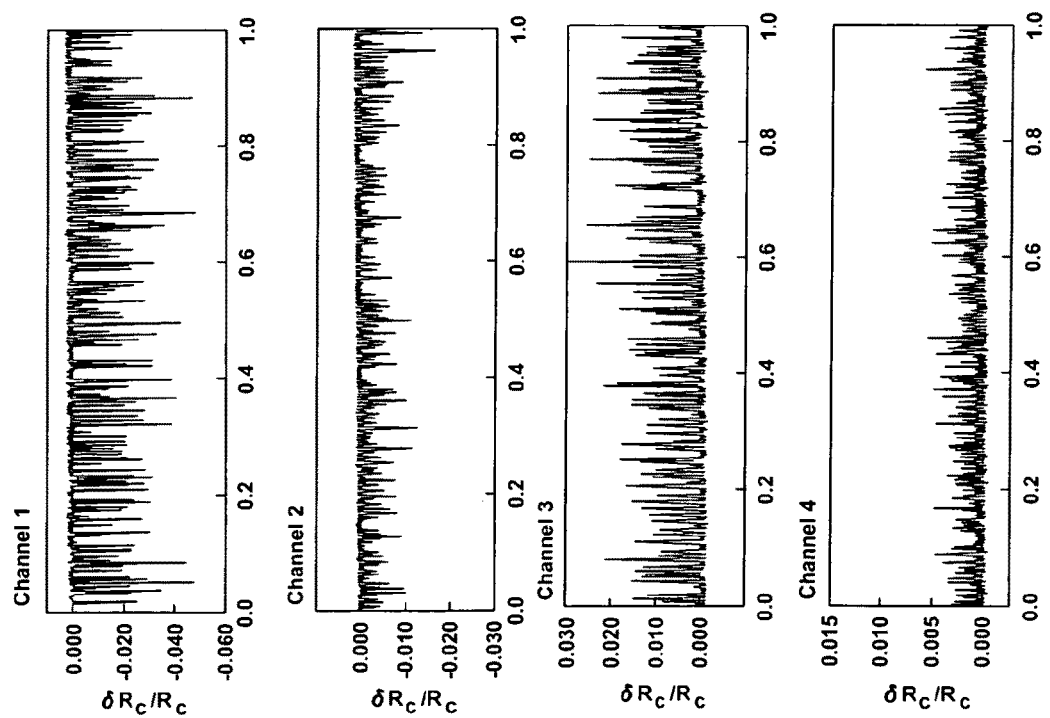

The voltage pulses of each microchannel are converted to the ratio of the resistance change using equation. The results are plotted in FIG. 22(a) as a function of time, along with a few magnified resistive pulses showing more details in FIG. 22(b). It is obvious that the four types of particles can be differentiated based on the direction (downward or upward) and height of resistive pulses.

Figure 23A:
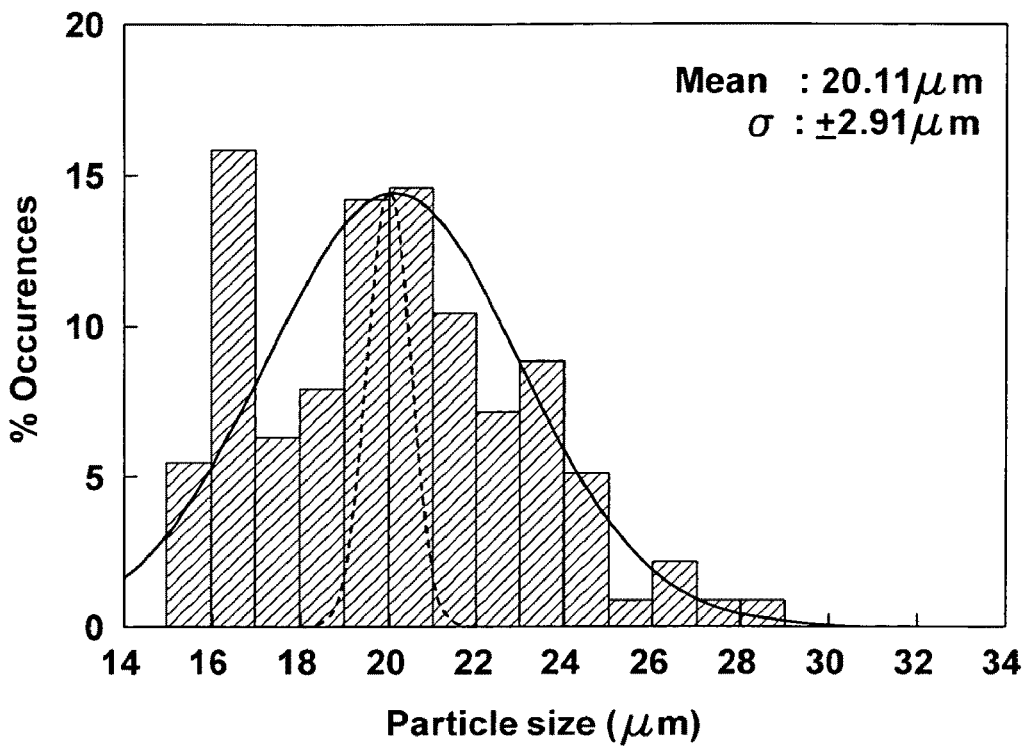
FIG. 23 is a pair of histograms showing the estimated particle size of (a) a 40 μm particle, and (b) a 20 μm particle.
Figure 23B:
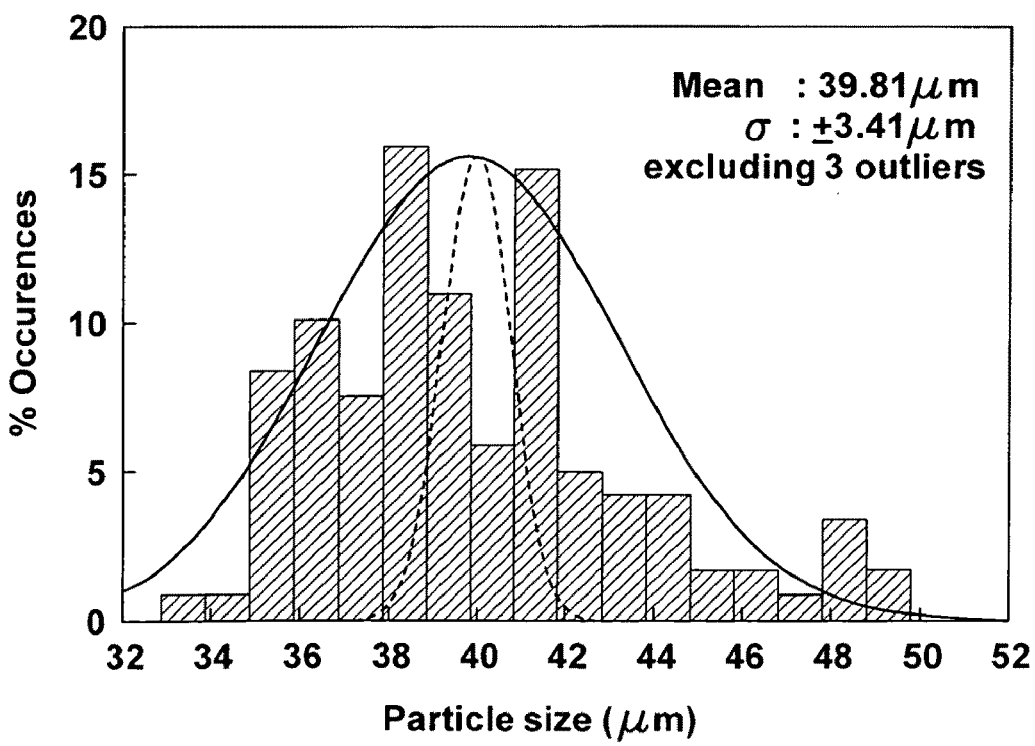

The relative changes of resistance in channels 3 and 4 are used to calculate the polymethacrylate particle diameters using Equation (3). FIG. 23 shows a histogram of the estimated particle size, along with the average size and standard deviation in size, for channels 3 and 4. The estimated particle diameters lie in the range of about 32.89 to 48.96 µm (average 39.81 µm, σ=±3.41 µm) for channel 3, about 15.68 to 28.18 µm (average 20.11 µm, σ=±2.91 µm) for channel 2. The estimated particle size appears to have relatively larger divergence compared to the actual diameter of the polymethacrylate particles specified by the manufacturer, which are 40±0.8 µm and 20±0.5 µm. This is possibly because of the uncertainties in microchannel dimension, electronic noise and the off-axis position when particles pass through the microchannel. The measurement error in the particle size is approximately within the overall uncertainty error range. From the number of peaks appearing in channels 3 and 4 during a period of one second, the concentrations of particles are calculated to be $1.33 \times 10^5$ mL$^{-1}$ (estimated actual concentration is $1.2 \times 10^5$ mL$^{-1}$), $2.46 \times 10^5$ mL$^{-1}$ (estimated actual concentration $2.8 \times 10^5$ mL$^{-1}$), respectively. The calculated concentrations from measured resistance pulses are in good agreement with the estimated actual concentrations. The slight difference is possibly because of the non-uniformity of particle distribution in the solution. The results show that the device is capable of counting polymethacrylate particles and determining their sizes accurately.

Figure 24A:
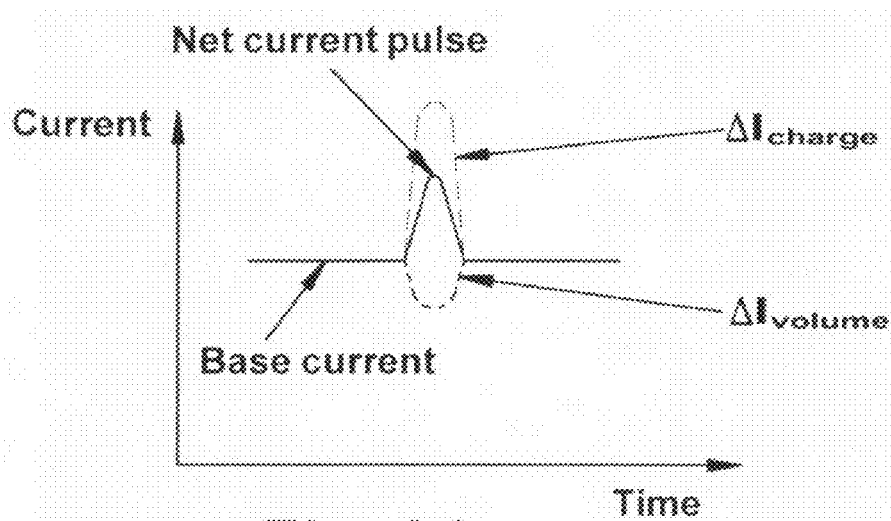
FIG. 24 is a set of drawings showing (a) a qualitative illustration of resistive pulse shape, (b) the result of a neutral particle entering a channel, and (c) the result of a charged particle entering a channel.
Figure 24B:
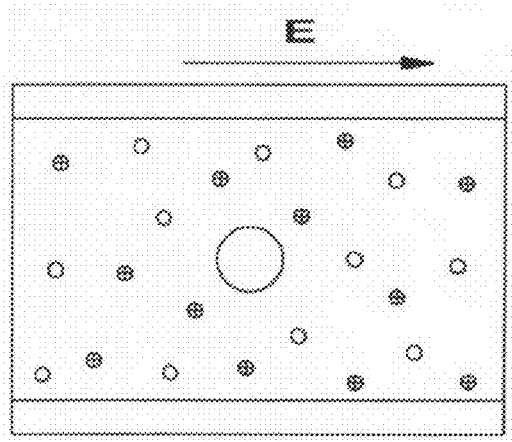
Figure 24C:
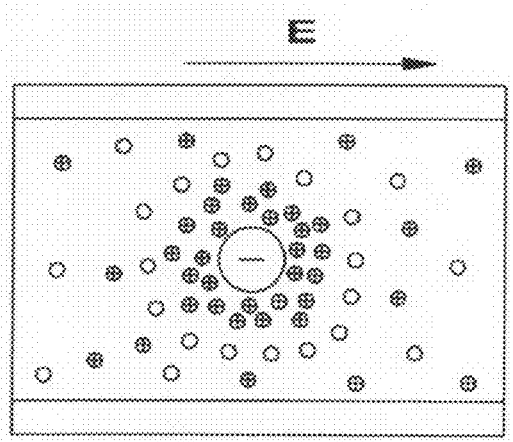

As shown in FIG. 22, in channels 1 and 2, the resistance pulses caused by Juniper pollens and Cottonwood pollens are all downward. This implies a decrease in the microchannel resistance when a pollen particle passed through the microchannel. This phenomenon can be explained in terms of the surface charge of particles. As illustrated in FIG. 24(a), a particle affects the ionic current in two competing ways: first, the particle physically displaces some of the electrolyte solution and reduces the amount of free ions inside the microchannel and hence the ion density σ. The ionic current across the microchannel can be written as:

$$I = \int_A \sigma \mu E \, dA \tag{5}$$

where µ is the mobility of the free ions, E is the applied electric field and A is the cross section area. Therefore the particle induces a decrease in ionic current ($\Delta I_{volume}$) as usually expected. Second, if the particle has high surface charge (see FIG. 24(b)), it induces excess ions in the microchannel owing to its high surface charge. Hence the ion density σ increases, leading to an increase in ionic current ($\Delta I_{charge}$). When the particle surface charge is high and the concentration of ions in the electrolyte solution is low, as is the case in the present example, the ionic current increase ($\Delta I_{charge}$) is dominant (FIG. 24(c)). The overall effect of a particle with high surface charge passing through a microchannel is an upward ionic current pulse (see FIG. 24(a)). Therefore, according to Ohm's Law, R=V/I (V is the applied voltage), a downward resistive pulse will occur. If the surface charge of a particle is negligible, $\Delta I_{charge}$ is negligible and an upward resistive pulse is generated. The results presented in this example suggest that pollen particles are highly charged, while polymethacrylate particles are slightly charged. While not wishing to be bound to any one theory, the height of downward resistive pulses could be explained by the surface charge of pollen particles. Furthermore, according to this example, the size of pollen particles can be measured in high concentration electrolyte solutions (e.g., 0.1 M KCl solution, for instance), because the induced charge density increase due to pollen is negligible at concentrations.

Figure 25:
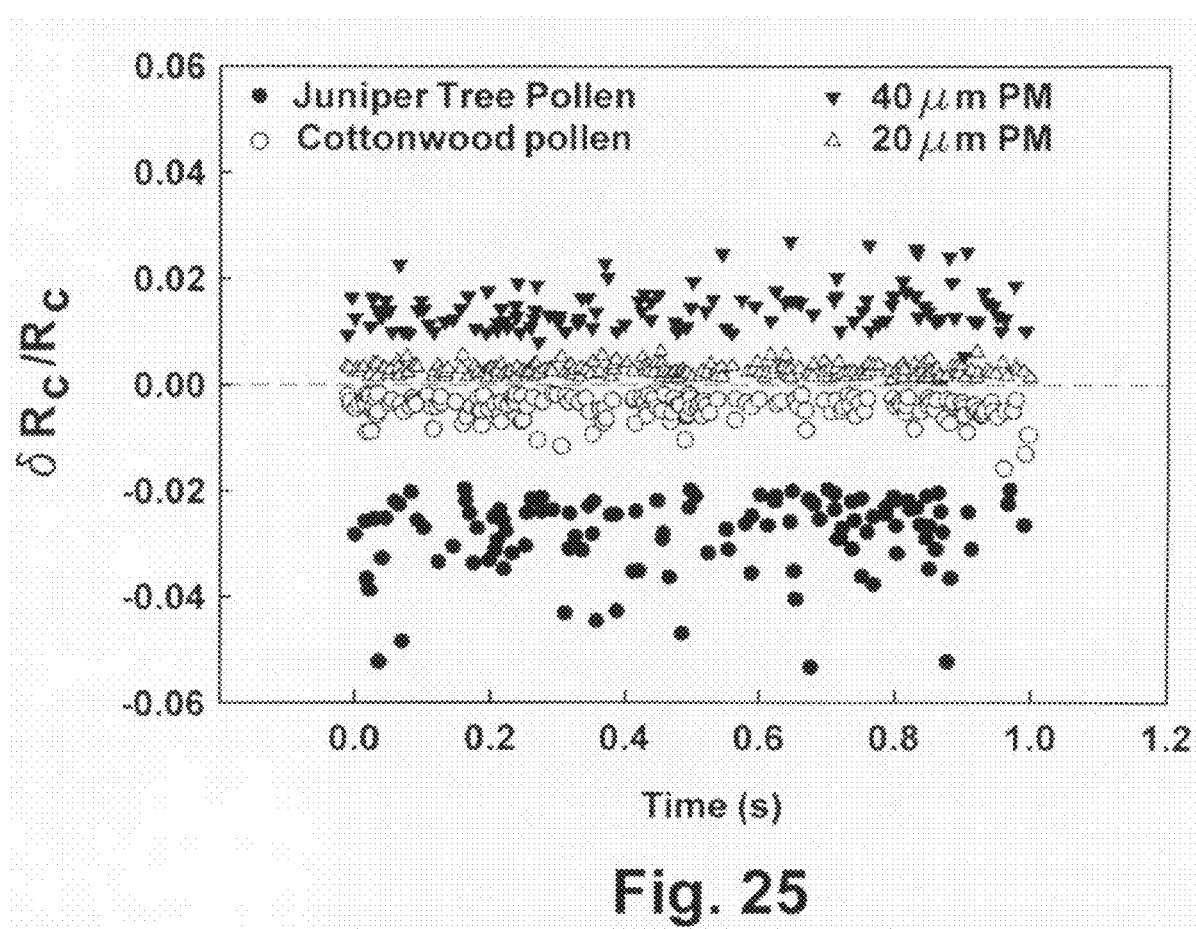
FIG. 25 is a scatter plot of the relative resistive pulse heights due to four different particles, i.e., 20 μm PM, 40 μm PM, cottonwood pollen, and Juniper pollen.

As demonstrated by this example, pollen generates downward resistive pulses. Thus, it can be used to differentiate between pollen particles from other slightly charged or non-charged particles. FIG. 25 shows a scatter plot of the relative resistance $\delta R_c/R_c$ for the polymethacrylate particles and the pollen particles during a period of one second. The plot shows that there are four distinct regions of resistive pulses of the tested particles. The average resistive-pulse heights and the standard deviation are calculated and listed in Table 5.

TABLE 5

|  | Average relative resistive-pulse height ($\delta R_c/R_c$) (%) | Standard deviation (%) |
|---|---|---|
| 20 µm polymethacrylate | 0.23 | 0.104 |
| 40 µm polymethacrylate | 1.44 | 0.392 |
| Juniper pollen | −2.83 | 0.716 |
| Cottonwood pollen | −0.478 | 0.226 |

According to this example, polymethacrylate particles generate upward resistive pulses while pollen particles generate downward pulses. From FIG. 25, the 20 µm polymethacrylate particles and 40 µm polymethacrylate particles can be distinguished by size exclusion. In spite of the similar sizes of Juniper pollens and Cottonwood pollens (both are approximately 20 µm), the restive pulse heights generated by Juniper pollens are approximately six times higher than that of Cottonwood pollens. While not wishing to be bound to any one theory, the resistive-pulse difference might be attributed to the difference in the surface charge of pollen particles. Therefore, if the polymethacrylate particles and the pollen particles are mixed in DI water, one can distinguish and count them separately based on their resistive pulses. FIG. 25 also shows that the pulse heights of the Juniper tree pollen have more variations compared to the Cottonwood pollen. One explanation for this is that the variation is due to particle size variation and the egg shape of Juniper pollens.

FIG. 25 demonstrates that some embodiments of the present invention make it is possible to distinguish and count mixtures of various particles with similar sizes but different surface properties. In the following example an embodiment is demonstrated to be capable of distinguishing and counting mixtures of (1) 20 μm polymethacrylate particles and Juniper tree pollen, and (2) 20 μm polymethacrylate particles and Cottonwood pollen.

Twenty micrometer polymethacrylate particles, Cottonwood pollen and Juniper pollen solutions are prepared separately as set forth previously. Mixture 1 is prepared by combining 7 mL 20 μm polymethacrylate particle solution, and 3 mL Juniper pollen solution. Mixture 2 is prepared by combining 7 mL 20 μm polymethacrylate particle solution, and 3 mL Cottonwood pollen solution. The estimated polymethacrylate particle concentration is calculated to be $1.99 \times 10^5$ mL$^{-1}$ for both mixtures. The two particle mixtures are loaded to peripheral reservoirs 1 and 2, respectively. The microchannel diameters for channels 1 and 2 are 100 μm and 110 μm. Channels 3 and 4 are closed using polymer membranes without microchannels.

Figure 26A:
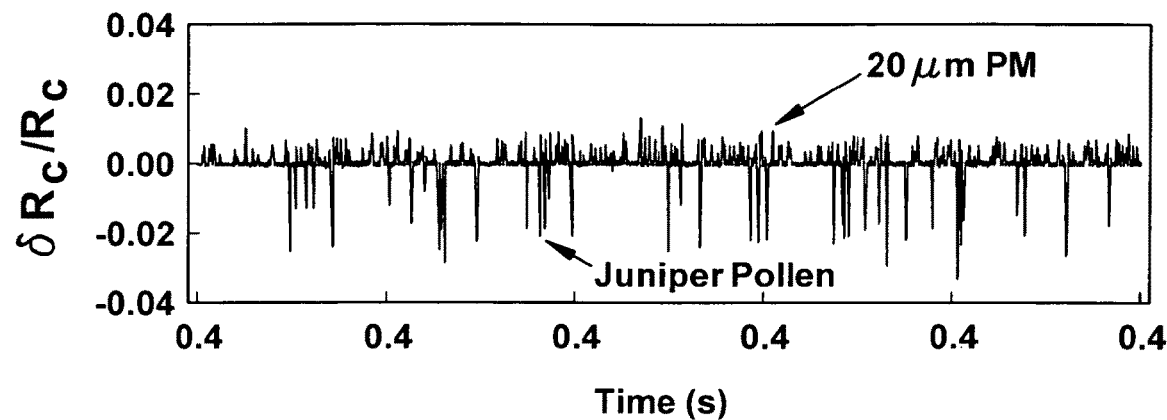
FIG. 26 is a plot of relative resistance as a function of time for (a) channel 1, and (b) channel 2.
Figure 26B:
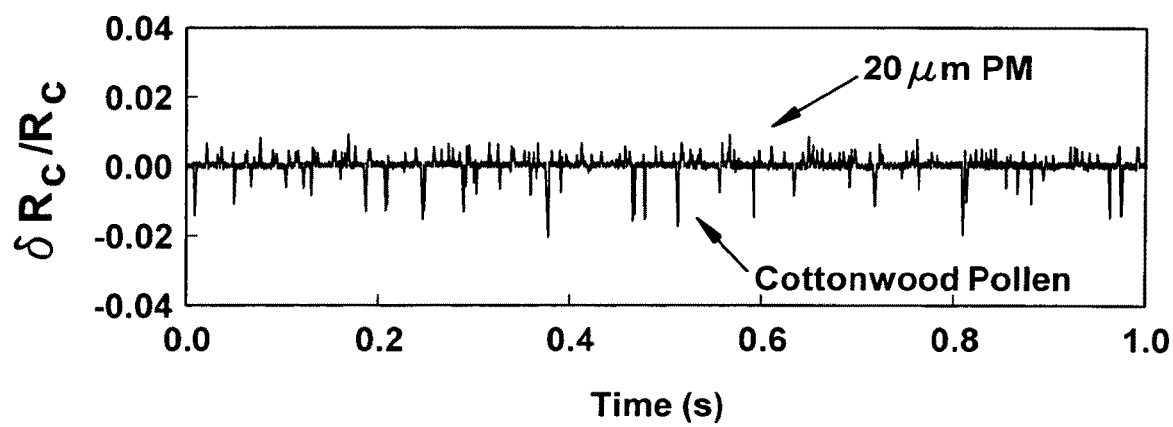

Typical traces of resistive pulses converted form the recorded voltage signal are shown in FIGS. 26(a) and (b). According to this data, 20 μm PM particles can be differentiated and counted based on the resistive pulses they generate.

The diameters and concentrations of polymethacrylate particles, calculated from experimental data in channels 1 and 2, are shown in Table 6.

Similar to the foregoing results of 20 μm polymethacrylate particles, the calculated particle diameters have larger variations than that which is specified by the manufacturer. The calculated concentrations of 20 μm polymethacrylate particles are $1.72 \times 10^5$ mL$^{-1}$ and $1.94 \times 10^5$ mL$^{-1}$, compared to the estimated actual concentration of $1.99 \times 10^5$ mL$^{-1}$.

TABLE 6

| | Calculated particle size (μm) | Vendor's specification (μm) | Calc. particle conc. (mL$^{-1}$) | Est. particle conc. (mL$^{-1}$) |
| --- | --- | --- | --- | --- |
| μ-channel 1 (100 μm) Mixture 1 | 20.38 ± 2.51 | 20.00 ± 0.5 | $1.72 \times 10^5$ | $1.99 \times 10^5$ |
| μ-channel 2 (110 μm) Mixture 2 | 20.44 ± 2.27 | 20.00 ± 0.5 | $1 \times 10^5$ | $1.99 \times 10^5$ |

These results indicate that this multi-channel resistive-pulse sensor is capable of differentiating and counting multiple particle solutions through the four microchannels simultaneously. In contrast to a typical Coulter counter that can only analyze one particle solution, the sensor throughput is improved approximately 300%. The throughput can be further improved by fabricating more sensing channels in the device. The noise seen in the measured voltages averaged ±0.05 mV, so the device is capable of detecting particles that produce pulses larger than this noise level.

This suggests that the device is capable of detecting particles with diameters larger than approximately 8.9 μm, or 7.4% of the microchannel diameter. Sensitivity can be improved by improving shielding, and by the introduction of more sophisticated electronics to reduce the noise level. The multi-channel sensor reported herein combines size/surface charge exclusion separation and high throughput electronic detection in a simple device. The electrical properties or surface characteristics of biological particles are of great interest in recent years for novel rapid assays of these particles. These pollen results indicate that the multi-channel resistive-pulse device can be used to differentiate various pollen particles in terms of their surface characteristics and/or electrical properties. Although only four types of particles are tested, the resistive pulses due to the passage of various other biological particles are expected to exhibit distinct signals because of difference in electrical properties and/or surface characteristics of biological particles. Thus, some embodiments of the present invention provide a label-free means for detecting and counting biological particles. For instance, in addition to the size/surface charge exclusion, the measurement of the shape of the resistive pulses provides more detailed information of particles, including mobility, surface characteristics, electrical properties, and the like. In one embodiment, this could be done by reducing the particle travel velocity in the microchannel. Travel velocity can be controlled by forcing the particles to pass through microchannels using electrophoresis or a small pressure gradient, and by using a high sampling frequency.

Because of the simple structure of the multi-channel resistive-pulse device, throughput can be improved further by integrating more micro sensing channels. Further, some embodiments can comprise lab-on-a-chip devices having, for instance micromachined fluid channels, micro/nano-scale sensing channels and detection electronics. Additionally, use of multiple sensing channels enables multiplexing applications. This allows high throughput signal measurements with a high signal-to-noise ratio without compromising sensitivity. Therefore, the multi-channel resistive-pulse sensor embodiment can include a portable, high throughput micromachined device for micro and nano-scale bioparticle analysis.

Uncertainty analysis using the methods of Kline, Moffat and Coleman and Steele is carried out. There are three sources of uncertainty in the estimation of the particle size. The first source is due to uncertainty in the measurement of microchannel diameter and length. Due to the fabrication variation of the microchannel, these uncertainties are ±10% for diameter, and ±20% for channel length. These uncertainties contribute a ±10.5% uncertainty in particle size evaluation. Note that this source of uncertainty would systematically alter the estimated particle diameters.

The second source of uncertainty is due to the fluctuations in the output voltage, which are about ±0.05 mV at base voltage levels of 0.2 V. These fluctuations are due to measurement electronics and appear to have no systematic trend. According to Equation 5, this uncertainty contributes to an uncertainty of ±4.0% and ±0.7% in particle diameter estimation respectively for 20 μm particles and 40 μm particles.

The third source of uncertainty is due to the off-axis position when one particle passes through the microchannel. This results in a maximum uncertainty of about ±10% in the resistive pulse, which corresponds to an uncertainty of ±3.2% in particle size. Combining the three uncertainty sources, the uncertainties of particle size estimation are ±11.7% and 11% for 20 μm particles and 40 μm particles, respectively. The foregoing results show that the measurement error of the sensor is approximately within this uncertainty error range.

Figure 27:
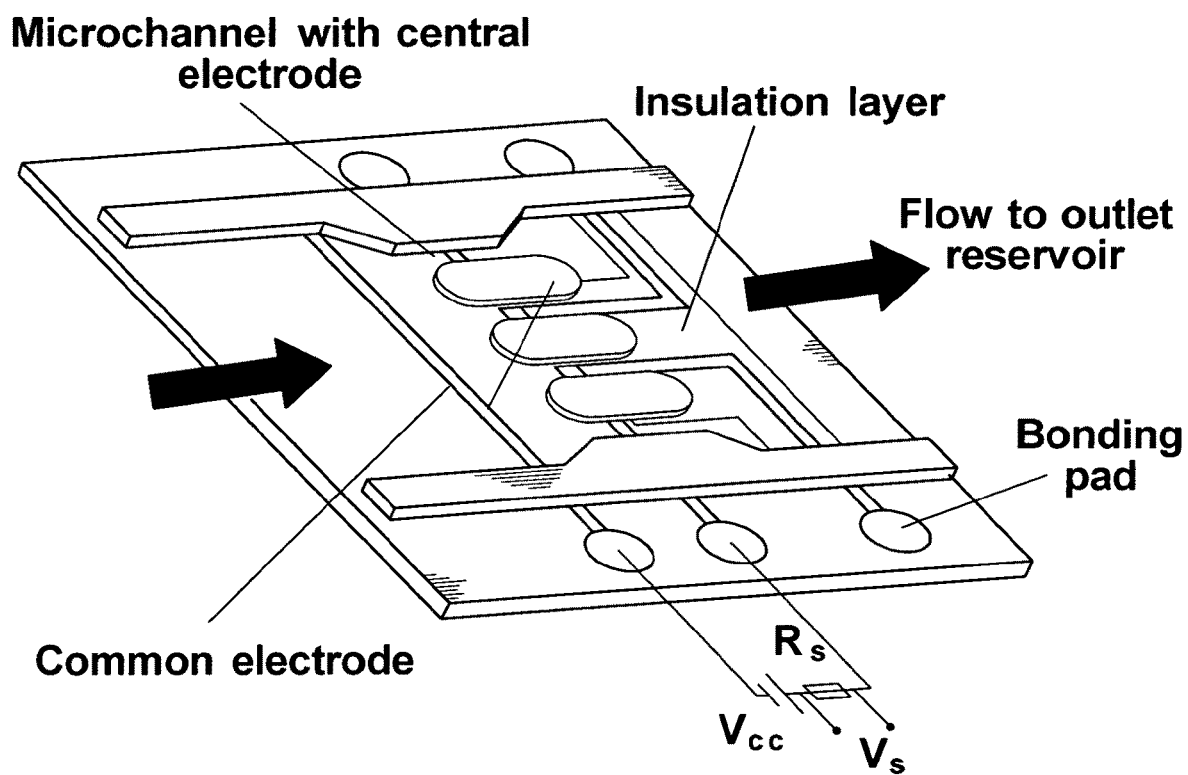
FIG. 27 is a schematic drawing of a micromachined multichannel resistive pulse sensor embodiment.

III. Microfluidic High-Throughput Resistive Pulse Sensor Embodiments:

The design concept of one embodiment is illustrated in FIG. 27. This embodiment comprises a multichannel resistive pulse sensor. The sensor comprises a single inlet reservoir and a single outlet reservoir, connected by four microchannels of dimensions 50 µm×100 µm×300 µm. The device has a common electrode placed in the inlet reservoir at the entrance of the microchannels and four central electrodes fabricated at the centers of the four microchannels. Each central electrode is exposed to the electrolyte only at the center of the channel for measurement purposes. The measurement setup for one channel is illustrated in FIG. 27, and comprises a constant DC power supply $V_{cc}$ connected to the common electrode at one end and to a sampling resistor at the other end. Electrolyte containing particles is forced to move from the inlet reservoir to the outlet reservoir through a plurality of sensing channels. When a particle passes through a channel, it causes a change in the resistance of the electrolyte-filled channel, thereby resulting in a voltage pulse across the sampling resistor of that channel. The voltage pulses across each sampling resistor can be recorded and analyzed separately. In contrast to a single channel Coulter counter, the sensor can detect particles through its four sensing channels simultaneously. Thus, the design enables high throughput.

Figure 28:
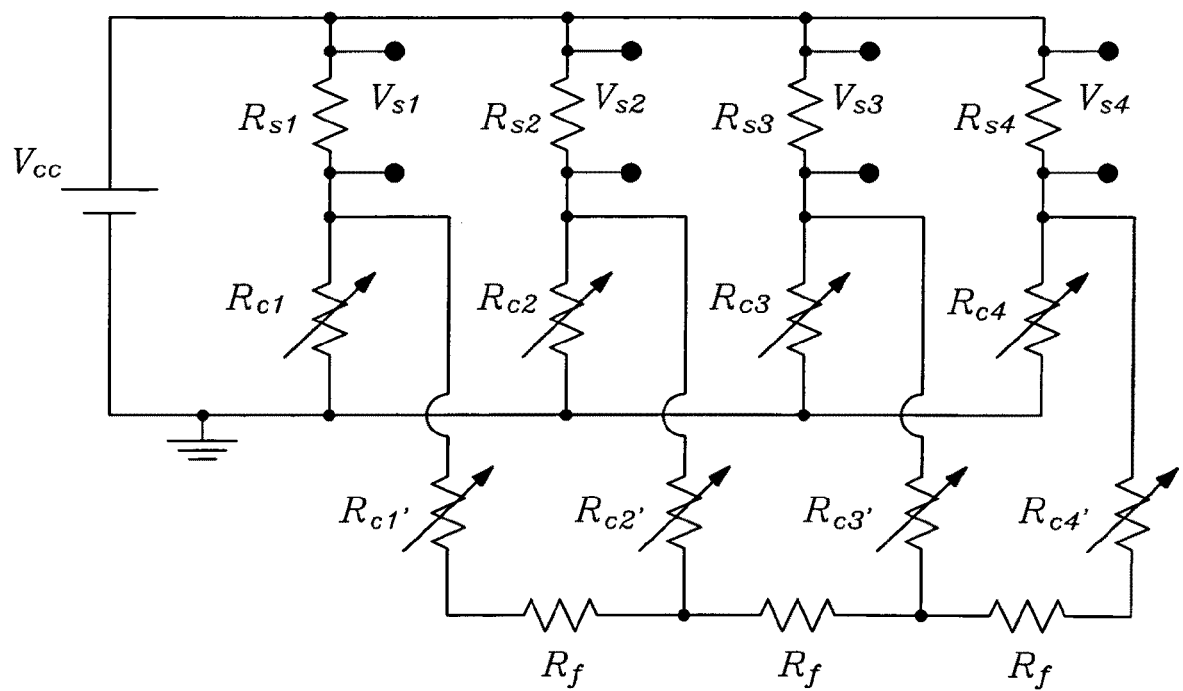
FIG. 28 is an electrical schematic showing a simplified model of a multichannel resistive pulse sensor embodiment.

A simplified electrical circuit equivalent of the measurement setup is shown in FIG. 28. The measurement electrode in the center of a sensing channel divides that channel into two equivalent resistances $R_{ci}$ and $R_{ci'}$ (i=1, 2, 3, 4). The first half of each microchannel ($R_{ci}$) serves as a sensing channel, while the second half of each microchannel serves as an isolation resistor to reduce or eliminate crosstalk among channels. When a particle passes through channel i, it affects first the equivalent resistance of the first half of the channel $R_{ci}$, and then the equivalent resistance of the second half $R_{ci'}$. The change is dependent on both the particle's size and amount of surface charge. $R_{si}$ is the sampling resistor of the microchannel, across which the recorded voltage $V_{si}$ is measured. $R_{si}$ is the resistance formed by the electrolyte between two adjacent microchannels. This resistance is usually small compared to microchannel resistance and is therefore neglected.

One challenge for using multiple sensing channels is the electronic coupling or crosstalk among channels because the electrolyte electrically connects all channels. When one particle passes through a microchannel, it generates a resistance change in this channel. Because all channels are electrically connected, a resistance change in one channel can cause a current change in other channels, and in turn induce a voltage change across the sampling resistors of other microchannels. This voltage change can be translated into a change in resistance signals of other channels that do not correspond to passing particles, thereby resulting in false detections. The placement of measurement electrodes in the center of microchannels creates an isolation resistor $R_{ci'}$ between each pair of microchannels (see FIG. 28) and reduces the crosstalk.

Figure 29:
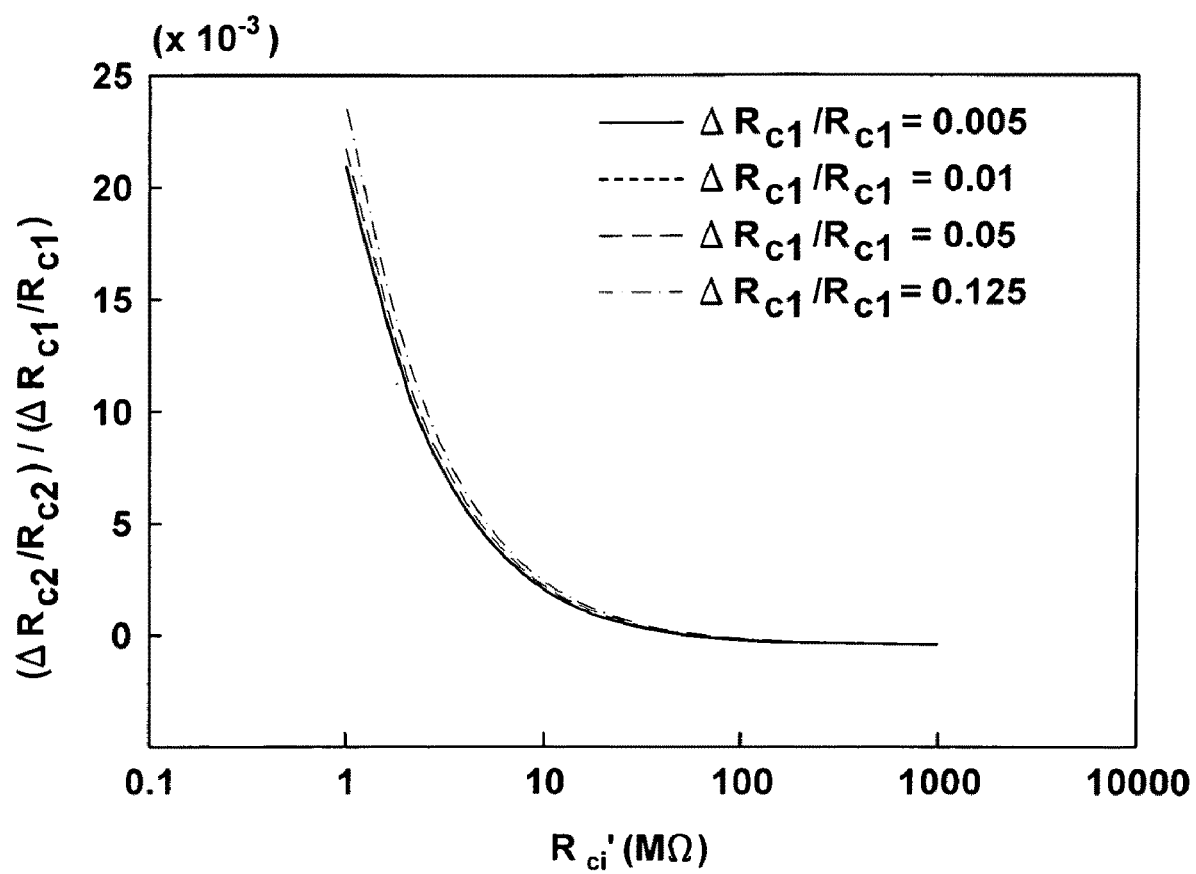
FIG. 29 is a typical crosstalk analysis between adjacent microchannel.

FIG. 29 shows the result of a typical crosstalk analysis of our device using PSpice® (PSpice® can be obtained from Cadence, Inc of San Jose, Calif.) assuming $R_{ci}=R_{ci'}$. When the isolation resistance $R_{ci'}$ is 10MΩ, the relative crosstalk $(\Delta R_2/R_2)/(\Delta R_1 R_1)$ in the adjacent channel (where the crosstalk is maximal) is approximately 0.2% and is considered negligible. As the isolation resistance increases, the crosstalk is further reduced. When $R_{ci'}=100$ MΩ, the cross talk is approximately zero.

The resistance of a microchannel can be estimated by $R=\rho L/A$, where $\rho$ is the resistivity of the electrolyte, L is the length of the microchannel, and A is the cross section of the microchannel. In this work, we use deionized (DI) water, with a resistivity of about $8.33 \times 10^3$ Ω-m, to carry the microparticles. For the microchannel we used, the estimated resistance of the DI water filled-microchannel ($R_{ci'}$) is in the order of 100 MΩ. Thus, the crosstalk is negligible. When the channel size is scaled down to the submicron and nanometer level, according to the scaling law, $R_{ci'}$ will be increased significantly, and thus much less crosstalk is expected. Therefore, some embodiments having nanoscale channels can operate without crosstalk even when using a more concentrated electrolyte having a lower resistivity. This is particularly useful because, concentrated electrolytes are often necessary for carrying certain bio-particles.

The microchannels and reservoirs are fabricated on polydimethylsiloxane (PDMS) using soft lithography, and are bonded to a glass substrate with sputter gold electrodes. Device layout (microfluidic channels and electrodes) can be printed onto transparency films using a high-resolution laser printer. The transparency films can then be used as masks in contact photolithography to generate masters with a negative UV photoresist (MicroChem Corporation XP SU-8 2010, Newton, Mass.) on a glass slide for the channels.

According to one example, a curing agent and PDMS prepolymer (SYLGARD 184 Silicone Elastomer Kit, Dow Corning, Midland, Mich.) are mixed in a 1:10 weight ratio. The prepolymer mixture is degassed in a desiccator with a vacuum pump for one hour to remove any air bubbles in the mixture. Then, the prepolymer mixture is poured onto the master. The master/PDMS stack is cured for three hours at 80° C. on a hot plate. After curing, the thin PDMS replicas are cut and peeled off of the masters. Next, contact photolithography with a positive AZ 4620 photoresist (AZ Electronic Materials, Somerville, N.J.) is presented on another glass slide to create the electrode patterns. Cr/Au (50 Å/3000 Å) sheet films are evaporated on the glass slide. A subsequent liftoff process completes fabrication of the electrodes. The PDMS layer with developed channels and electrodes-embedded glass slide are then treated with RF oxygen plasma (Plasma Etcher PE 2000, South Bay Technology Inc., San Clemente, Calif.) for 25 seconds (50 W, 200 mTorr). This temporarily activates the exposed part of the PDMS and provides very good adhesion. The PDMS replica and glass side are then immediately brought into contact, aligned, and bonded together.

A single measurement channel comprises the half channel resistance $R_{ci}$ in series with the sampling resistor $R_s$ and the supply voltage (see FIG. 27). When a particle passes through the microchannel it causes a change in the half channel resistance, and a corresponding change in the voltage across the sampling resistor. The relative change in resistance of the microchannel in terms of the measured voltage is given by Equation (1), where $V_s^1$ is the measured voltage when a particle is present in the microchannel and $V_s$ is the measured voltage in the absence of a particle in the microchannel.

For a micro-channel with length L and diameter D (see FIG. 28(b)), the change in resistance as a particle passes through it is given by Equation (2), where d is the diameter of the particle, and D and L are the diameter and length of the micro-channel, respectively. The equation holds true when $(d/D)^3<0.1$, as is the case in this embodiment. Thus, the particle diameter can be calculated from the relative change in resistance according to Equation (3).

Figure 30A:
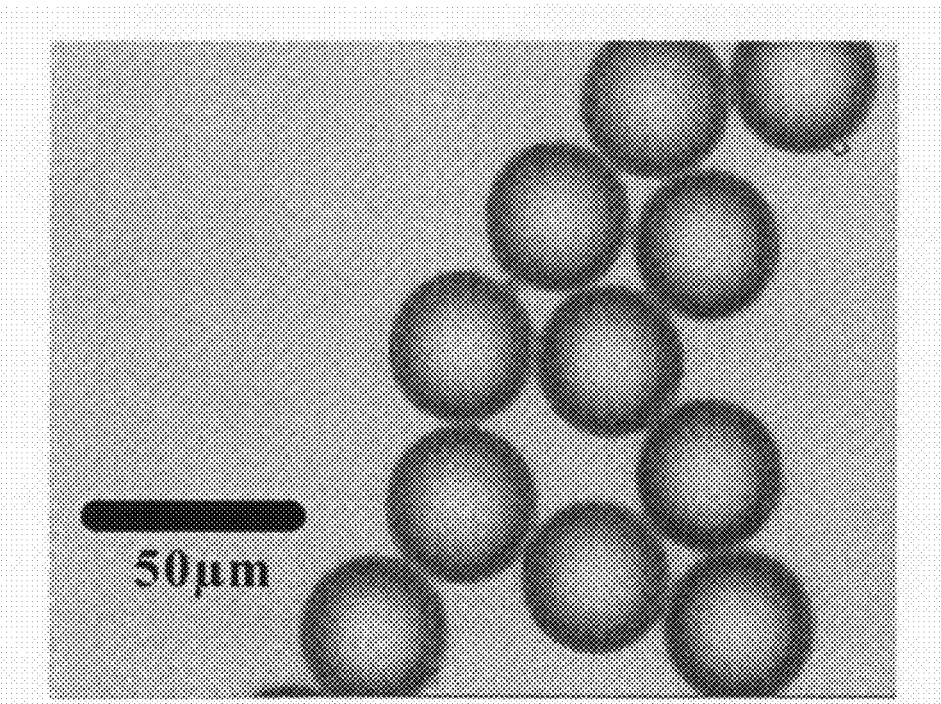
FIG. 30 is a pair of photomicrographs showing (a) 40 μm PM particles, and (b) Juniper *Scopulorum* pollen.
Figure 30B:
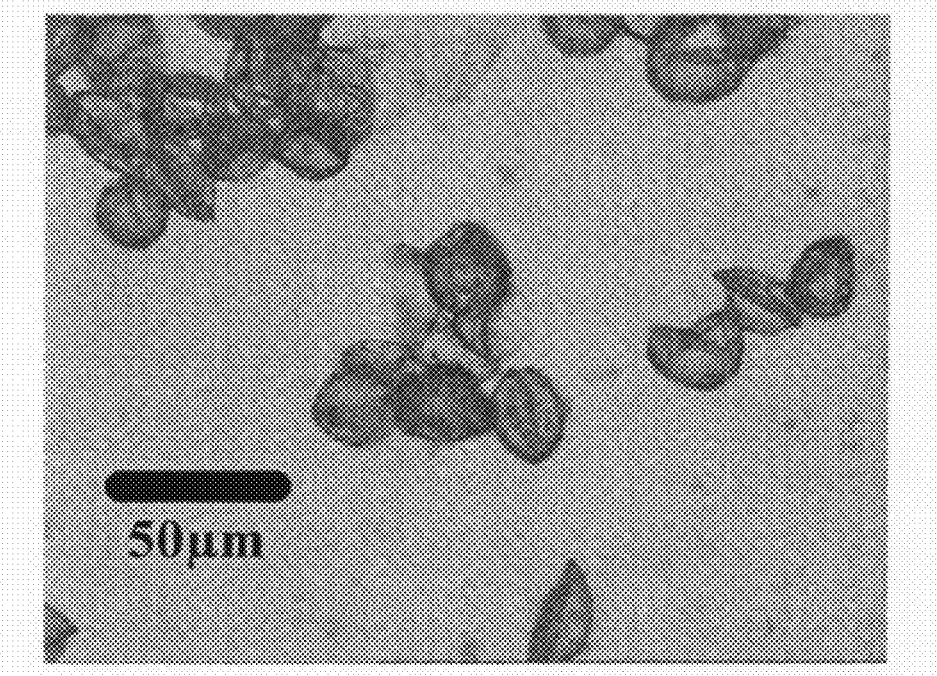

An illustration of this embodiment follows. Polymethacrylate particles with diameters of 40 µm (40 µm±0.8 µm) (Sigma Aldrich Inc.), and Rocky mountain Juniper (Juniper Scopulorum) tree pollens (Sigma Aldrich Inc.) are chosen for the following example. These particles are chosen because they are commercially available and because polymethacrylate particles have well characterized properties. The diameters of pollen particles are determined using high resolution optical microscopy. The Juniper tree pollen is egg-shaped and the diameter ranges from 17 μm to 23 μm. FIGS. 30(a), and 30(b) show photomicrographs of 40 μm polymethacrylate particles and Juniper tree pollen, respectively.

The particle solution is forced to flow through microchannels of the present invention by application of a pressure difference with a syringe. An applied voltage of $V_{cc}=6V$ is applied across the microchannels. Due to the polarization effect of gold electrodes, such a high source voltage is necessary to ensure that there is sufficient current/electric field within the electrolyte to record a noticeable voltage change across the sampling resistors. Voltage measurements are made across a sampling resistor $R_s=100$ kΩ. The voltage trace is recorded for four channels using a National Instruments NI-6220 data acquisition board, with a sampling frequency of 50 kHz.

The application of a 6V DC voltage on the electrodes in electrolyte can, in some cases, cause electrolysis of water and generate gas bubbles. The gas bubbles can result in false peaks when they pass through the microchannel. No such bubbles are observed in this example.

Figure 31:
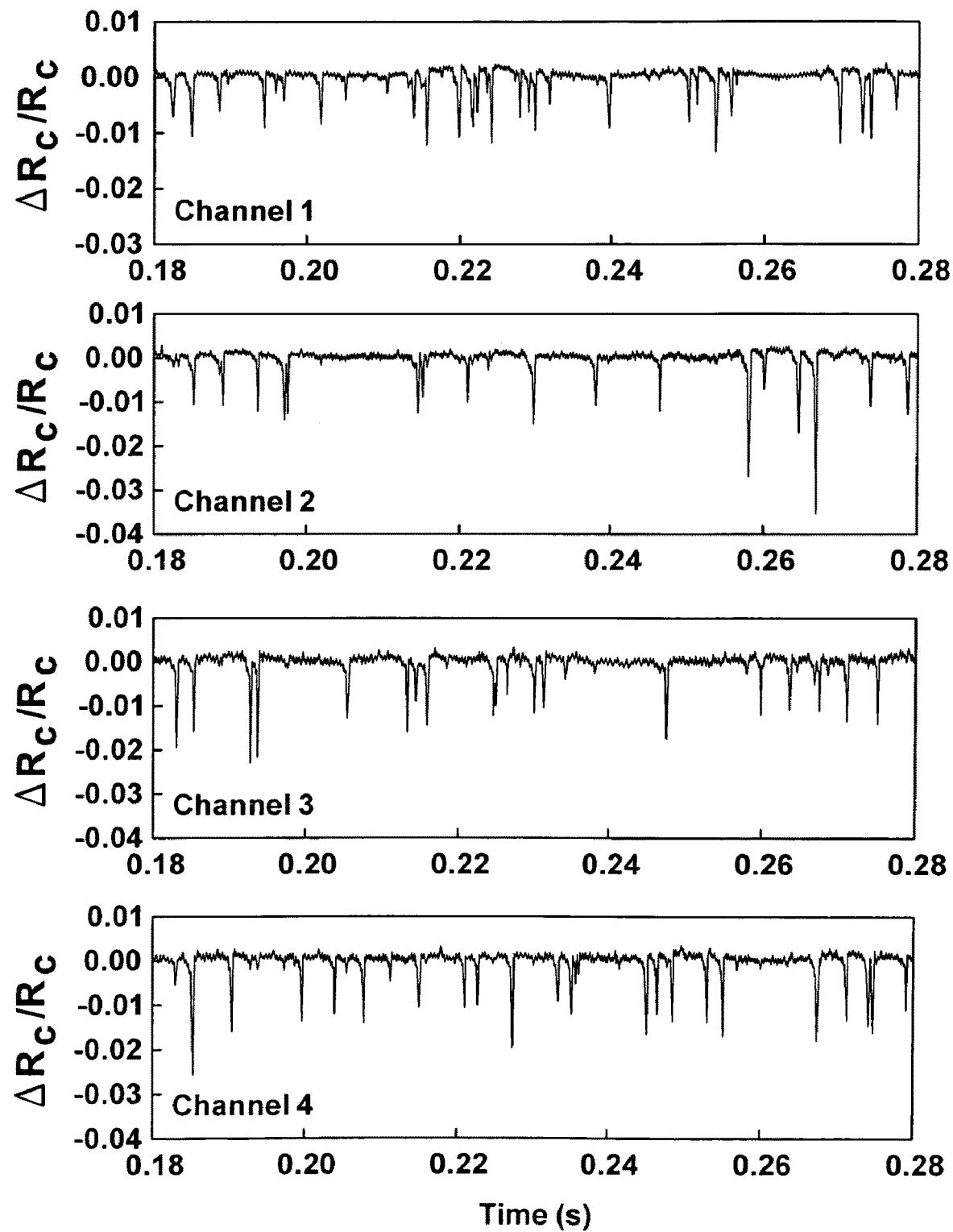
FIG. 31 is a set of plots showing typical relative resistance traces from four channels.
Figure 32:
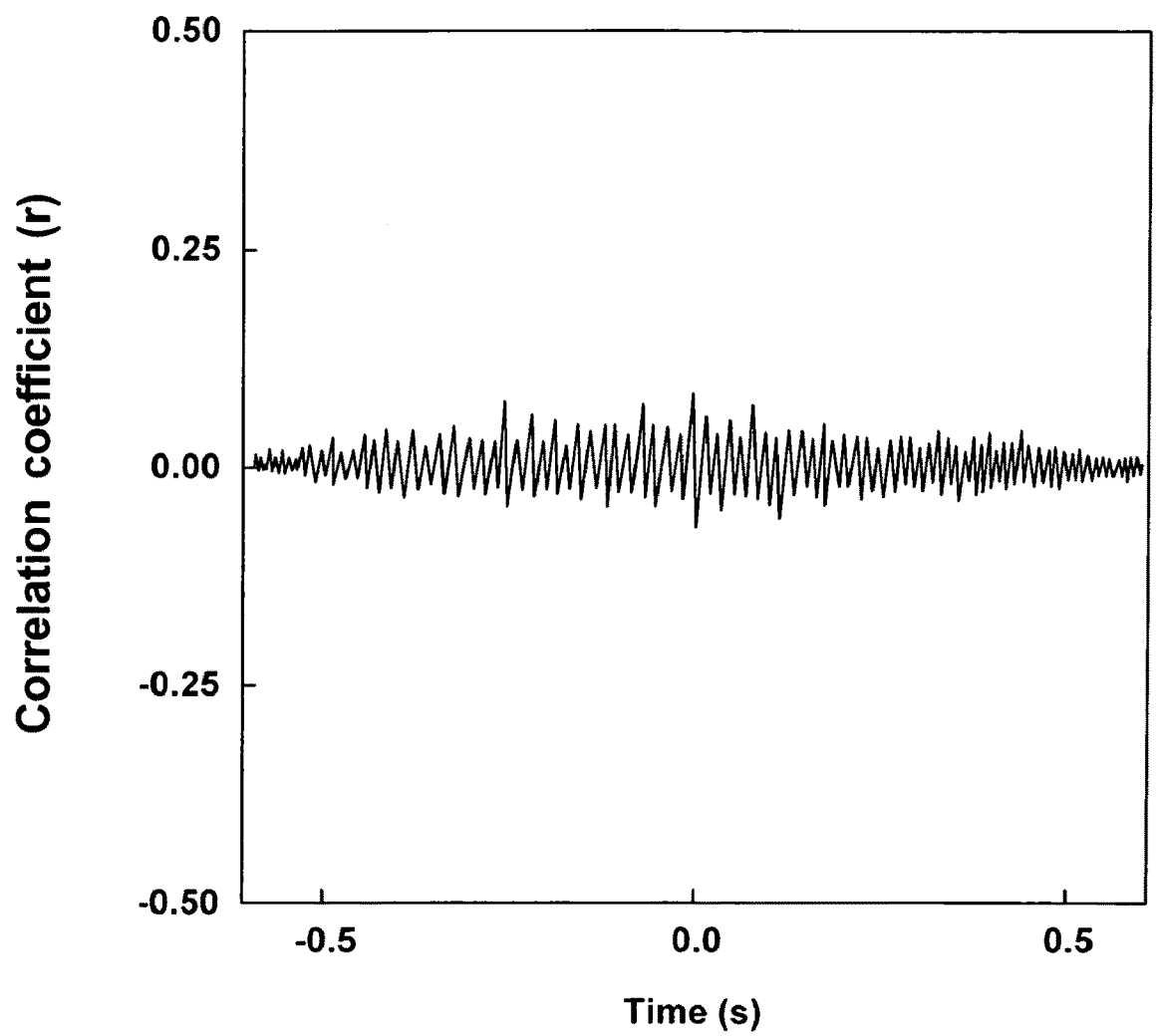
FIG. 32 is a typical cross correlation analysis for adjacent channels.

The Juniper pollen particle solution is prepared by diluting 10 mg of Juniper tree pollen in 10 mL of water. FIG. 31 shows the relative resistance change of the four channels as a function of time. Resistance is calculated by converting it from voltage traces measured across the four sampling resistors using Equation (1). Each resistive pulse represents one pollen particle passing through a microchannel. The resistive traces show pulses appearing in random sequence. A cross correlation analysis is performed between the signals from two sensing channels at a time. The results are shown in FIG. 32. These results show that the cross correlation coefficients |r| are all less than 0.1, indicating there is negligible correlation among the pulses of different channels. Thus, the four sensing channels are able to simultaneously detect and count particles with negligible crosstalk among channels.

It is obvious from FIG. 31 that the resistive pulses caused by Juniper pollens are all downward, that is, when a pollen particle passes through the microchannel, the microchannel resistance decreases. This is possibly because of the high surface charge of pollen particles. This phenomenon can be explained in terms of the surface charge of particles, and can be used to distinguish between particles with different surface charges. Notably, the pulses of the Juniper pollen vary in height. Although not wishing to be bound to any one theory, the variation might be attributed to the particle size variation and the egg-shape of Juniper pollen.

Figure 33:
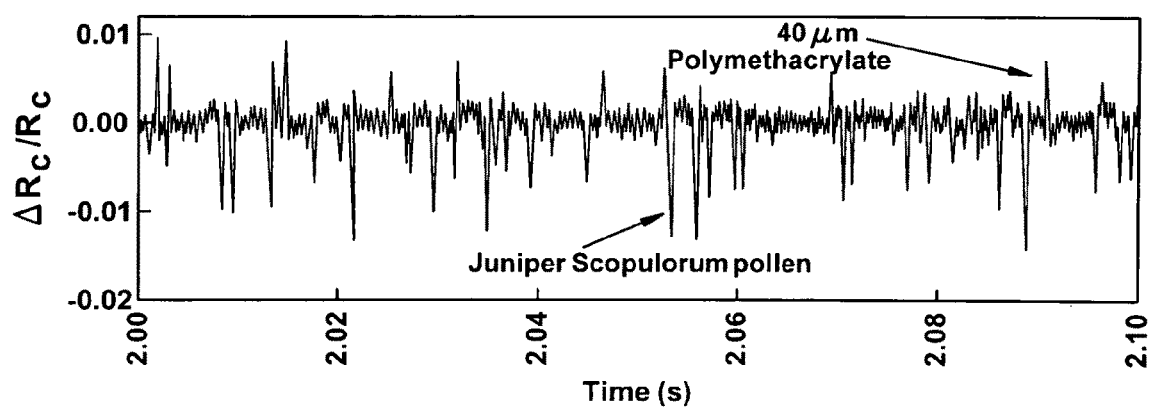
FIG. 33 is a typical relative resistance for a mixture of Juniper pollen and 40 μm PM particles in a one-channel embodiment.
Figure 34A:
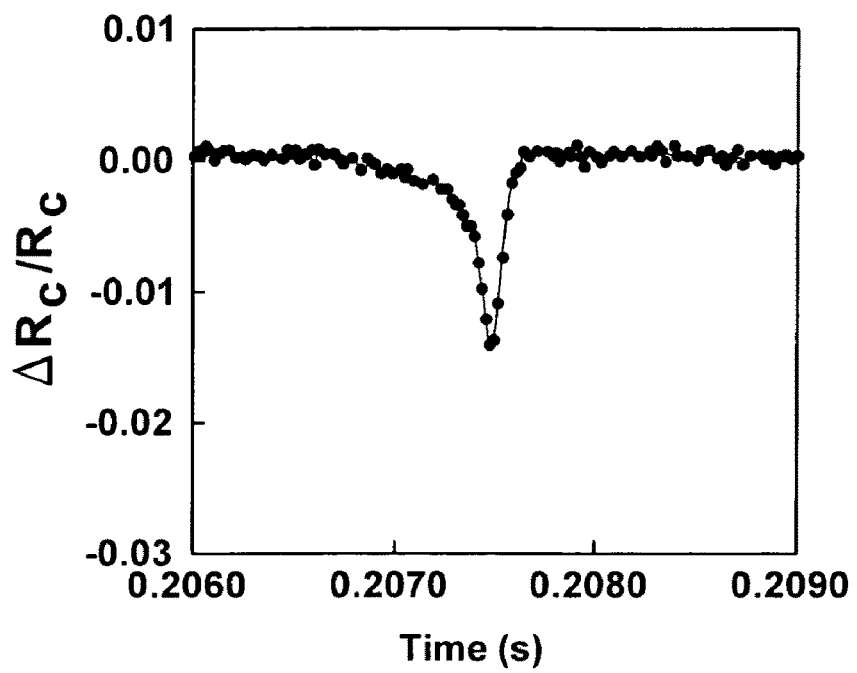
FIG. 34 is a pair of magnified resistive pulses due to (a) Juniper pollen, and (b) 40 μm PM particles.
Figure 34B:
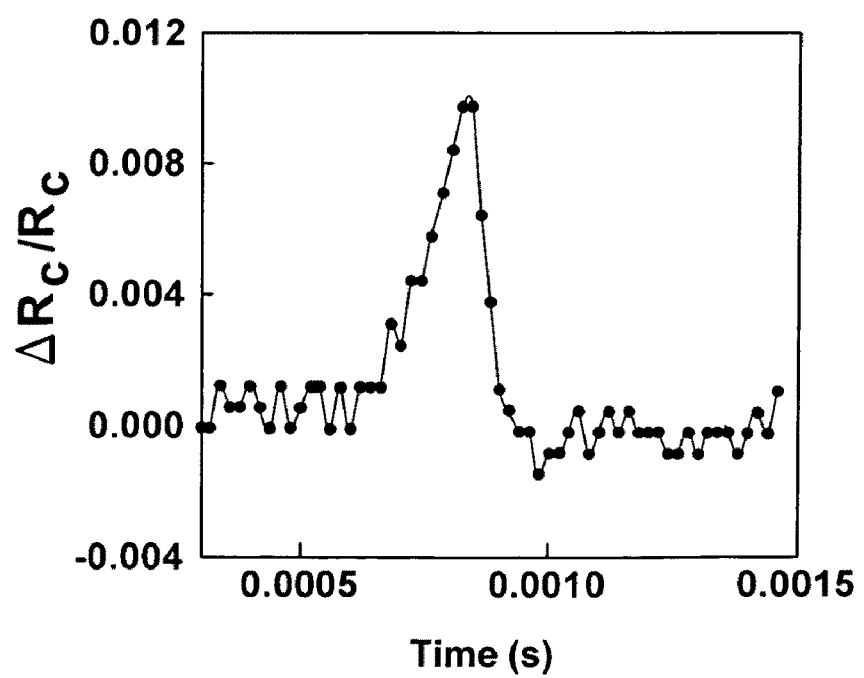
Figure 35:
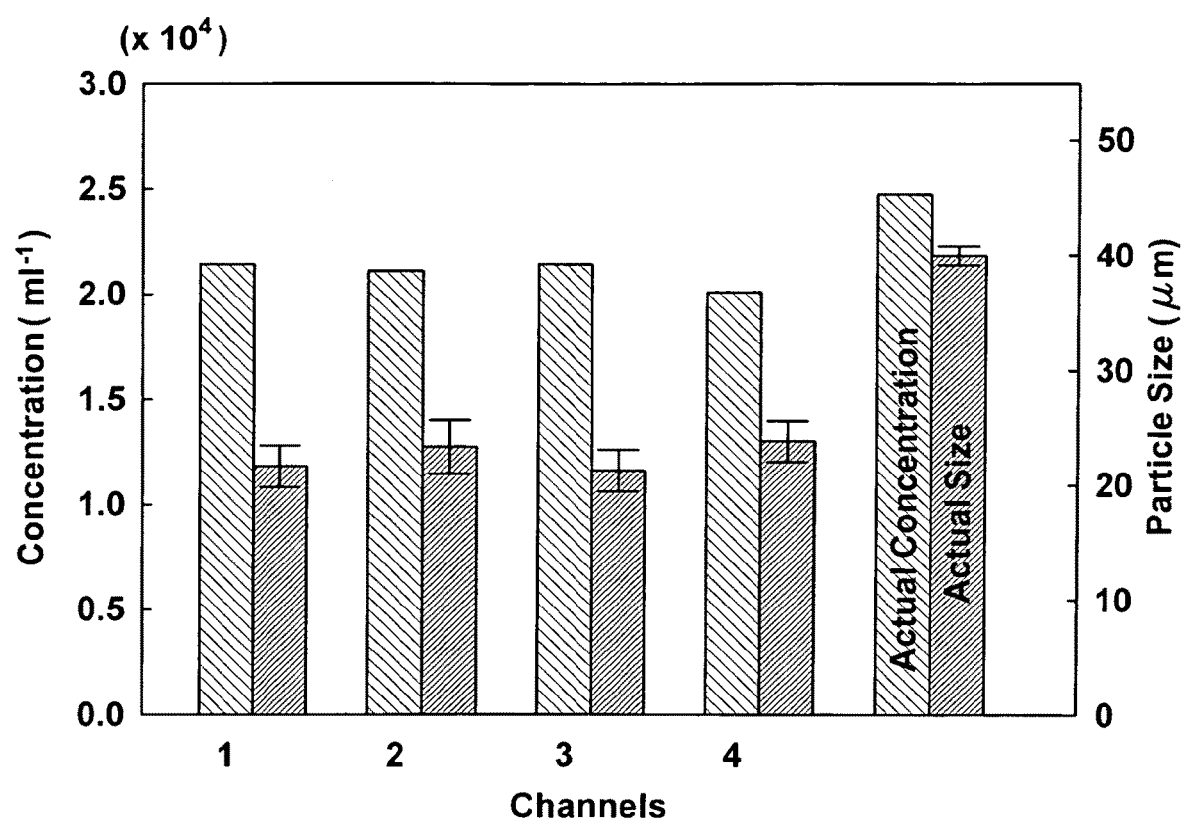
FIG. 35 is a graphical summary of the measured diameter and concentration of 40 μm PM particles in a mixture.

Polymethacrylate particle solution (10% solid) 0.1 mL of 40 μm, and 10 mg Juniper pollen are mixed in 10 mL DI water and are tested in a multichannel embodiment. The resulting concentration of 40 μm polymethacrylate particles is $2.49 \times 10^4$ mL$^{-1}$. Voltage traces across the sampling resistors are recorded. A typical resistive pulse trace in one channel (channel 3) is shown in FIG. 33. The resistive trace is converted from the voltage trace signal. Magnified resistive pulses generated by Juniper pollen and 40 μm polymethacrylate particle are shown in FIG. 34. According to these results, pollen generates downward resistive pulses, while polymethacrylate particles generated upward resistive pulses. Thus, we are able to differentiate and count the two particle species. The concentration of the 40 μm polymethacrylate particles in the four channels is calculated from counting the number of upward peaks during the period of one second. The concentrations are calculated to be $2.15 \times 10^4$ mL$^{-1}$, $2.11 \times 10^4$ mL$^{-1}$, $2.14 \times 10^4$ mL$^{-1}$, and $2.01 \times 10^4$ mL$^{-1}$ for channels 1, 2, 3 and 4, respectively. These results are shown in FIG. 35. The measured particle concentration in each channel is lower than the estimated particle concentration, which is $2.49 \times 10^4$ mL$^{-1}$. This may be due to some PM particles depositing onto the substrate during the experiment.

The particle diameters are calculated from resistive pulse data shown in FIG. 33 using Equations (2) and (3). Using the nominal sensing microchannel dimension of 50 μm×100 μm×150 μm, the analysis shows the estimated particle diameter is 20.1±1.8 μm, 20.4±1.5 μm, 22.0±2.1 μm, and 22.4±1.8 μm for channels 1, 2, 3 and 4, respectively (see FIG. 35). The large difference between the calculated and the actual particle diameter (40 μm±0.8 μm) is mainly because of the polarization effect that takes place on the gold electrodes. In electrolyte solution and DI water, electrode polarization causes the DC voltage applied on electrodes be dropped across the double layers of the two electrodes. Thus, the voltage drop across the bulk solution is less than the actual applied voltage, resulting in underestimated particle dimensions when Equation (3) is used. The electrode polarization can be reduced by using Ag/AgCl electrodes with large surface areas.

IV. Automated Continuous Aerosol Sampling and Coulter Counting-Based Bio-Aerosol Detector System Embodiments Another embodiment includes a rapid, integrated, particle screening device consistent with the design set forth in FIG. 4. The embodiment comprises a bio-aerosol sampler for collecting airborne pollen and combining it with a liquid, such as DI water. The embodiment also includes a multichannel Coulter counter for rapid detection and counting of particles. According to one version of this embodiment, an air sampling system can be included. Some embodiments can also include continuous automated aerosol monitoring. One very specific embodiment includes the Biosampler air sampling system from SKC Inc. Some embodiments are self cleaning and can be integrated with a Coulter counter. According to some embodiments, and in keeping with FIG. 4, a sampling bottle can be connected to a reservoir of DI water, and a flow of liquid from the bottle can be directed to a multichannel Coulter counter. Some embodiments are also capable of recycling the DI water and/or self-cleaning the DI water, thereby extending the potential duration of unattended operation. According to some embodiments an air sample can be pumped through a particle separation and/or collection pipe.

Figure 36:
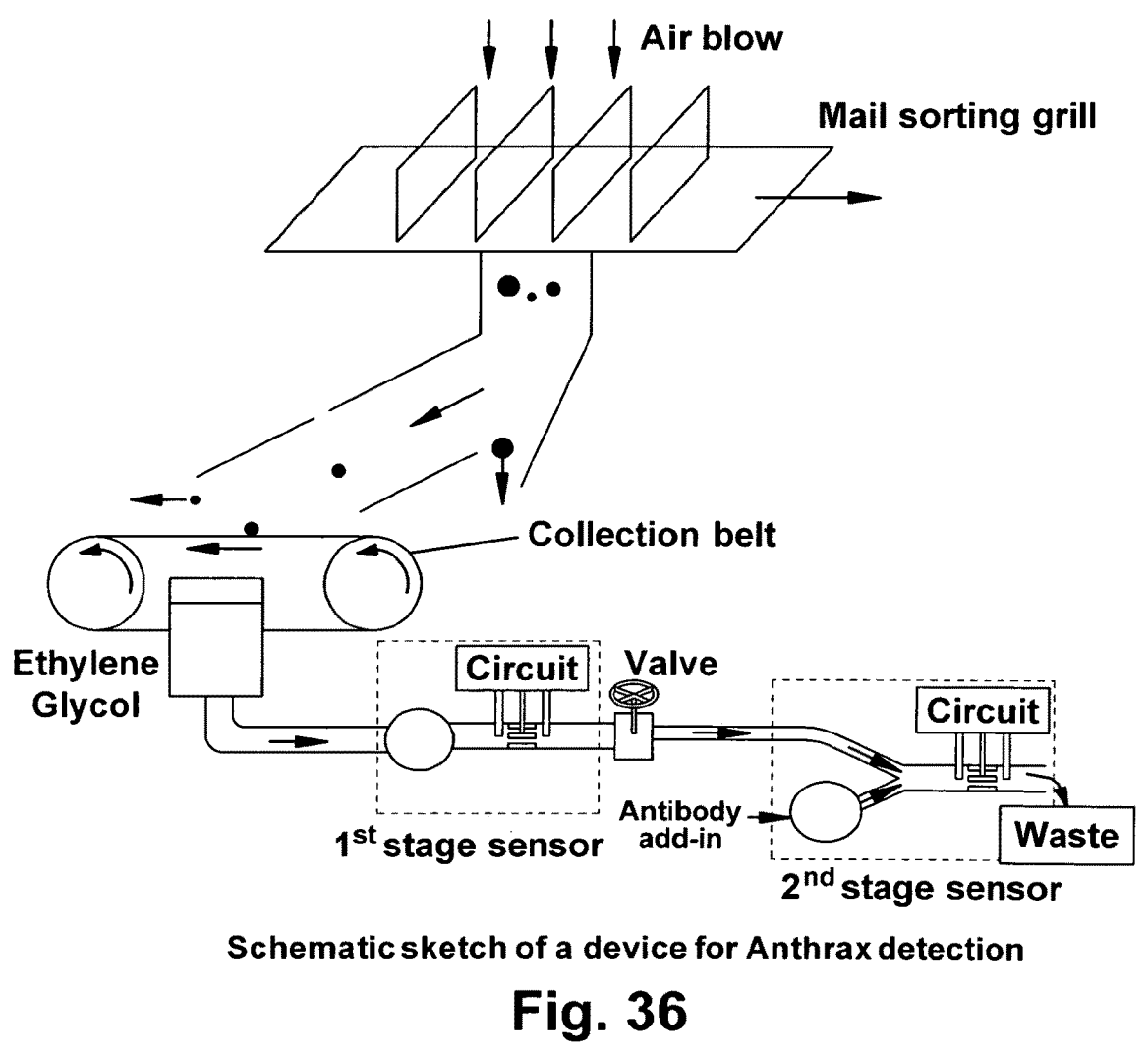

According to one embodiment anthrax spores can be detected in mail during processing/sorting of the mail. Some embodiments may offer a cheaper and/or more rapid detector of anthrax in mail room applications. FIG. 36 shows a drawing of one example of this embodiment. The envelopes on the mail sorting grill are subjected to a generally perpendicular air flow from, for instance, a blower. The particles on the envelopes, including medium size anthrax spores (a few microns), large dust particles (a few tens of microns or larger) and small dust particles (sub microns or less) are swept off the envelops and carried by the air flow to one or more collection devices.

Figure 37A:
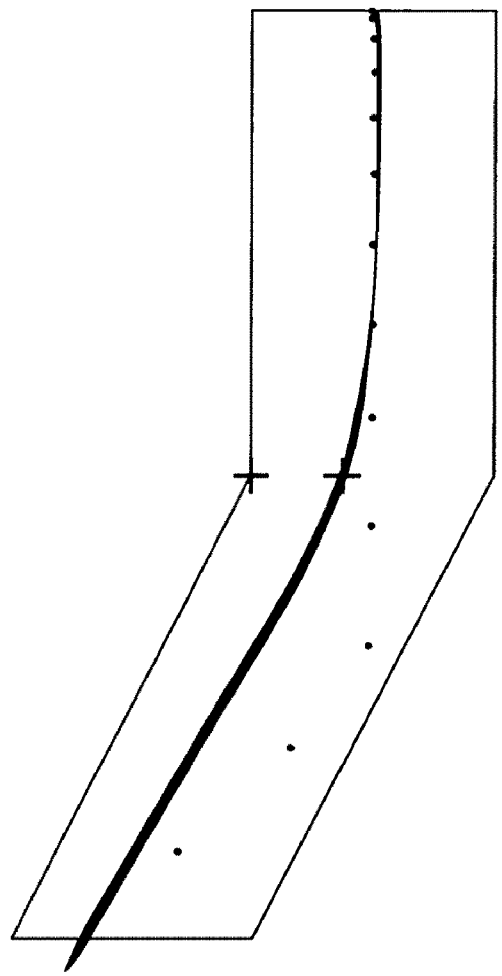
FIG. 37 is a fluid dynamics simulation of the behavior of (a) 1 mm and (b) 1 μm particles in a fluid flow having a 10 m/s inlet velocity.
Figure 37B:
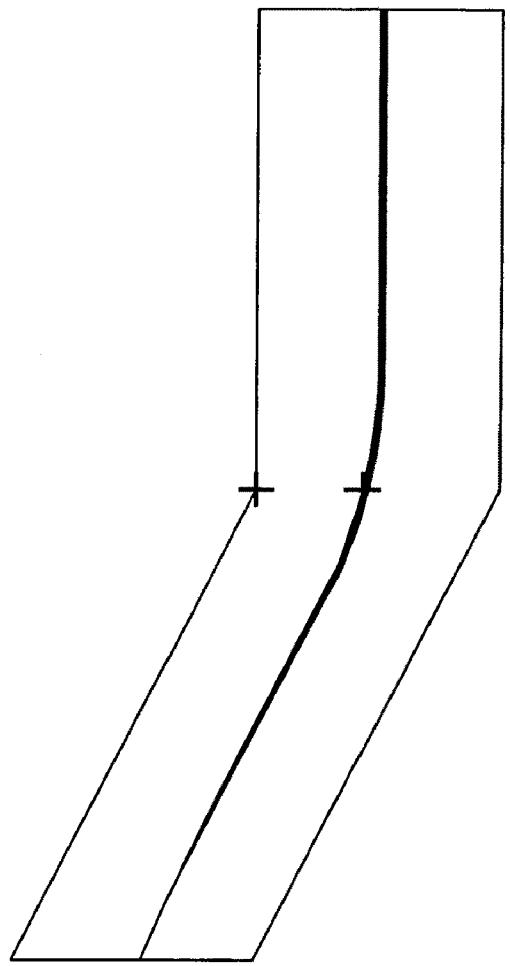

En route to the collection device, the air flow is subjected to a sharp turn through a flow channel. The larger and/or heavier particles, such as dust particles, are separated and exit at an elbow or bend in the channel, while the medium sized and small sized particles continue toward the collection device. FIGS. 37(a) and 37(b) show fluid mechanics simulation results of particle behavior in such embodiments where the inlet velocity is about 10 m/s. Specifically, FIG. 37(a) shows that particles having diameters of about 1 mm are separated at the elbow. The dots that depart from the central line in FIG. 37(a) represent the separating particles. Heavier/larger particles tend to separate, while smaller/lighter particles tend to be guided by the air flow. FIG. 37(b) shows the average path of particles having diameters of about 1 micron.

Next, the air flow is directed to, and impinges, a moving collection belt. Mid-sized particles, including anthrax, adhere to the surface while smaller particles remain in the air flow, which turns parallel to the collection belt. The collection mechanism is similar to known particle sorting methods, such as virtual impactors. In one embodiment, the movable belt transports captured particles to an ethylene glycol tank. The tank both collects the particles, and provides continuous wetting of the collection belt thereby enabling particle capture. Unlike water based electrolyte solutions where water evaporates faster, using ethylene glycol as the electrolyte diminishes the need to constantly compensate evaporative losses.

After the particles are collected, the solution is transported to the first stage multichannel Coulter-type sensor. Because of the relatively large volume of analyte, a multichannel Coulter counter is used thereby enabling rapid analysis of analyte solutions. Anthrax spores are heavily charged bioparticles. Therefore, the first stage Coulter counter is able to distinguish them from dust particles without the need to add costly antibodies.

It is desirable that anthrax detectors minimize false positives. Therefore, some embodiments can include a second stage Coulter sensor to further diminish the chances of false positives. If the first stage sensor detects suspicious particles, the second stage verifies whether the particles are anthrax. In one embodiment, the second stage includes a valve that can be used to direct electrolyte solutions containing suspicious particles to a second stage sensor. According to some embodiments, bioselectivity can be enhanced by using monoclonal antibodies that bind to the anthrax spore specifically. Binding to a monoclonal antibody causes a change in the size and surface charge of anthrax spores, which can be identified by the Coulter counter detector.

Some embodiments are capable of detecting a single anthrax spore in a liquid analyte. Some embodiments may also include multiplexing technology that significantly improves the signal-to-noise ratio of the analytical signal.

Some embodiments are suitable for mass production and can comprise a low-cost and/or portable device. Some embodiments may be suitable for rapid on-site aerosol particle analysis. Some embodiments may require no complex setup, and/or no enrichment of the analyte prior to contacting the detector, or other preparation of the analyte.

Some embodiments can comprise high throughput bioaerosol instrumentation. Some embodiments can comprise a large number of channels in one chip and thus allows real-time detection of anthrax spores.

According to some embodiments, the detector is capable of counting each spore, bacterium, and/or virus in the collection electrolyte solution. Thus, sensitivity can be below 100 CFU/liter. Some embodiments can deduce size, shape, and/or surface charges based on current measurements with greater than 99% confidence. According to some multi-channel embodiments detection efficiency and/or response time is greatly improved. For example, response time can be less than one minute. Furthermore, some embodiments comprise a substantial dynamic range, enabling detection of a wide variety of sizes of particles. According to some embodiments, integrated micromachined devices can allow small size (e.g. <1 cu. ft) and low unit cost (e.g. about $1000/unit). Some embodiments can enable high reliability, low maintenance and/or operating cost (e.g. less than about $1000/year).

Some embodiments are capable of the same or better selectivity as compared to immunoassays. However, unlike most common immunoassay methods, which require antibodies to be labeled (e.g. using fluorescence, radioactivity, or enzyme activity), some embodiments are capable of operating without such labels. Thus, the device is relatively inexpensive to use. According to some embodiments, operating costs can be limited by using a two-stage sensor system, where the second stage (i.e. the antibody stage) is active only when the first stage sensor sends an alarm signal indicating a suspicious signal has been detected.

V. Multiplexed Multichannel Coulter Counter Embodiments

Some embodiments comprise piezoelectric bimorph microactuators. Such actuators can be bonded, for example, to the outside of each microchannel to dynamically control the flow, thereby modulating the electrical impedance of the microchannel. In some embodiments, bimorph actuators can be a cantilever made of two different materials bonded together in such a way that when one layer deforms in response to an applied voltage, the cantilever bends. In some embodiments, the bimorph actuators also allow the effective size of the microchannel to be changed, for instance, to match the size of tested particle, thereby improving the range of particle sizes that the Coulter counter can detect.

Figure 38:
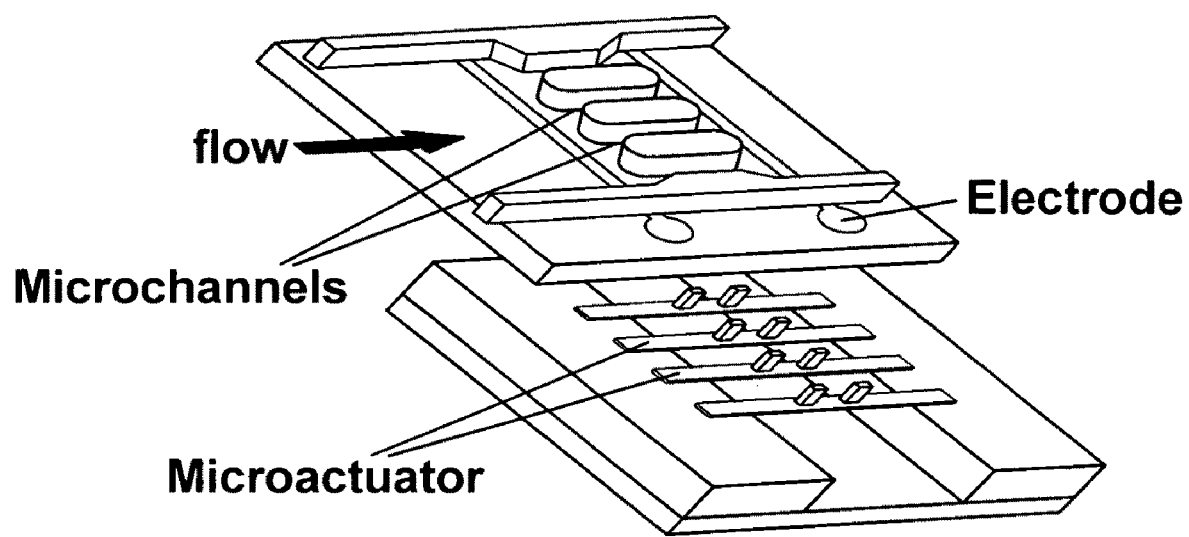
FIG. 38 is a schematic view of a microfluidic chip and a microactuator chip embodiment before bonding.

One embodiment comprises a four-channel Coulter counter, as shown in FIG. 38. The four-channel Coulter counter comprises two chips: a microfluidic chip and actuator array chip. In the microfluidic chip, reservoirs and microfluidic channels can be microfabricated by depositing polydimethylsiloxane (PDMS) to form desired geometries. Two electrodes can be located in the two major reservoirs for applying a constant voltage across the channels and/or for taking measurements. Electrolyte solutions containing particles are forced to move from the inlet reservoir to the outlet reservoir through the four sensing channels. In order to dynamically modulate the microchannels, the bottom channel wall can comprise a thin (e.g. about 50 μm) PDMS membrane. PDMS is a soft material (Young's Modulus of cured 10:1 Sylgard 184 from Dow Corning is about 2.5 MPa) and it can be easily deformed. PDMS microchannels can be modulated with mechanical pins actuated by piezoelectric bimorph.

Figure 39A:
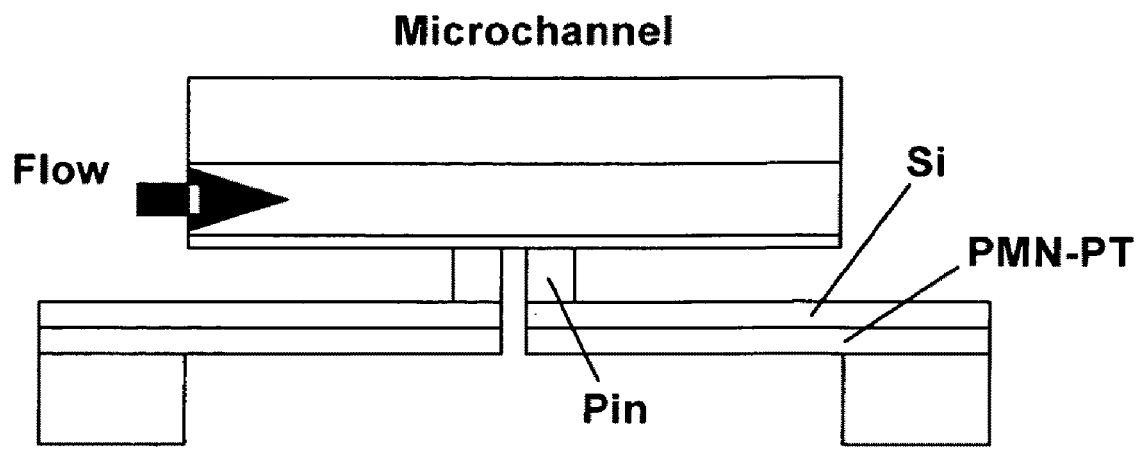
FIG. 39(*a*) is a schematic view of an actuator embodiment comprising PMN-PT/Si bimorph and pin element bonded to a microchannel.
Figure 39B:
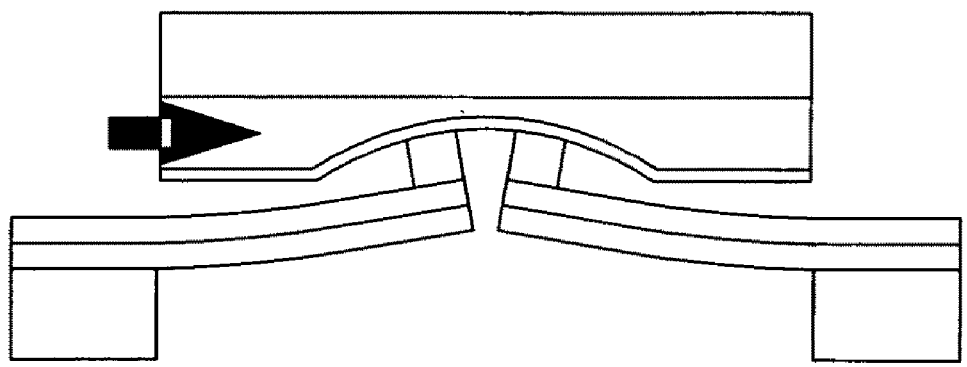
Figure 39C:
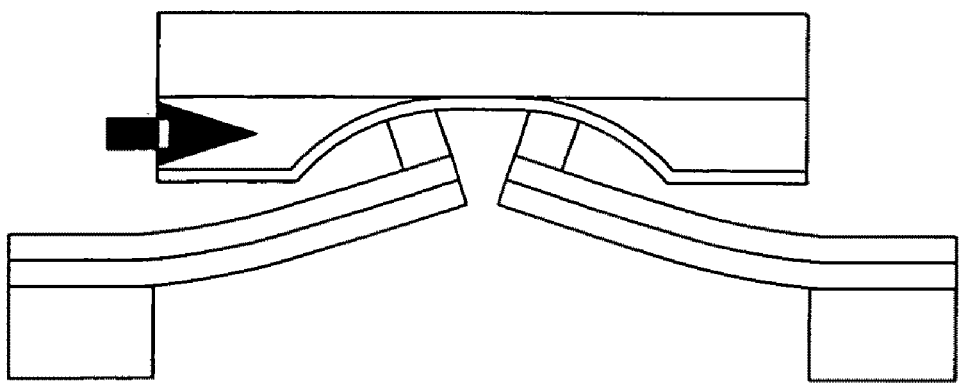

In order to modulate the channel signals, a microactuator array can be bonded to the microchannels and used to mechanically modulate the sizes of the microchannels. FIG. 39 shows a schematic view of an actuator cell, which comprises a single crystal PMN-PT/Silicon bimorph actuator forming the active layer, and a pin structure as the linkage to the microchannel. In some embodiments the bimorph actuator can comprise a plurality of layers including two, three or four layers. In embodiments having four layers, the PMN-PT single crystal can be sandwiched between two electrodes (not shown), atop which is single crystal silicon (e.g. with a thin oxidation layer).

According to some embodiments, the pins are fabricated onto the bimorph actuator at the cantilever ends. The PMN-PT layer can be active in the sense that when a voltage is applied it deforms axially. Since the silicon and PMN-PT layers are sandwiched together, the free axial deformation of the top layer (e.g. Si) is constrained by the substrate layer (e.g. PMN-PT) and, as a result, the composite beam bends. The resulting deformable shape of the beam is the one shown in FIG. 39(b). The bending is converted to a normal displacement on the pin, which in turn causes deformation of the microchannel wall. In general, the fast response of piezoelectric actuators enables the microchannels to be modulated on and off with very high frequency. In turn this may enable the multiplexing of measurement signals as a particle traverses a channel.

According to some embodiments, the microactuator array is independent of the microfluidics and thus does not disturb the electrical measurements. By accurate control of the voltage applied to individual actuator cells, the microchannel membrane can also be deformed to decrease the size of the microchannel rather than closing it completely, so as to allow for the detection of smaller particles (e.g. compare FIGS. 39(b) and 39(c)).

Unlike the parallel multichannel devices that measure individual current traces for each channel, some embodiments are capable of measuring only the current through the entire system. Thus, according to these embodiments, the measured current is the sum of the response of multiple channels. For example, when a microactuator closes a channel, it blocks the ion current from flowing through the channel. If the microchannels are opened and closed selectively (e.g. in a pattern specified by a Hardmard transform), it is possible to recover the individual channel currents from the measured total system current. According to this embodiment, the ability to close and open channels at a high enough frequency enables the application of the Hardmard transform. Thus, high-frequency switching of the actuator can be used to take several measurements in the time it takes a particle to traverse a channel. The number of channels can be multiplexed in this way depends on the response time of the actuators, the speed of the data acquisition system, and the travel velocity of the particles in the microchannels. Thus, faster actuators enable higher numbers of channels.

Figure 40:
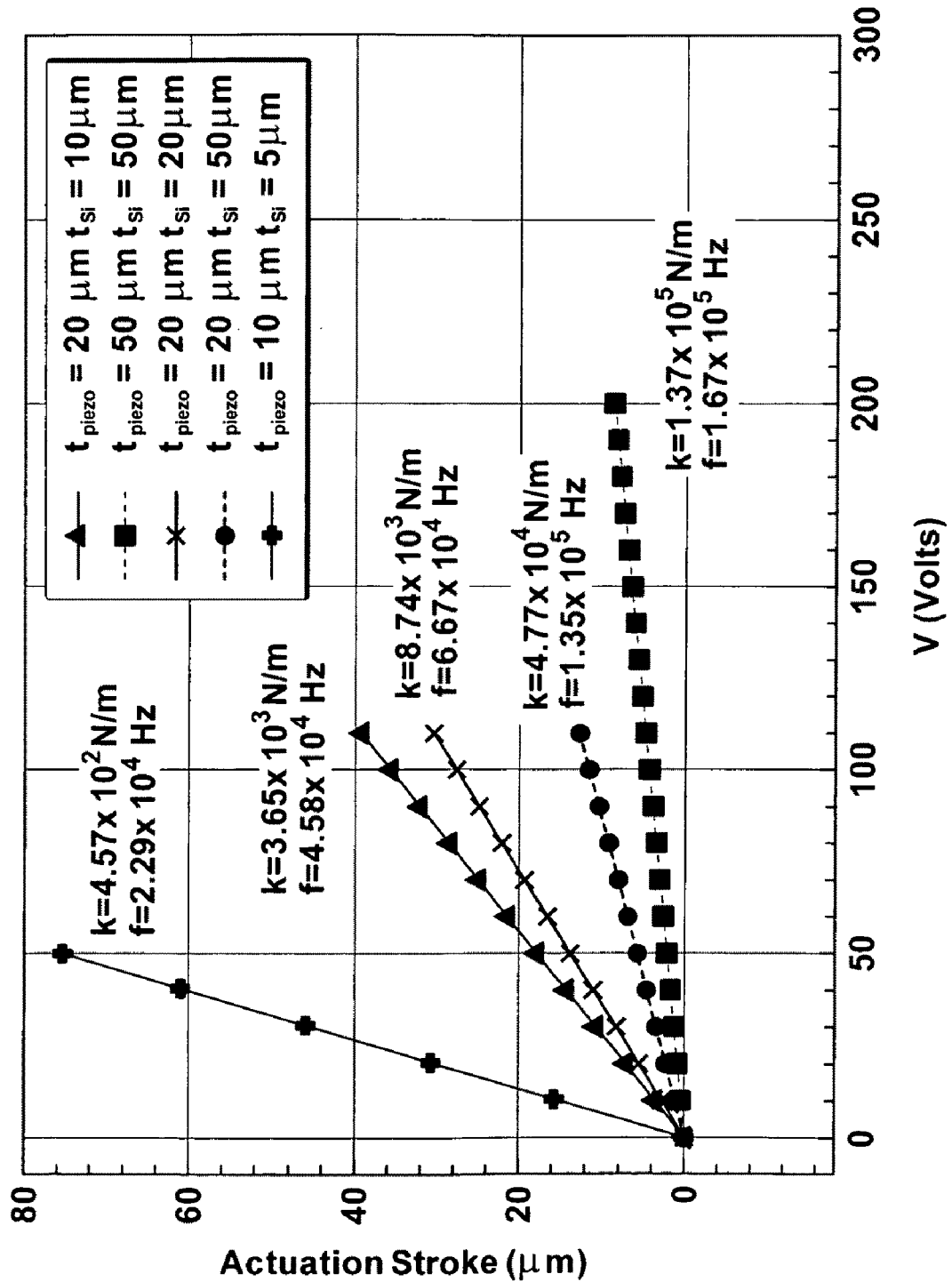
FIG. 40 is a graph of the actuation stroke of a 500 μm long bimorph cantilever versus applied voltage, wherein "k" is stiffness and "f" is the first order natural frequency.

According to one embodiment a biomorph actuator can comprise one or more approximately 500 μm long cantilevers. The cantilevers can comprise a single crystal piezoelectric active layer, and a silicon support layer. According to one embodiment, the boundary conditions can include a cantilever beam clamped at one end and free at the other. The electrode layers can be thin, are therefore not necessarily taken into account. FIG. 40 shows a set of plots of maximum cantilever deflection versus applied voltage for the five different cantilever designs. The calculated stiffness and natural frequency of the bimorph structures are also shown in the figure.

Analyses such as that which is shown in FIG. 40 can be used for estimating actuator performances. FIG. 40 indicates that a PMN-PT/Si bimorph cantilever can be capable of more than a 10 μm tip deflection, which is enough to turn a microchannel off. For example, for a 500 μm cantilever with 20 μm thick PMN-PT and a 20 μm Si substrate, 14 μm deflection is attainable at 50 V, while the natural frequency is 66.7 KHz. For a low voltage design using 10 μm thick PMN-PT and a 5 μm Si substrate, an 18 μm deflection is predicted at 10 V. These results indicate that it is possible for a bimorph actuator to fully mechanically close a channel with a relatively low voltage.

Some embodiments are capable of preventing channel wall rupture by the actuator. According to one embodiment a PDMS channel wall rupture can be avoided by including a corrugated membrane. According to some embodiments such membranes can be fabricated by micromolding.

As would be readily appreciated by one of ordinary skill in the art, the present invention is not limited to PMN-PT actuators, but rather can include any of a wide variety of macro and/or micro actuators that have sufficiently fast responses.

According to some embodiments the foregoing actuators can be used for a wide variety of applications including, without limitation, drug delivery and microfluidic control.

VI. Polymer Brush Conductance Modulation Embodiment

According to another embodiment the conductance within a microchannel is modulated using polymer brushes grown within microfluidic channels. In this regard, the stimuli-responsive behavior of grafted polyelectrolyte brushes in aqueous solution under the influence of an electric field is employed to modulate conductance. A gated function is realized as the polymer brushes transition from an erect state to a collapsed state in response to an external electric field. Based on the same basic design shown in FIG. 38, the polymer brushes are used to modulate individual channels within the device.

Figure 43:
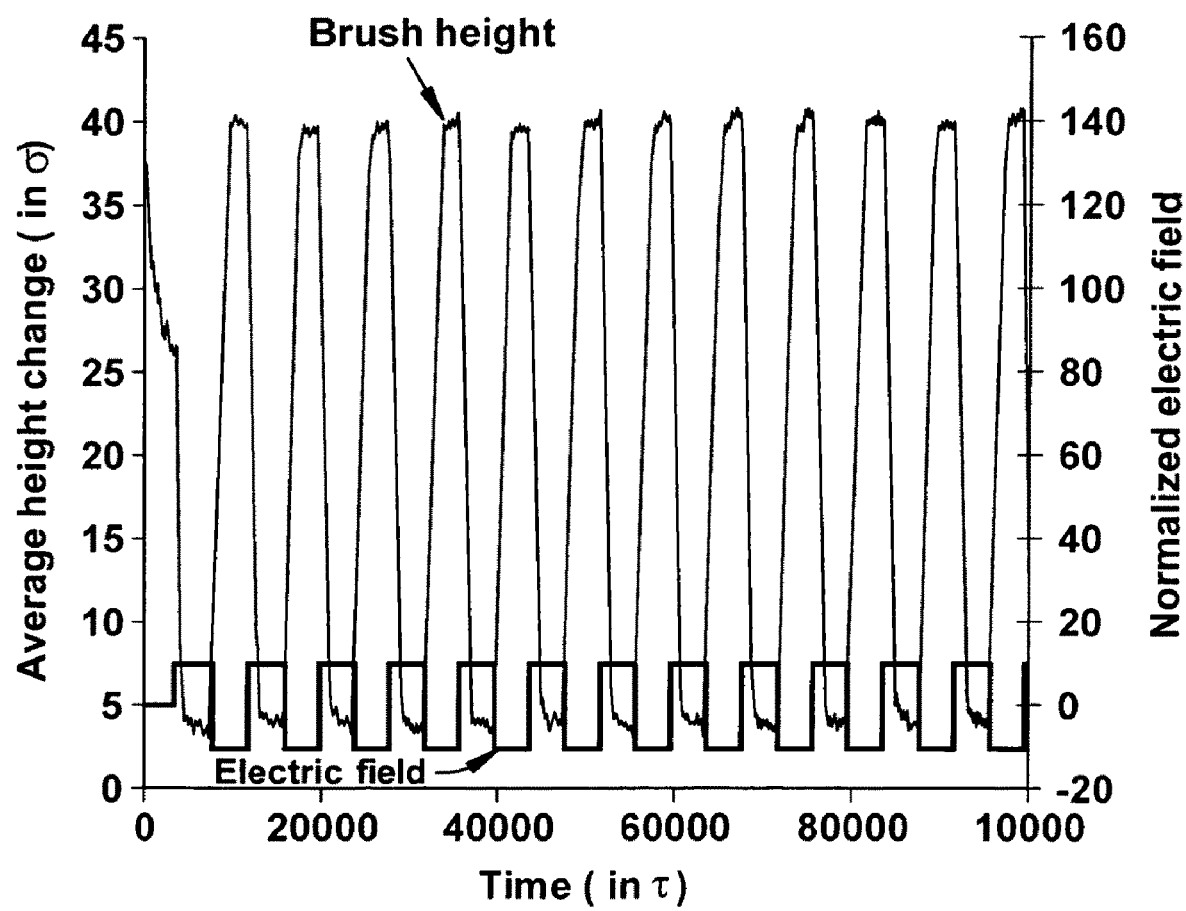
FIG. 43 provides a graph plotting average polymer brush height against change in electric field as a function of time.

FIG. 41 shows the basic design for the polymer brushes. FIG. 41(a) shows the polymer brushes in a collapsed state, and FIG. 41(b) shows the polymer brushes erect or extended in response to a negative electrical field. FIG. 42 provides a simulated view of the three states of freely jointed bead-chain polymer brushes: equilibrium, collapsed and erect. The transition between states requires a critical intensity of the electric field to induce the response and trigger the transition. Under a positive electric field, the polymer chains relax and collapse, forming irregular molecular groups on the channel wall, as seen in FIG. 42(b). Conversely, a negative electric field causes the chains to stretch, as shown in FIG. 42(c). By controlling the electric field direction, or polarity, the transitioning of the polymer chains from erect to collapsed is also repeatably controlled. FIG. 43 provides a graph of the foregoing, plotting average height change of the polymer brush, normalized by Lennard-Jones (L-J) diameter ($\sigma=4$ Å) against electric field change as a function of time in $\tau(\tau=\sqrt{m/\epsilon}$ where m is the mass of one chain segment and $\epsilon$ is the L-J unit of energy.

Based on the foregoing, the morphology of gated polyelectrolyte brushes can be perturbed using electric signals, providing a means to realize biomimetic fluidic/ion channels for a number of varying applications. One such application involves a voltage-gated ion channel suitable for use in coordination with the nervous system. In this instance a number of transmembrane protein helices act coordinatively as a gate and are the primary determinant of the high ion selectivity and precise control of the conductivity. Based on this function, which mimics that of the fluidic/ion channels in biological systems, a new class of advanced gating systems for drug delivery, bioimplants, data storage, smart valves, nano electric devices, and other similar biological applications may be generated.

Electroactive polymer brushes are typically anchored to Au electric contacts by thiol or disulfide based surface anchors. However, such linkages are susceptible to physical and electrochemical degradations, usually within 10 s cycles of cyclovoltammetric scanning. Oxidation of the thiol to sulfonates is attributed to the rapid loss of surface functional groups. To increase the stability of the polymer brushes suitable for repetitive electrochemical modulation of the mechanical properties of the brushes, a special surface anchor based on the 2,4,7-trithia-tricylo[3.3.1.1$^{3.7}$] decane moiety was prepared.

Figure 44:
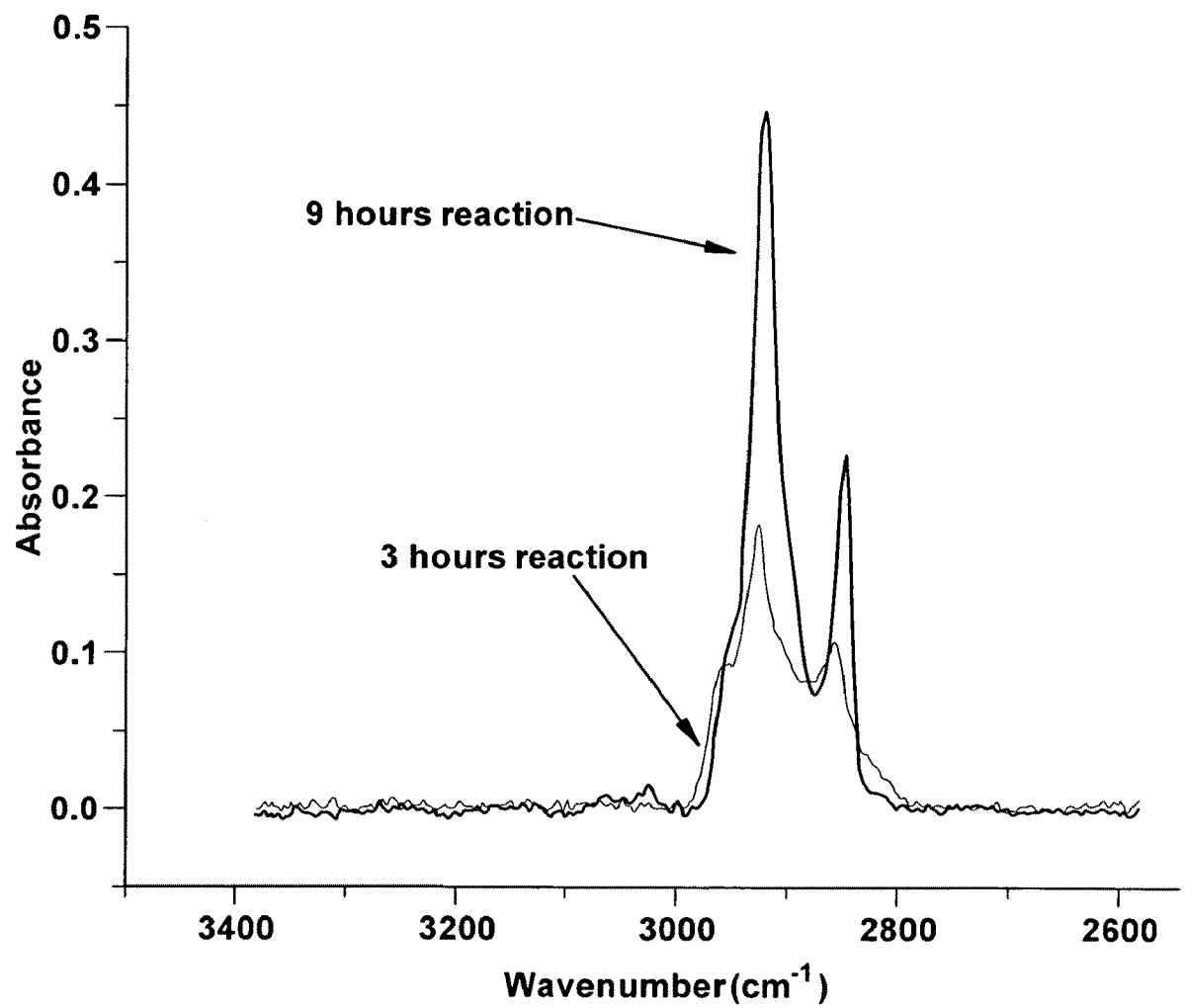
FIG. 44 provides a PM-FT-IRRAS analysis of the hydrocarbon region of a polymer brush grown on Au surface.

To synthesize the polymer brushes in accord with the disclosure provided, surface polymerizations were performed using the following reaction scheme based on atom transfer radical polymerization (ATRP). The formation of the desired polymer brush layer on the electrode surface using this polymerization scheme was confirmed by surface IR spectroscopy, as set forth in FIG. 44. In this Figure, a PM-FT-IRRAS analysis of the hydrocarbon region of the polymer brush growing on a Au surface is provided. The larger trace is the polymer brush after 9 hours reaction and the smaller trace is the polymer brush after 3 hours.

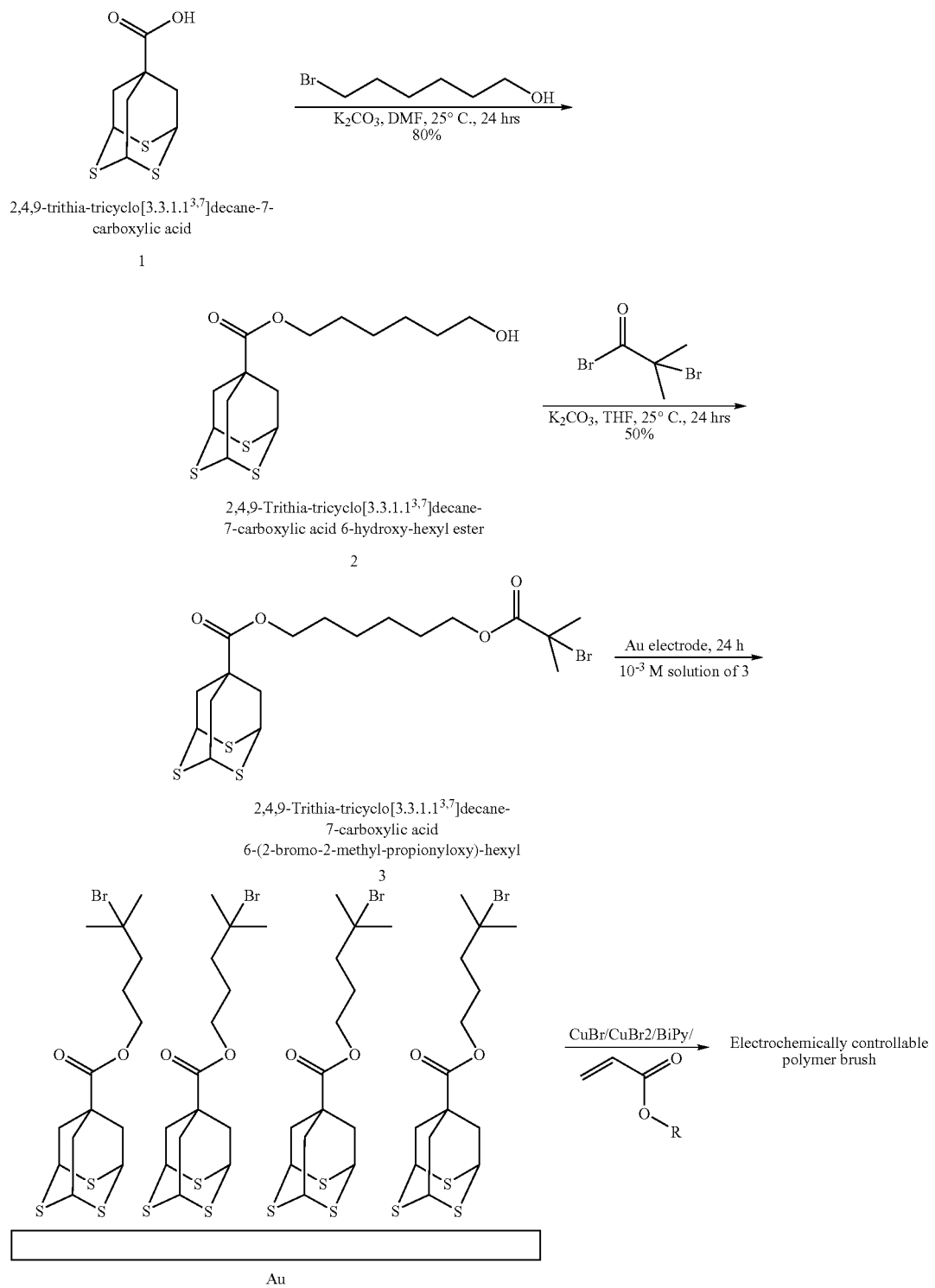

VII. Amplitude Modulation Embodiments

In another embodiment a multiplexed signal representing multiple channels is acquired and demodulated to recover individual channel signals. In this embodiment, a single pair of sensing electrodes and a single DAQ (Data Acquisition Board/System) channel are needed to recover multiple signals. The multiplexed multi-channel sensor design is similar to that presented hereinabove for example in FIG. 38, and more specifically FIG. 45, but a different measurement scheme is used. Specifically, major electrodes are positioned, one on each side of the sensing channels, and used to make a combined measurement with the multiplexed response of all channels.

In another embodiment, next generation integrated lab-on-a-chip devices for detection and quantification of important biological targets, including bacteria, viruses and DNA sequencing, urgently needed in public health monitoring and biomedical research, are developed. In order to provide such devices for field application, high density parallel sensing arrays that are capable of processing large volumes of sample in a reasonable time are needed. As has been established hereinabove, coulter counters are known tools for sizing and counting cells in colloidal particles. Such devices, however, are limited in the fact that they have relatively low throughput; such devices are fundamentally serial devices that scan particles individually as they pass through a microchannel, making real-time analysis of bulk fluid samples difficult.

In response to this need, in one embodiment, devices with parallel micro-channels, each channel being equipped with individual detection electronics, are provided. In such devices, each channel can essentially be considered an individual instrument. Multiplexed detection is necessary in devices where the number of channels is large and individual detection electronics are impractical. Therefore, by modulating signals from the individual channels differently, a multiplexed signal representing a number of channels can be acquired, and then that signal can be demodulated to recover the individual channel signals.

Figure 45:
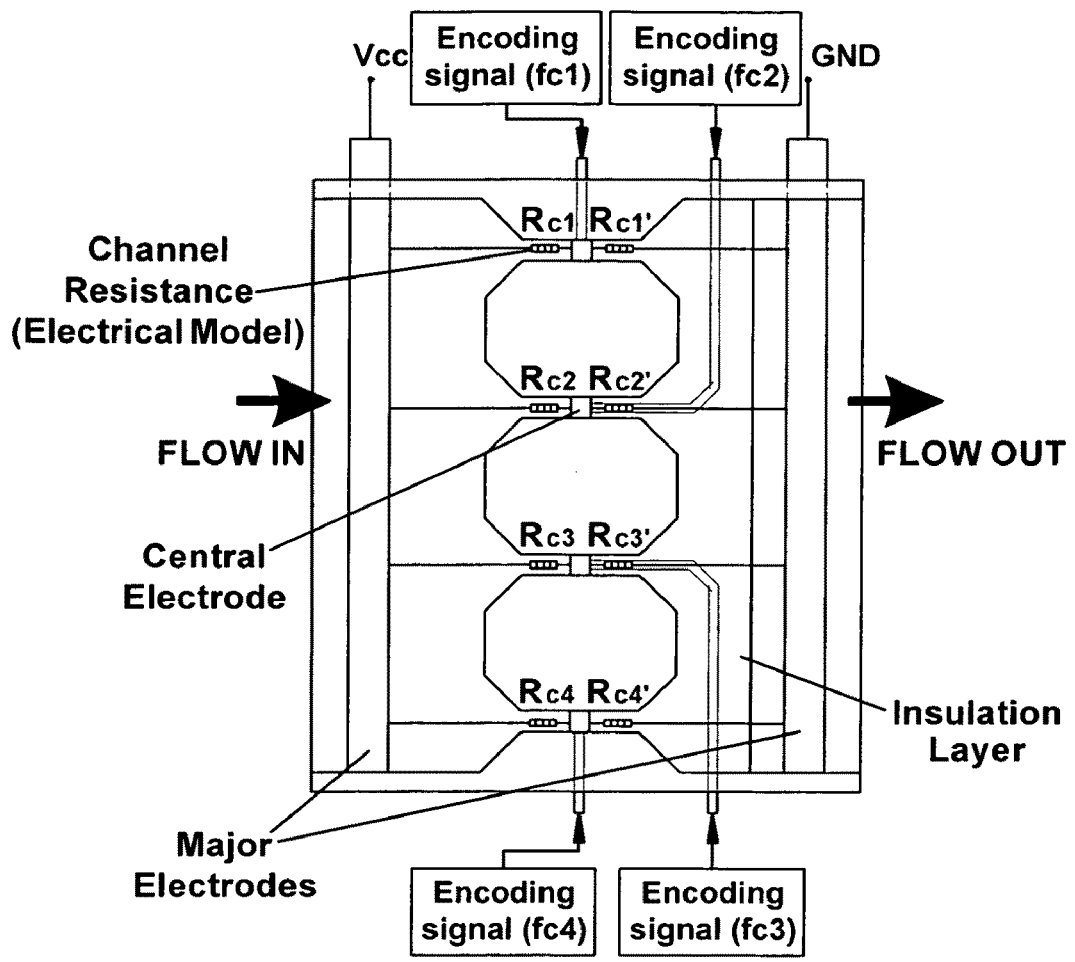
FIG. 45 is a schematic view of the multiplexed multichannel design allowing measurement using single detection electronics.

FIG. 45 shows the design concept of a multi-channel micro-fabricated coulter counter. The device consists of two reservoirs to load analytes, four parallel microfluidic channels, each being 400 µm×50 µm×40 µm, for counting particles, a pair, or one set, of main detection electrodes, one on each side of the microchannels to apply a constant DC bias ($V_{cc}$), and a central electrode in each microfluidic channel exposed only at the center to apply AC modulation signals. In this design, each central electrode divides the micro-channel in to two half microchannels. Devices of this design may be created by lithographic or micro-machine techniques in accord with the disclosure presented hereinabove. For example, a PDMS substrate can be micro-machined using soft lithography to create a device in keeping with the techniques disclosed herein or other suitable techniques.

Figure 46:
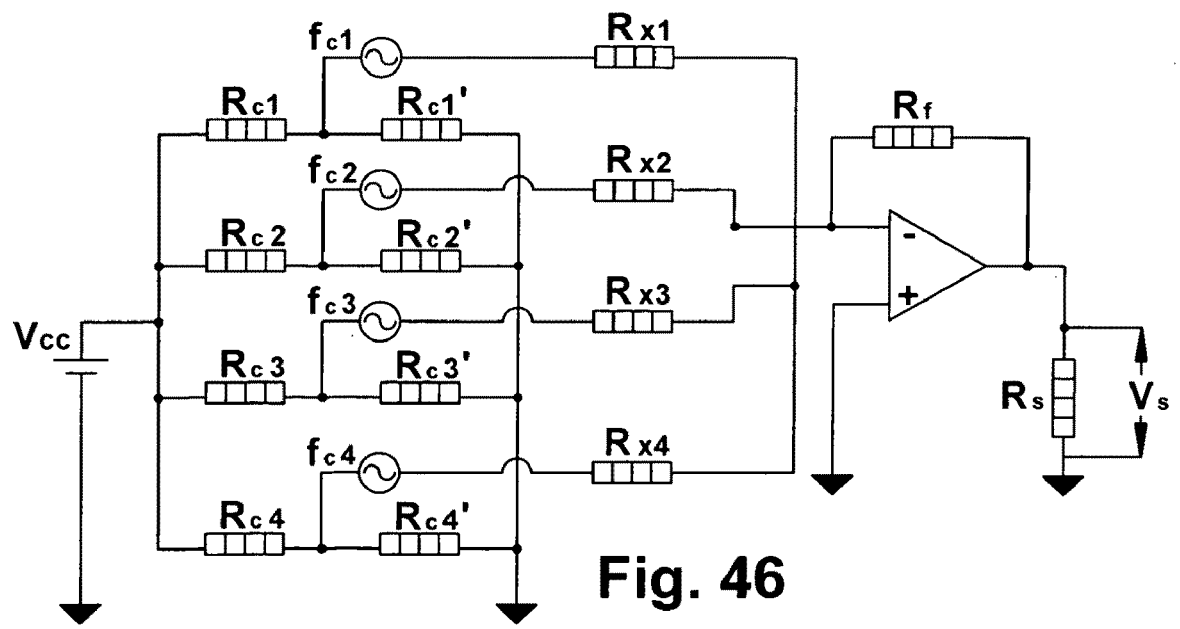
FIG. 46 is a simplified electrical model for a four channel device according to FIG. 45.

FIG. 46 provides a simplified equivalent circuit and measurement scheme for the four-channel device discussed above. Each half of a microchannel is modeled as a resistance ($R_{ci}$ & $R_{ci}'$). The current through each microchannel flows into a unity gain inverting summing amplifier through the center electrodes. The combined response, $V_s$, is monitored at the output across a sampling resistor $R_s$. The signal in each channel is modulated by an AC sine-wave of known and unique frequency (amplitude modulation). The combined response is demodulated to obtain the signals from each individual channel.

30 µm polystyrene particles suspended in 0.1M NaCl was used to test the device. Each of the central electrodes was connected to a sinusoidal AC voltage source to apply a modulation signal, specifically, 300 mV peak-to-peak, using a different frequency for each channel. The particle solution was injected through the inlet reservoir using a pressure-driven flow. The combined response, $V_s$, was measured at the output of the amplifier across a sampling resistor, $R_s$. The response was recorded at a sampling rate of 1 MHz using a NI PCI-6133 data acquisition board (DAQ) and a LabView interface.

Figure 47:
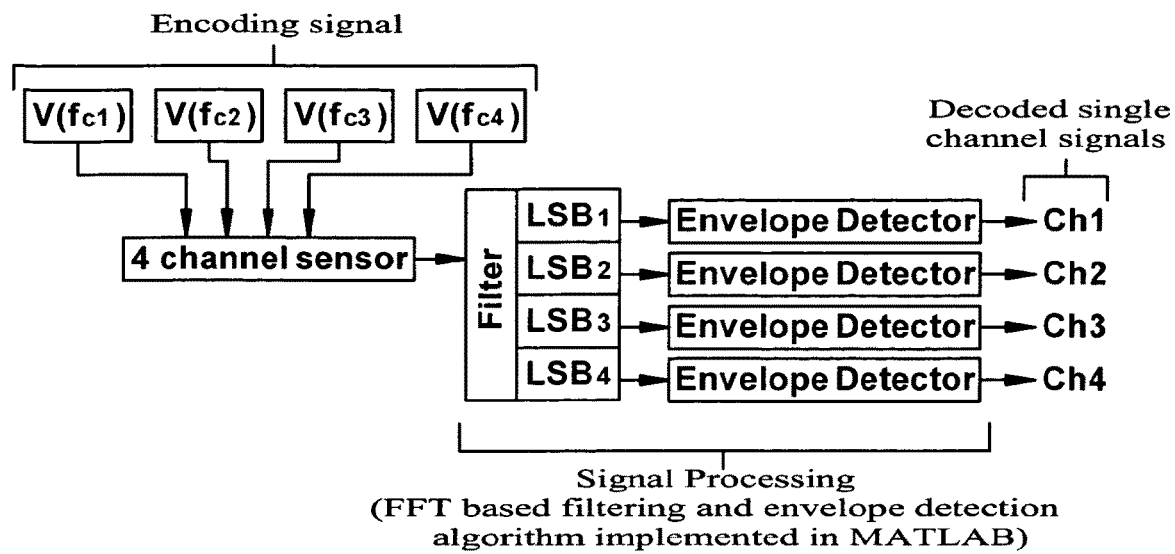
FIG. 47 is a block diagram for multiplexing using amplitude modulation for multi-channel resistive pulse sensing.

FIG. 47 provides a block diagram of the signal processing steps used to modulate the individual channel signals to produce a combined signal, and then demodulate the combined signal to recover the individual channel signals. The combined response ($V_s$) measured across the sampling resistor ($R_s$) was demodulated by filtering out all but the lower side band (LSB) for each channel. The filtering was accomplished using a rectangular window band pass filter based on a Fast Fourier Transform (FFT). To demodulate the signal for a channel modulated at frequency $f_c$, signal content in bandwidth varying from $f_c$-5 kHz2$f_c$ to 0.5 kHz was retained. Envelope detection was used on the resulting signal to remove the AC sine wave carrier and thus recover the signal for each individual channel. The filtering and envelope detecting were implemented using custom code written in MATLAB.

Piezoelectric micro-actuators can be used for dynamic modulation of micro-fluidic channels. To dynamically modulate multiple microchannels typically requires power supplies of high modulation frequency (typically 50 kHz) and high actuation voltage (>100V). However, the application of these power supplies to microfluidic devices is impractical and costly, which contradicts the goal of development of miniature, low cost bio-instruments.

In contrast, electrical-field-effect polymer brushes grown as a nanofilm on the surface of microchannels can switch between the extension and collapse status with a low applied driving voltage. The fast extension/collapse switching allows dynamic modulation of the conductance/impedance of electrolyte-filled microchannels. Thus the signals from each of the channels can be demodulated from the overall signal to produce the total counting/detecting signal without much increase in device complexity and power consumption.

Figure 48A:
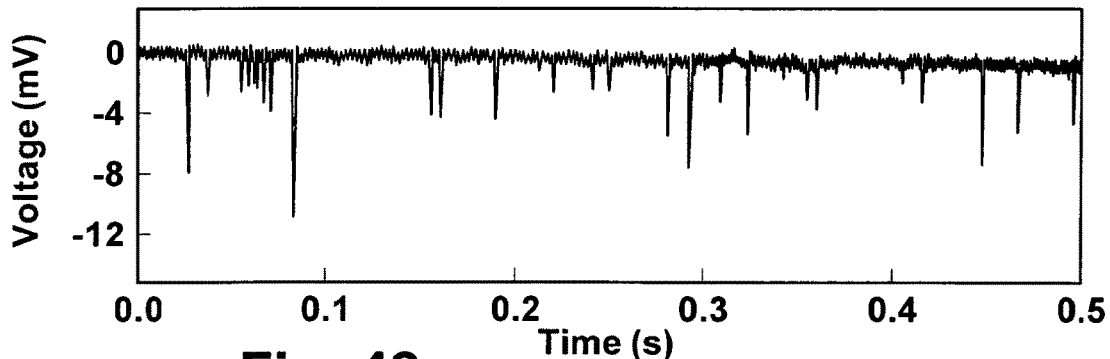
FIG. 48 (*a*)-(*b*) provide graph data for testing results for 30 μm polystyrene particles passing through a single channel counter.
Figure 48B:
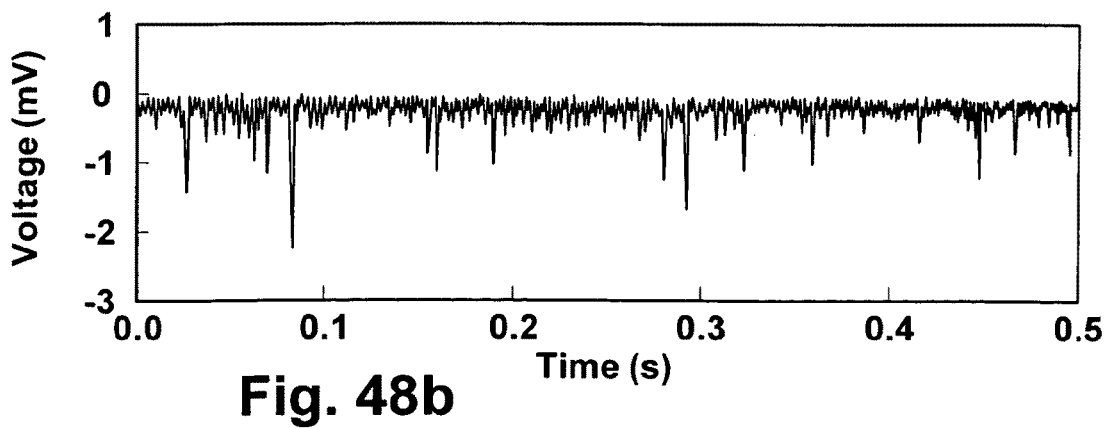

Signal recovery using amplitude modulation was demonstrated using measurements first made for a single channel device using both DC mode and amplitude modulation mode. A DC voltage ($V_{cc}$=1 V) was applied across the microchannel and an encoding AC signal (300 mVp-p, $f_c$=22 kHz) was applied through the central electrode. The combined response was recorded. The DC response was obtained by retaining the low frequency response (0-5 kHz) by filtering out the high frequency (<5 kHz) components from the measured response and the demodulation step, whereas the amplitude modulated response is obtained by retaining the LSB components with the bandwidth varying from 17 kHz to 21.5 kHz for $f_c$=22 kHz. The pulses of the demodulated response occur at the same times as those of the DC response, as set forth in FIG. 48. This FIG. 48 provides test results with the DC offset removed for 30-µm polystyrene particles passed through a single channel counter, $V_{cc}$=1V. In this figure, (a) shows the DC response, while (b) provides the demodulated response. Each pulse shown represents one particle passing through the microchannel. This test demonstrates the feasibility of particle detection using the amplitude modulation method.

Figure 49A:
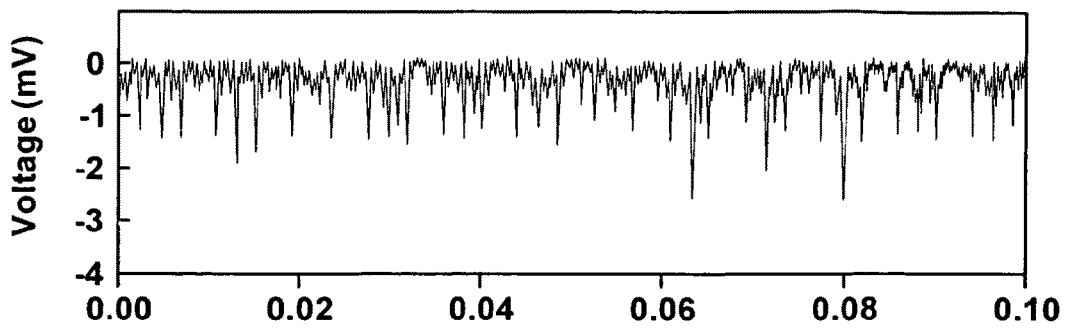
FIG. 49 provides graphs of measurements for two channels of a four channel device (a) channel 1 with an encoding frequency of $f_c$=20 kHz and (b) channel 4 with an encoding frequency of $f_c$=65 kHz.
Figure 49B:
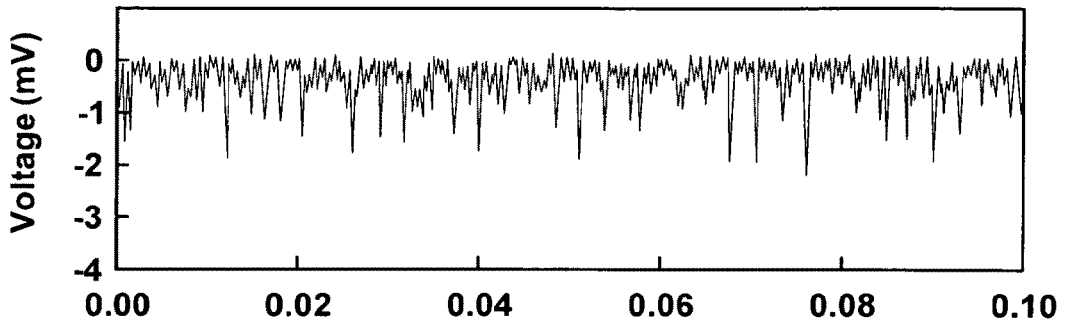

Following on the foregoing, a multiplexed measurement was done on two channels of the four-channel device. The two channels were modulated at frequencies $f_{c1}$=20 kHz and $f_{c2}$=65 kHz. Recovered signals for individual channels are shown in FIG. 49. FIG. 49 provides measurements for the two channels of the four-channel device wherein $V_{cc}$=1V, (a) shows channel 1 having encoded frequency $f_{c1}$=20 kHz and (b) shows channel 4 having encoded frequency $f_{c2}$=65 kHz. Each pulse represents one particle passing through the identified microchannel.

Figure 50A:
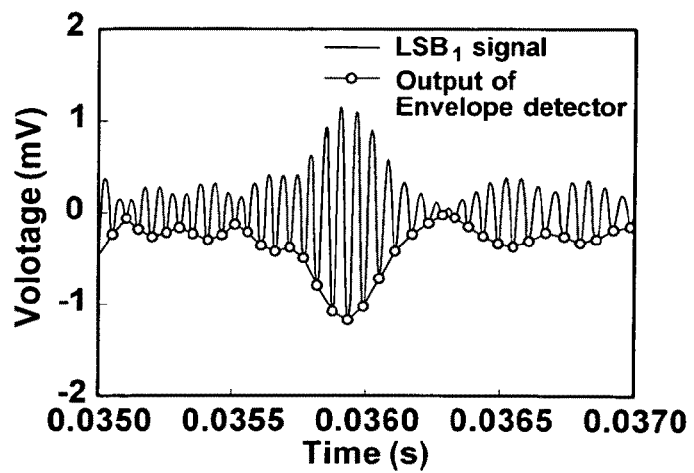
FIG. 50 provides graphs of (a) a section of the filtered signal from FIG. 49 showing the variation in voltage as a particle passes through the channel with superimposed output of the envelope detector and (b) output of the envelope detection showing a voltage pulse for channel 1.
Figure 50B:
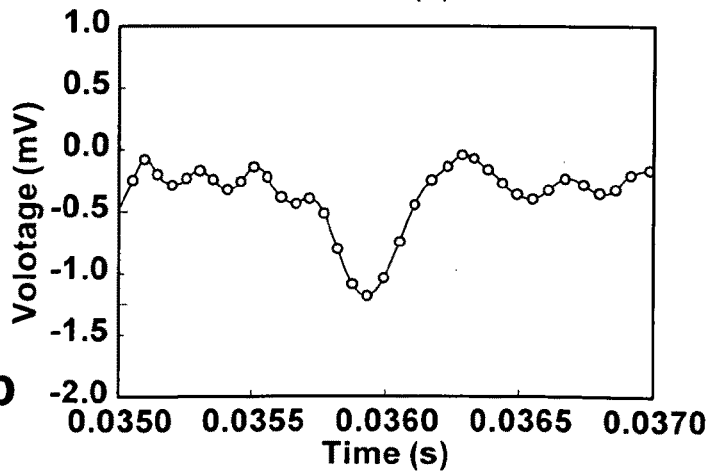

FIG. 50 illustrates details of the signal processing used to recover the signal for the first channel from the combined signal that is the output of the sensor. FIG. 50(a) is a selected section of the filtered signal for the LSB for channel 1 from FIG. 49 showing a variation in voltage as a particle passes through the channel with superimposed output of the envelope detector detecting the variation. FIG. 50(b) shows output of the envelope detection showing a voltage pulse for channel 1. FIG. 50(a) then shows the signal after applying the LSB filter to isolate the part of the combined signal that relates to the carrier frequency for the first channel. The circle data points on the plat indicate the results of envelope detection, which is used to remove the carrier signal. The output of the envelope detector, shown again in 50(*b*) is the recovered signal for the first channel.

Figure 51:
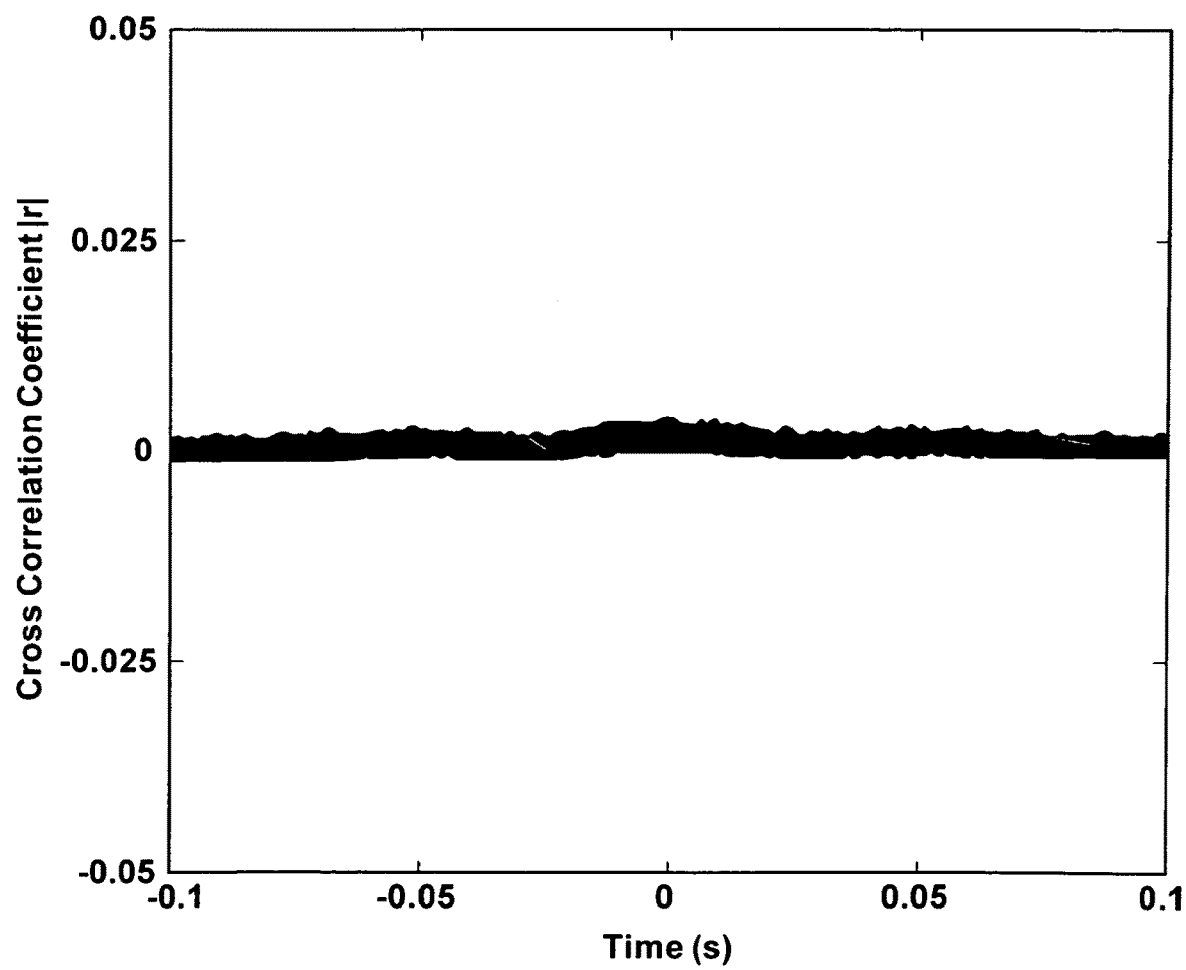
FIG. 51 provides a graph of the cross correlation analysis for the signals of two channels from FIG. 48.

It is noted that a change in the current of one channel has the potential to effect the response of a neighboring channel, thereby resulting in false detection of particles in the neighboring channel. Cross correlation analysis between the two channel signals, shown in FIG. 51, however, shows that the cross correlation coefficient is |r|<0.01 indicating cross talk between the two channels is negligible.

Figure 52:
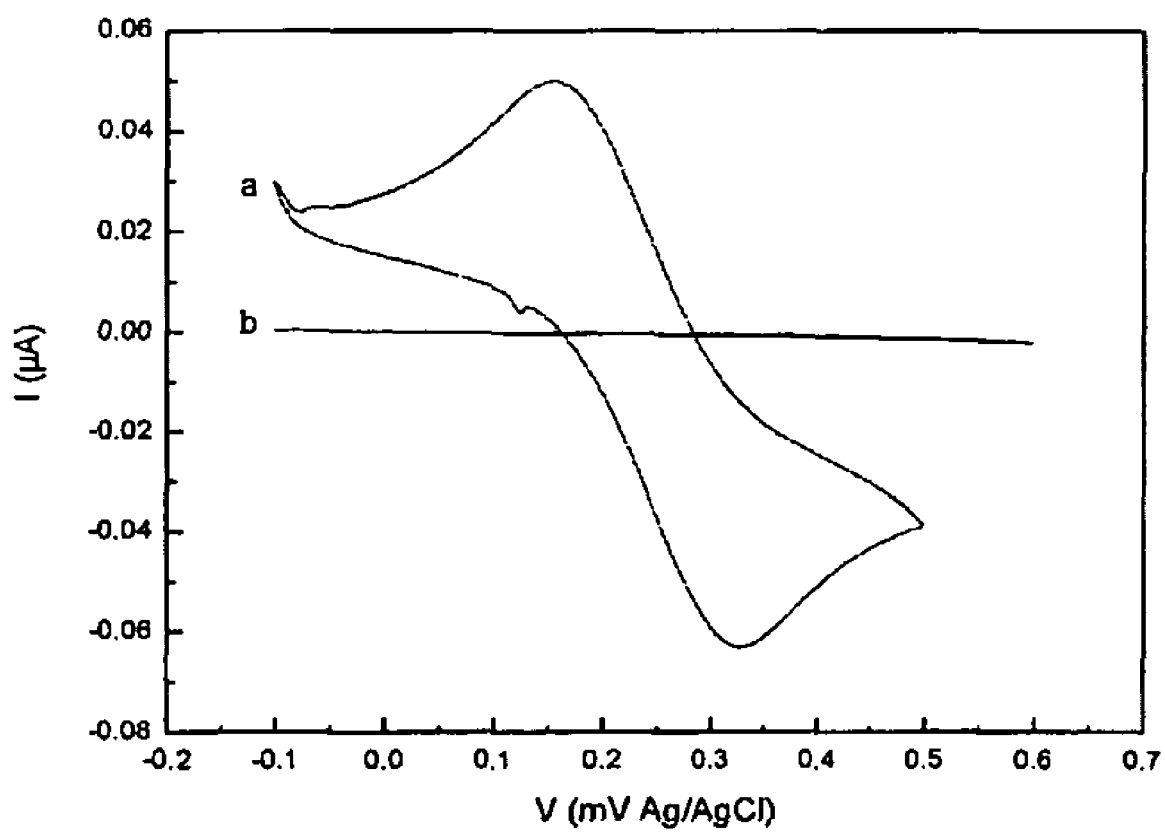
FIG. 52 provides cyclovoltammetry (CV) measurement results for the polymer brushes according to the invention.

Using the synthesis method described above, a surface anchor that can attach the polymer brushes to the electrode stably was synthesized. Cyclovoltammetry (CV) measurement results are presented in FIG. 52:

Specifically, FIG. 52 provides CV measurements obtained in a three electrode electrochemical cell employing the Gamry® Electrochemistry Workstation under the following conditions: 1.0 mM $K_3[Fe(CN_6)]/K_4[Fe(CN_6)]$, as the reversible redox pair, 0.1 M KCl as the supporting electrolyte, a Au electrode as the working electrode, a Pt wire as the counter electrode, and a Ag/AgCl electrode as the reference. (a) bare gold electrode; (b) initiator self-assembled monolayer (SAM) modified gold electrode.

In FIG. 52, after the gold surface was modified with the anchor and the polymer brush initiator, no redox peak of probe molecules and only very small response current was present (curve b), indicating good surface integrity of the SAM layer.

Figure 53:
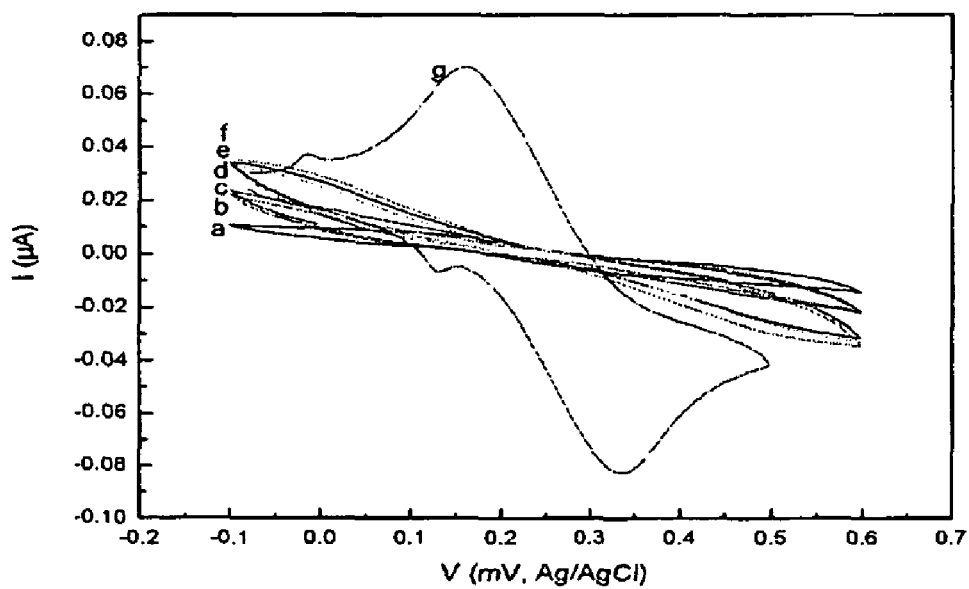
FIG. 53 provides further cyclovoltammetry results under specified conditions and after acetonitrile treatment.

FIG. 53 CV measurements obtained under the following conditions; 1.0 mM $K_3[Fe(CN_6)]/K_4[Fe(CN_6)]$ as the reversible redox pair, 0.1 M KCl as the supporting electrolyte, a Au electrode as the working electrode, a Pt wire as the counter electrode, and a Ag/AgCl electrode as the reference. (a) gold electrode modified with initiator SAM; (b), (c), (d), (e), (f) SAM modified gold electrode after being treated with 0.1 M acetonitrile for 15, 30, 45, 60, 90 minutes; (g) bare gold electrode.

Next, acetonitrile, a well-known competitive ligand which typically damages the thiol based surface SAM, was used to treat the initiator SAM attached on the working electrode. The CV measurements were taken every 15 minutes. FIG. 53 shows that after the SAM was treated with acetonitrile for up to 90 minutes, there was no redox peaks of probe molecules, suggesting that the initiator SAM has good surface integrity and stability.

Figure 54:
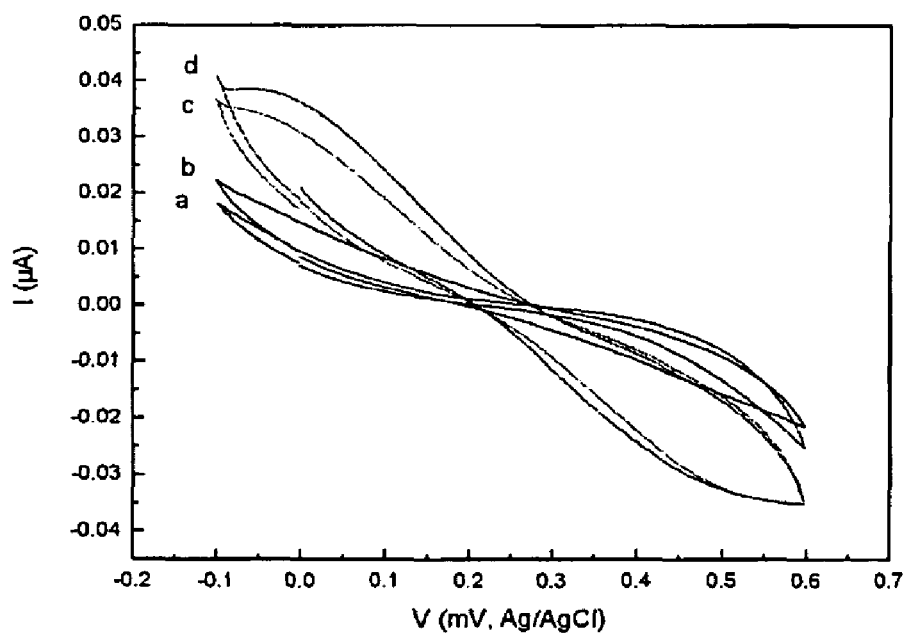
FIG. 54 provides comparative data for treatment with acetonitrile at various concentrations.

FIG. 54 provides the CV measurements after the SAM layer was treated for 15 minutes in acetonitrile at different concentrations from low to high. It is obvious that no redox peak appeared after the SAM was treated with high concentration (0.5M and 11.0M) acetonitrile. This further indicates the surface integrity and stability of the initiator SAM as synthesized.

Finally, surface polymerizations were performed with several new reaction conditions. Surface IR spectroscopy (PM-FTIRRAS) analysis was conducted. The initial experimental results, shown in FIG. 44 indicate that the desired polymer brush nanofilm was formed on the gold electrode surface successfully.

The foregoing examples are considered only illustrative of the principles of the invention rather than an exclusive list of embodiments. Further, since numerous modifications and changes will readily occur to those of ordinary skill in the art, the invention is not intended to be limited to the exact construction and operation shown and described, and accordingly, all suitable modifications and equivalents are within the scope of the present invention.

What we claim is:

1. A multichannel particle counting device comprising:
    a plurality of microfluidic channels for dividing a first reservoir and a second reservoir, and for maintaining fluid communication between the first and second reservoirs;
    each microfluidic channel including a control electrode, wherein each control electrode is substantially electrically isolated from any other control electrode;
    each control electrode encoded to respond to a specific frequency;
    the first and second reservoirs together including one set of detection electronics including a first electrode in electrical communication with a power supply and a second electrode in electrical communication with a measuring circuit;
    the one set of detection electronics being the collector for each signal from each control electrode and having a means to deconvolute the collected signals;
    the reservoirs containing an electrolyte solution containing particles to be counted; and
    a means for creating a net fluid flow of electrolyte from one reservoir to the other reservoir through the microfluidic channels.

2. The device of claim 1 wherein the control electrode is replaced by one of a micro-actuator and a nanoactuator.

3. The device of claim 2 wherein the control electrode is replaced by a microactuator that deforms the microfluidic channel.

4. The device of claim 3 wherein the micro-actuator is a cantilevered device.

5. The device of claim 2 wherein the control electrode is replaced by a nanoactuator.

6. The device of claim 5 wherein the nano-actuator comprises nano polymer brushes.

7. The device of claim 1 wherein the means for creating a net fluid flow is the presence of pressure, an electro-osmotic state and an electrophoretic state.

8. The device of claim 1 wherein the microfluidic channels are formed by at least one of lithography and micro-machining.

9. The device of claim 1 wherein the electrodes comprising the one set of detection electrodes are selected from Ag/AgCl, platinum, graphite, or a combination thereof.

10. The device of claim 1 wherein each control electrode comprises at least one of Ag/AgCl, platinum, or graphite.

11. A method for rapidly counting particles comprising:
    charging one reservoir of the device of claim 1 with an electrolyte solution containing at least one particle to be measured;
    applying a voltage across the electrodes comprising the one set of detection electrodes;
    allowing the particles to migrate from one reservoir to the other reservoir through the plurality of microfluidic channels;
    dynamically modulating the microfluidic channels;
    the one set of detection electrodes detecting multiple signals generated as particles pass through the plurality of microfluidic channels;
    deconvoluting the signals detected;
    correlating the signals to the number of particles passing through each microfluidic channel; and
    counting the deconvoluted signals.

12. The method of claim 11 wherein the signals are detected simultaneously and collected simultaneously by the one set of detection electronics.

13. The method of claim 11 wherein the microfluidic channels are dynamically modulated by a control electrode in each microfluidic channel.

14. The method of claim 13 wherein each control electrode is encoded to a different signal frequency.

15. The method of claim 11 wherein the microfluidic channels are dynamically modulated by at least one of a micro- or nano-actuator.

16. The method of claim 15 wherein each channel contains a separate micro- or nano-actuator.

17. The method of claim 15 wherein the micro- or nano-actuator is a channel deforming device.

18. The method of claim 17 wherein the deforming device responds to an electrical impulse by cantilevering the micro-actuator.

19. The method of claim 15 wherein the nano-actuator comprises nano polymer brushes that extend or relax in response to electric charge present within the device.

20. The method of claim 11 wherein the particles being counted are selected from one or more of pollen, dust, airborne contaminants, microbes, viruses, and biological warfare agents.

21. The method of claim 11 wherein the applied voltage is between 1 and 4 volts.

22. The method of claim 11 wherein the signals comprise current and/or voltage pulses.

23. The method of claim 11 wherein the combined signals are deconvoluted by applying the Hardmard Transformation or Fast Fourier Transformation technique to the signal data.

* * * * *